(12) United States Patent
Rosenbaum et al.

(10) Patent No.: US 11,293,056 B2
(45) Date of Patent: Apr. 5, 2022

(54) METHODS AND COMPOSITIONS FOR MANIPULATING NUCLEIC ACIDS

(71) Applicant: LIFE TECHNOLOGIES CORPORATION, Carlsbad, CA (US)

(72) Inventors: Abraham Rosenbaum, Waterbury, CT (US); Collyn Seeger, Middletown, CT (US); Jeremy Gray, Larkspur, CA (US); Hua Yu, Guilford, CT (US)

(73) Assignee: Life Technologies Corporation, Carlsbad, CA (US)

( * ) Notice: Subject to any disclaimer, the term of this patent is extended or adjusted under 35 U.S.C. 154(b) by 306 days.

(21) Appl. No.: 16/183,722

(22) Filed: Nov. 7, 2018

(65) Prior Publication Data

US 2019/0194719 A1    Jun. 27, 2019

Related U.S. Application Data

(60) Provisional application No. 62/582,597, filed on Nov. 7, 2017, provisional application No. 62/719,078, filed on Aug. 16, 2018.

(51) Int. Cl.
| | | |
|---|---|---|
| *C12Q 1/686* | (2018.01) | |
| *C12Q 1/6806* | (2018.01) | |
| *C12Q 1/6834* | (2018.01) | |
| *C12Q 1/6853* | (2018.01) | |
| *C12Q 1/6876* | (2018.01) | |
| *C12Q 1/6874* | (2018.01) | |

(52) U.S. Cl.
CPC ........... *C12Q 1/686* (2013.01); *C12Q 1/6806* (2013.01); *C12Q 1/6834* (2013.01); *C12Q 1/6853* (2013.01); *C12Q 1/6874* (2013.01); *C12Q 1/6876* (2013.01); *C12Q 2600/16* (2013.01)

(58) Field of Classification Search
CPC ... C12Q 1/6806; C12Q 1/6834; C12Q 1/6853
See application file for complete search history.

(56) References Cited

U.S. PATENT DOCUMENTS

| | | | |
|---|---|---|---|
| 5,223,414 A | 6/1993 | Zarling et al. | |
| 5,273,881 A | 12/1993 | Sena et al. | |
| 5,670,316 A | 9/1997 | Sena et al. | |
| 7,270,981 B2 | 9/2007 | Armes et al. | |
| 7,399,590 B2 | 7/2008 | Piepenburg et al. | |
| 7,435,561 B2 | 10/2008 | Piepenburg et al. | |
| 7,666,598 B2 | 2/2010 | Piepenburg et al. | |
| 7,763,427 B2 | 7/2010 | Piepenburg et al. | |
| 8,017,339 B2 | 9/2011 | Piepenburg et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 9,309,557 B2 | 4/2016 | Li et al. | |
| 9,309,558 B2 | 4/2016 | Li et al. | |
| 9,309,566 B2 | 4/2016 | Li et al. | |
| 9,334,531 B2 | 5/2016 | Li et al. | |
| 9,371,557 B2 | 6/2016 | Li et al. | |
| 9,476,080 B2 | 10/2016 | Li et al. | |
| 10,113,195 B2 | 10/2018 | Li et al. | |
| 10,233,488 B2 | 3/2019 | Li et al. | |
| 10,329,544 B2 | 6/2019 | Li et al. | |
| 2005/0153333 A1* | 7/2005 | Sooknanan | C12Q 1/6809 435/6.12 |
| 2009/0203531 A1 | 8/2009 | Kurn | |
| 2011/0262903 A1 | 10/2011 | Davidson et al. | |
| 2012/0156728 A1 | 6/2012 | Li et al. | |
| 2013/0203607 A1 | 8/2013 | Li et al. | |
| 2013/0225421 A1 | 8/2013 | Li et al. | |
| 2013/0281307 A1 | 10/2013 | Li et al. | |
| 2014/0080717 A1 | 3/2014 | Li et al. | |
| 2014/0147852 A1 | 5/2014 | Li et al. | |
| 2014/0148345 A1 | 5/2014 | Li et al. | |
| 2015/0275284 A1 | 10/2015 | Li et al. | |
| 2016/0032375 A1 | 2/2016 | Li et al. | |
| 2016/0272954 A1 | 9/2016 | Li et al. | |
| 2017/0067098 A1 | 3/2017 | Li et al. | |
| 2017/0292124 A1 | 10/2017 | Zhang et al. | |
| 2019/0119738 A1 | 4/2019 | Li et al. | |

FOREIGN PATENT DOCUMENTS

| | | |
|---|---|---|
| EP | 2839026 B1 | 8/2016 |
| EP | 2652148 B1 | 11/2016 |
| EP | 3095879 A1 | 11/2016 |

(Continued)

OTHER PUBLICATIONS

International Search Report and Written Opinion for Application No. PCT/US2018/059710, dated Mar. 1, 2019, 12 pages.
PCT/US2020/030853, International Search Report and Written Opinion, dated Aug. 26, 2020, 16 pages.
PCT/US2020/030853, Partial International Search Report and Written Opinion, dated Jul. 14, 2020, 12 pages.
Head et al., "Library Construction for Next-Generation Sequencing: Overviews and Challenges", BioTechniques, 2014, vol. 56, No. 2, pp. 61-77.

(Continued)

*Primary Examiner* — Samuel C Woolwine
*Assistant Examiner* — Carolyn L Greene

(57) ABSTRACT

The present disclosure provides methods, compositions and kits as well as systems for manipulating nucleic acids, including implementing isothermal amplification, such as recombinase-polymerase amplification (RPA), of a nucleic acid template using a pre-seeded solid support. Provided are rapid and efficient methods for generating template nucleic acid molecules comprising specific nucleotide sequence bound to solid support. Such methods can be used, for example, in manipulating nucleic acids in preparation for analysis methods that utilize monoclonal populations of nucleic acids.

19 Claims, 10 Drawing Sheets

Specification includes a Sequence Listing.

(56) References Cited

FOREIGN PATENT DOCUMENTS

| EP | 2888371 | B1 | 8/2017 |
| EP | 2895620 | B1 | 8/2017 |
| EP | 3257952 | A1 | 12/2017 |
| EP | 3260554 | A1 | 12/2017 |
| EP | 3095879 | B1 | 9/2018 |
| EP | 3147374 | B1 | 1/2019 |
| EP | 3461910 | A1 | 4/2019 |
| WO | WO-2012047889 | A2 | 4/2012 |
| WO | WO-2012083189 | A2 | 6/2012 |
| WO | WO-2013023176 | A2 | 2/2013 |
| WO | WO-2013123238 | A1 | 8/2013 |
| WO | WO-2013158313 | A1 | 10/2013 |
| WO | WO-2014031163 | A1 | 2/2014 |
| WO | WO-2014043143 | A1 | 3/2014 |
| WO | WO-2017161306 | A1 | 9/2017 |
| WO | WO-2019094524 | A1 | 5/2019 |

OTHER PUBLICATIONS

Ma et al., "Isothermal Amplification Method for Next-Generation Sequencing", Proceedings of the National Academy of Sciences, vol. 110, No. 5, Aug. 27, 2013, Pp. 14320-14323.

Törmänen et al., "Extension Product Capture Improves Genomic Sequencing and DNase I Footprinting by Ligation-Mediated PCR", Nucleic Acids Research, 1992, vol. 20, No. 20, pp. 5487-5488.

Zheng et al., "Anchored Multiplex PCR for Targeted Next-Generation Sequencing", Nature Medicine, 2014, vol. 20, pp. 1479-1484 with Online Methods.

* cited by examiner

SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: Synthetic DNA

<400> SEQUENCE: 1
cctctctatg ggcagtcggt gat       23

<210> SEQ ID NO 2
<211> LENGTH: 20

```
<212> TYPE: DNA
<213> ORGANISM: Artificial Sequence
<220> FEATURE:
<223> OTHER INFORMATION: Synthetic DNA

<400> SEQUENCE: 2
ccatctcatc cctgcgtgtc                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
cctatcccct gtgtgccttg                                            20

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
acgatccatc tcatccctgc gtgtc                                      25

<210> SEQ ID NO 5
<211> LENGTH: 39
<212> TYPE: DNA
<213> ORGANISM: Artificial Sequence
<220> FEATURE:
<223> OTHER INFORMATION: Synthetic DNA

<400> SEQUENCE: 5
tccataaggt cagtaacgat ccatctcatc cctgcgtgt                       39

<210> SEQ ID NO 6
<211> LENGTH: 61
<212> TYPE: DNA
<213> ORGANISM: Artificial Sequence
<220> FEATURE:
<223> OTHER INFORMATION: Synthetic DNA

<400> SEQUENCE: 6
cctatcccct gtgtgccttg gcagtctcag ccactacgcc tccgctttcc tctctatgga    60
a                                                                   61

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA

<400> SEQUENCE: 7
attcgagctg ttcatctgta tcttgcgcta ccaa                            34
```

METHODS AND COMPOSITIONS FOR MANIPULATING NUCLEIC ACIDS

CROSS-REFERENCE TO RELATED APPLICATIONS

This application claims the benefit of priority to U.S. Provisional Application No. 62/582,597, filed Nov. 7, 2017, entitled "METHODS AND COMPOSITIONS FOR ISOTHERMAL NUCLEIC ACID AMPLIFICATION" and to U.S. Provisional Application No. 62/719,078, filed Aug. 16, 2018, entitled "SYSTEM AND METHOD FOR PREPARING A SEQUENCING DEVICE," the disclosure of each of which is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "LT01179_ST25.txt" created on Feb. 27, 2019 and is 2,000 bytes in size. The sequence listing contained in this .txt file is part of the specification and is hereby incorporated by reference herein in its entirety.

INCORPORATION BY REFERENCE

The disclosures of any patents, patent applications, and publications cited herein are incorporated herein by reference in their entirety.

FIELD OF THE INVENTION

The present disclosure relates generally to methods for manipulating and analyzing nucleic acids, and compositions and kits for doing the same.

BACKGROUND

Manipulation of nucleic acid samples, such as, for example, nucleic acid amplification, is very useful in molecular biology and has wide applicability in practically every aspect of biology, therapeutics, diagnostics, forensics and research. Increasingly, biological and medical research is turning to nucleic acid sequencing for enhancing biological studies and medicine. For example, biologists and zoologists are turning to sequencing to study the migration of animals, the evolution of species, and the origins of traits. The medical community is using sequencing for studying the origins of disease, sensitivity to medicines, and the origins of infection. The use of sequencing can be limited by insufficient quantity and/or quality of the nucleic acids in a sample. Additionally, sequencing has historically been an expensive process, thus limiting its practice.

Generally, to increase the amount of nucleic acid available for analysis, amplicons are generated from a nucleic acid molecule using one or more primers, where the amplicons are complementary to all or a portion of the template from which they were generated. Multiplexed amplification can also streamline processes and reduce overheads. For some downstream applications, monoclonality is desirable because different characteristics of diverse nucleic acid molecules within a polyclonal population can complicate the interpretation of assay data. In instances where a monoclonal population of nucleic acids is desired for use in analytical methods, challenges also exist in containing monoclonal nucleic acid populations and keeping them segregated and free, or relatively free, of significant contamination by other nucleic acids that are not identical to those in the monoclonal population. This is particularly an issue when attempting to conduct analysis, e.g., sequencing, of multiple samples of different nucleic acids in a high-throughput, automated, cost-efficient manner. In nucleic acid sequencing applications, the presence of polyclonal populations can complicate the interpretation of sequencing data; however, many sequencing systems are not sensitive enough to detect nucleotide sequence data from a single template nucleic acid molecule, thus amplification of template nucleic acid molecules prior to sequencing is necessary.

One example of such amplification is recombinase-polymerase amplification (RPA), which is a DNA amplification process that utilizes enzymes to bind oligonucleotide primers to their complementary partners in duplex DNA followed by isothermal amplification. RPA offers a number of advantages over traditional methods of amplification including, e.g., lack of need for initial thermal or chemical melting, ability to operate at low constant temperatures without absolute temperature control, and a reaction mixture (e.g., lacking a target polynucleotide) can be stored in a dried condition. These advantages demonstrate that RPA is a powerful and convenient tool for amplifying nucleic acid molecules. However, attempts at using RPA to prepare template nucleic acid molecules prior to sequencing have resulted in undesirable polyclonal populations and/or insufficient preparations. Thus, there remains a need for improved methods generating improved preparations of template nucleic acid molecules for molecular characterization, e.g., sequencing.

SUMMARY

In some embodiments, the disclosure relates generally to methods, as well as systems, compositions, kits and apparatuses for performing the methods, of manipulating nucleic acids.

In some embodiments, rapid and efficient methods for generating a nucleic acid molecule comprising a specific nucleotide sequence are provided herein. Such methods can be used, for example, in manipulating nucleic acids in preparation for analysis in methods that utilize monoclonal populations of nucleic acids. Some embodiments of clonal amplification methods disclosed herein for generating monoclonal nucleic acid populations begin with a confined nucleic acid molecule template. Methods of confining nucleic acid molecules provided herein include capture of single nucleic acid molecules through the binding of a specific nucleotide sequence common to different nucleic acids to be amplified and analyzed. To generate different nucleic acid molecules having a common specific nucleotide that can be used for ease of confinement, one method disclosed herein includes (a) obtaining a population of nucleic acid molecules, such as, for example, a double-stranded, adapter-containing DNA library, in which each molecule contains, with respect to one of the strands of the molecule, a first sequence of contiguous nucleotides at the 5' end of the molecule, a second sequence of contiguous nucleotides at the 3' end of the molecule and a third nucleotide sequence positioned between the first and second nucleotide sequences, wherein the first and second nucleotide sequences are different, the first nucleotide sequences of the nucleic acid molecules are substantially identical and the second nucleotide sequences of the nucleic acid molecules are substantially identical; (b) subjecting the population of nucleic acid molecules to a cycle of nucleic acid amplification in the presence of a forward primer containing an oligonucleotide sequence substantially identical to the first nucleotide sequence and a reverse primer containing an oligonucleotide sequence complementary to a subsequence of the 5' end of the second nucleotide sequence that is linked at the 3' end of the subsequence to a fourth nucleotide sequence that is not complementary to the second nucleotide sequence; and (c) subjecting the products of the cycle of amplification of step (b) to a cycle of amplification in the presence of the forward and reverse primers to generate multiple different nucleic acid products in which only one of the products comprises a sequence of nucleotides complementary to the fourth nucleotide sequence. In some embodiments of this method, the reverse primer includes a nucleotide sequence complementary to the 5' end of the second nucleotide sequence but does not contain a nucleotide sequence complementary to the 3' end of the second nucleotide sequence.

Other embodiments of methods provided herein of generating different nucleic acid molecules having a common specific nucleotide sequence that can be used, for example, for ease of confinement include (a) obtaining a population of nucleic acid molecules, such as, for example, a double-stranded, adapter-containing DNA library, in which each molecule contains, with respect to one of the strands of the molecule, a first sequence of contiguous nucleotides at the 5' end of the molecule, a second sequence of contiguous nucleotides at the 3' end of the molecule and a third nucleotide sequence positioned between the first and second nucleotide sequences, wherein the first and second nucleotide sequences are different, the first nucleotide sequences of the nucleic acid molecules are substantially identical and the second nucleotide sequences of the nucleic acid molecules are substantially identical; and (b) subjecting the population of nucleic acid molecules to two or more cycles of nucleic acid amplification in the presence of one or more forward primers containing an oligonucleotide sequence substantially identical to the first nucleotide sequence and a reverse primer that is blocked at the 3' end and contains an oligonucleotide sequence complementary to the second nucleotide sequence that is linked at the 5' end of the oligonucleotide sequence to a fourth nucleotide sequence that is not complementary to the second nucleotide sequence to generate nucleic acid products in which substantially all of the products comprise a sequence of nucleotides complementary to the fourth nucleotide sequence.

In some embodiments, provided herein are methods for generating one or more templated supports, such as, for example, solid supports. Such methods include, for example: a) forming a templating reaction mixture by combining one or more pre-seeded supports, nucleotides, a recombinase, and a polymerase, wherein the one or more pre-seeded solid supports include a population of attached substantially identical first primers and have substantially monoclonal template nucleic acid molecules attached thereto, wherein the one or more pre-seeded solid supports are formed in a separate pre-seeding reaction that precedes a templating reaction, wherein the substantially monoclonal template nucleic acid molecules include a proximal segment including the first primer, which, in some embodiments, does not include 100 or more identical nucleotides, wherein the proximal segment attaches a template nucleic acid segment to a pre-seeded solid support, and wherein the pre-seeded solid supports further include attached first primers that are attached to the pre-seeded solid support and are not bound to template nucleic acid molecules, wherein the templating reaction mixture further includes a population of substantially identical soluble second primers, and wherein the template nucleic acid molecules include a primer binding site for the second primer at or near the terminal end that is opposite the proximal segment; and b) performing the templating reaction by adding a cation to the templating reaction mixture and incubating the reaction mixture under isothermal conditions for at least 10 minutes to amplify the template nucleic acid molecules in a templating reaction to generate one or more templated solid supports, wherein each of the templated solid supports includes at least 100,000 substantially monoclonal template nucleic acid molecules, and wherein template nucleic acid molecules are not present in solution in the reaction mixture when the templating reaction is initiated, thereby generating one or more templated solid supports. In some embodiments, the one or more templated solid supports are used in a sequencing reaction to determine the sequences of the template nucleic acid molecules. In further embodiments, the templated solid supports are templated beads and the sequencing include distributing the beads in wells of a solid support before a sequencing reaction is performed. In some embodiments, the one or more templated solid supports include a first templated solid support that is attached with a substantially monoclonal population of template nucleic acid molecules having a first sequence, and at least one other templated solid support that is attached with a substantially monoclonal population of template nucleic acid molecules having a second sequence, wherein the sequence of the first attached template nucleic acid molecules differ from the sequence of the second attached template nucleic acid molecules. In further embodiments, the substantially monoclonal template nucleic acid molecules attached to each pre-seeded solid support include at least 70% of all template nucleic acid molecules attached to each pre-seeded solid support. In some embodiments, the templating reaction mixture includes a population of pre-seeded solid supports. In further embodiments, each pre-seeded solid support of the population of solid supports has between 10 and 50,000 substantially monoclonal template nucleic acid molecules attached thereto and the one or more solid supports are beads. In some embodiments, the pre-seeding reaction mixture and/or the templating reaction mixture further includes a recombinase-accessory protein. In further embodiments, the recombinase-accessory protein is a single-stranded binding protein and/or a recombinase-loading protein. In some embodiments, the templating reaction mixture and/or the pre-seeding reaction mixture is incubated at a temperature between 35° C. and 45° C. In some embodiments, the templating reaction mixture is incubated for between 10 and 60 minutes. In some embodiments, at least 100 times as many substantially monoclonal template nucleic acid molecules are present on the templated solid supports as were present on the pre-seeded solid supports.

In some embodiments, the disclosure relates generally to methods, as well as systems, compositions, kits and apparatuses for performing the methods, wherein the methods are for determining the sequences of template nucleic acid molecules, and include: performing a pre-seeding reaction and a subsequent templating reaction. In some embodiments, the pre-seeding reaction generates a plurality of pre-seeded solid supports wherein individual pre-seeded supports in the plurality of pre-seeded solid supports include a plurality of first primers attached to the solid supports, wherein the plurality of first primers have a substantially identical sequence, and wherein some of the plurality of the first primers are joined to a template nucleic acid molecule and some of the plurality of the first primers are not joined to a template nucleic acid molecule. In some embodiments, the disclosure relates generally to methods, as well as systems, compositions, kits and apparatuses for determining the sequences of template nucleic acid molecules, including: a) generating a population of pre-seeded solid supports including a population of attached identical first primers, wherein the pre-seeded solid supports are generated under pre-seeding conditions and wherein each of the pre-seeded solid supports has between 10 and 100,000 substantially monoclonal template nucleic acid molecules including the first primer attached thereto, and includes attached first primers that are attached to the pre-seeded solid supports and are not bound to template nucleic acid molecules; b) forming a templating reaction mixture by combining the population of pre-seeded solid supports, nucleotides, a recombinase, a polymerase, and a population of identical second primers in solution not attached to any substrate, wherein the template nucleic acid molecules include a primer binding site for the second primer at or near the terminal end that is opposite a proximal segment including the first primer; c) initiating a templating reaction by adding a cation to the templating reaction mixture, wherein template nucleic acid molecules are not present in solution in the reaction mixture when the templating reaction is initiated; d) incubating the initiated templating reaction mixture under isothermal conditions for at least 10 minutes to amplify the template molecules in a templating reaction to generate one or more templated solid supports including at least 10 times as many attached substantially monoclonal template nucleic acid molecules on the templated solid supports as were present on the pre-seeded solid supports; and e) sequencing template nucleic acid molecules on the one or more templated solid supports, thereby determining the sequences of template nucleic acid molecules. In some embodiments, the template nucleic acid molecules include two or more template nucleic acid molecules with different sequences. In some embodiments, the substantially monoclonal template nucleic acid molecules, which are attached to a pre-seeded solid support and/or are attached to a templated solid support, include template nucleic acid molecules having two or more different sequences. In further embodiments, the substantially monoclonal template nucleic acid molecules attached to each pre-seeded solid support include at least 70% of all template nucleic acid molecules attached to each pre-seeded solid support. In some embodiments, the templated solid supports are templated beads and the sequencing include distributing the beads in wells of a solid support before a sequencing reaction is performed. In some embodiments, each pre-seeded solid support of the population of solid supports has between 10 and 50,000 substantially monoclonal template nucleic acid molecules attached thereto and the one or more solid supports are beads. In some embodiments, the pre-seeding reaction mixture and/or the templating reaction mixture further includes a recombinase-accessory protein. In further embodiments, the recombinase-accessory protein is a single-stranded binding protein and/or a recombinase-loading protein. In some embodiments, the templating reaction mixture and/or the pre-seeding reaction mixture is incubated at a temperature between 35° C. and 45° C. In some embodiments, the templating reaction mixture is incubated for between 10 and 60 minutes. In some embodiments, the pre-seeded solid supports are generated using a first recombinase-polymerase amplification (RPA) reaction and the templating reaction is a second RPA reaction. In further embodiments, the first RPA reaction is performed by incubating an RPA reaction mixture for 2 to 5 minutes at a temperature between 35° C. and 45° C. In some embodiments, at least 100 times as many substantially monoclonal template nucleic acid molecules are present on the templated solid supports as were present on the pre-seeded solid supports.

In some embodiments, the disclosure relates generally to methods, as well as systems, compositions, kits and apparatuses for performing the methods, wherein the methods are for determining the sequences of template nucleic acid molecules, and include: a) performing a pre-seeding reaction by incubating a first recombinase-polymerase amplification (RPA) reaction mixture including a population of template nucleic acid molecules and a population of solid supports including a population of attached identical first primers under pre-seeding reaction conditions to generate one or more pre-seeded solid supports, wherein the pre-seeding reaction conditions include incubating the RPA reaction mixture under isothermal conditions and wherein the pre-seeded solid supports each have between 10 and 100,000 substantially monoclonal nucleic acid molecules attached thereto and/or the pre-seeding reaction conditions include incubating the RPA reaction mixture for 2 to 5 minutes under isothermal conditions, wherein the pre-seeded solid supports include: (i.) a substantially monoclonal population of template nucleic acid molecules attached to the solid support by the first primer, and (ii.) attached first primers that are attached to the pre-seeded solid supports and are not bound to template nucleic acid molecules; b) forming a templating reaction mixture by including the one or more pre-seeded solid supports in a second RPA reaction mixture, wherein template nucleic acid molecules not associated with the pre-seeded solid supports are not included in the templating reaction mixture, wherein the templating reaction mixture further includes a population of identical second primers in solution not attached to any substrate, and wherein the template nucleic acid molecules include a primer binding site for the second primer at or near the terminal end that is opposite a proximal segment comprising the first primer; c) initiating a templating reaction by adding a cation to the templating reaction mixture; d) incubating the initiated templating reaction mixture under isothermal conditions for at least 10 minutes to amplify the template nucleic acid molecules in a templating reaction to generate one or more templated solid supports including at least 10 times as many substantially monoclonal template nucleic acid molecules on the templated solid supports as were present on the pre-seeded solid supports; and e) sequencing template nucleic acid molecules on the one or more templated solid supports, thereby determining the sequence of a template nucleic acid molecules. In some embodiments, the template nucleic acid molecules includes two or more template nucleic acid molecules with different sequences. In some embodiments, the substantially monoclonal template nucleic acid molecules, which are attached to a pre-seeded solid support and/or are attached to a templated solid support, include template nucleic acid molecules having two or more different sequences. In further embodiments, the substantially monoclonal template nucleic acid molecules attached to each pre-seeded solid support includes at least 70% of all template nucleic acid molecules attached to each pre-seeded solid support. In some embodiments, the templated solid supports are templated beads and the sequencing includes distributing the beads in wells of a solid support before a sequencing reaction is performed. In some embodiments, each pre-seeded solid support of the population of solid supports has between 10 and 50,000 substantially monoclonal template nucleic acid molecules attached thereto and the one or more solid supports are beads. In some embodiments, the pre-seeding reaction mixture and/or the templating reaction mixture further includes a recombinase-accessory protein. In further embodiments, the recombinase-accessory protein is a single-stranded binding protein and/or a recombinase-loading protein. In some embodiments, the templating reaction mixture and/or the pre-seeding reaction mixture is incubated at a temperature between 35° C. and 45° C. In some embodiments, the templating reaction mixture is incubated for between 10 and 60 minutes. In some embodiments, at least 100 times as many substantially monoclonal template nucleic acid molecules are present on the templated solid supports as were present on the pre-seeded solid supports.

In some embodiments, the disclosure relates generally to compositions, as well as systems, methods, kits and apparatuses relating to the compositions, wherein the compositions include a templating reaction mixture including a population of pre-seeded solid supports, nucleotides, a recombinase, and a polymerase, wherein the population of pre-seeded solid supports have between 10 and 50,000 substantially monoclonal template nucleic acid molecules including a first primer attached thereto and further include attached first primers that are attached to the pre-seeded solid support and are not bound to template nucleic acid molecules, wherein the reaction mixture does not include a cation capable of initiating a recombinase-polymerase amplification reaction, and wherein at least 95% of the template nucleic acid molecules in the reaction mixture are attached to the one or more solid supports. In some embodiments, the template nucleic acid molecules includes two or more template nucleic acid molecules with different sequences. In some embodiments, the substantially monoclonal template nucleic acid molecules, which are attached to a pre-seeded solid support and/or are attached to a templated solid support, include template nucleic acid molecules having two or more different sequences. In some embodiments, the pre-seeded solid supports are pre-seeded beads. In some embodiments, the templating reaction mixture includes a recombinase-accessory protein. In further embodiments, the recombinase-accessory protein is a single-stranded binding protein and/or a recombinase-loading protein. In some embodiments, the pre-seeded solid supports are generated using a first recombinase-polymerase amplification (RPA) reaction. In further embodiments, the first RPA reaction is performed by incubating an RPA mixture for 2 to 5 minutes at a temperature between 35° C. and 45° C. In some embodiments, the pre-seeding reaction mixture further includes a population of identical second primers in solution, and the template nucleic acid molecules includes a primer binding site for the first primer at or near a first terminus. In some embodiments, the templating reaction mixture further includes a cation capable of initiating a recombinase-polymerase amplification reaction.

In some embodiments of the methods for generating one or more templated supports, such as, for example, solid supports provided herein, at least some, most or all of the nucleic acids attached to the templated support or supports generated in the method contain at least one modified nucleotide that includes an attachment, e.g., a first linker moiety, thereto. Such methods may further include linking the templated support(s) to a magnetic bead having a moiety (e.g., a binding partner or second linker moiety) to which the modified nucleotide(s) of the nucleic acids attached to the templated support can bind, link or attach via the attachment or linker of the modified nucleotide(s) thereby forming a bead assembly of the templated support and the magnetic bead. In some embodiments of these methods, the bead assembly is separated from any elements that do not include a magnetic bead by applying a magnetic field to the bead assembly thereby separating the bead assembly away from any such elements and forming an enriched population of templated supports. In some embodiments of the methods, the separated bead assembly is further subjected to conditions under which the templated support is released from the magnetic bead and is analyzed in further methods, e.g., sequencing methods.

Also provided herein are methods of preparing a device for analysis of a nucleic acid, such as, for example, sequencing of a nucleic. In some embodiments, the method includes generating a nucleic acid containing a capture sequence portion, a template portion and a primer portion containing a first linker moiety, capturing, for example through hybridization, the nucleic acid on a support, e.g., a solid support such as a bead, having a plurality of capture primers complementary to the capture sequence portion of the nucleic acid, linking the first linker moiety of the captured nucleic acid to a second linker moiety contained on a magnetic bead to form a bead assembly of the captured nucleic acid on the support and the magnetic beads, applying a magnetic field to the bead assembly thereby separating the bead assembly away from any elements that do not include a magnetic bead, releasing the captured nucleic acid on the support from the magnetic bead, mixing the released captured nucleic on the support with magnetic beads to which the captured nucleic acid on the support does not attach, link or bind and incorporating the mixture into a device for analysis of the captured nucleic acid. In some embodiments, the mixture of captured nucleic acid on the support and magnetic beads is applied to a surface, e.g., a chip, such as a semiconductor chip, and a magnetic field is applied to the surface. The surface may contain microwells into which the captured nucleic acid on the support is loaded through the movement of the magnetic beads over the surface as the magnetic field is applied to the surface. In some such embodiments, the size of the magnetic bead is such that the magnetic beads cannot enter the microwells.

In some embodiments of the methods of preparing a device for analysis of a nucleic acid, the method includes generating a nucleic acid containing a capture sequence portion, a template potion and a primer portion containing a first linker moiety, capturing the nucleic acid on a support, e.g., a solid support such as a bead, having a plurality of capture primers complementary to the capture sequence portion of the nucleic acid, linking the captured nucleic acid to a magnetic bead having a second linker moiety to form a bead assembly such that the first and second linker moieties are attached and loading the bead assembly into a well of the device using a magnetic field.

BRIEF DESCRIPTION OF THE DRAWINGS

FIG. 1A shows the read lengths using Ion Sphere Particles (ISPs) with no pre-seeded template (no template control (NTC)).

FIG. 1B shows the read lengths using ISPs pre-seeded with ~70 copies/ISP.

FIG. 1C shows the read lengths using ISPs pre-seeded with ~665 copies/ISP.

FIG. 1D shows the read lengths using ISPs pre-seeded with ~4,170 copies/ISP (FIG. 1D).

FIG. 2A shows the percent ISP loading for NTC ISPs and ISPs pre-seeded with different template copy numbers.

FIG. 2B shows the percent usable reads from NTC ISPs and ISPs pre-seeded with different template copy numbers.

FIG. 2C shows the number of total reads from NTC ISPs and ISPs pre-seeded with different template copy numbers.

FIG. 2D shows the mean, median, and mode of the read lengths from NTC ISPs and ISPs pre-seeded with different template copy numbers.

FIG. 2E shows the percent empty wells for NTC ISPs and ISPs pre-seeded with different template copy numbers.

FIG. 2F shows the percent low quality wells for NTC ISPs and ISPs pre-seeded with different template copy numbers.

FIG. 3A shows the percent ISP loading for NTC ISPs and ISPs pre-seeded with different template copy numbers.

FIG. 3B shows the percent usable reads from NTC ISPs and ISPs pre-seeded with different template copy numbers.

FIG. 3C shows the number of total reads from NTC ISPs and ISPs pre-seeded with different template copy numbers.

FIG. 3D shows the mean, median, and mode of the read lengths from NTC ISPs and ISPs pre-seeded with different template copy numbers.

FIG. 3E shows the percentage of empty wells for ISPs pre-seeded with different template copy numbers.

FIG. 3F shows the percentage of low quality wells for ISPs pre-seeded with different template copy numbers.

Figure 1A:
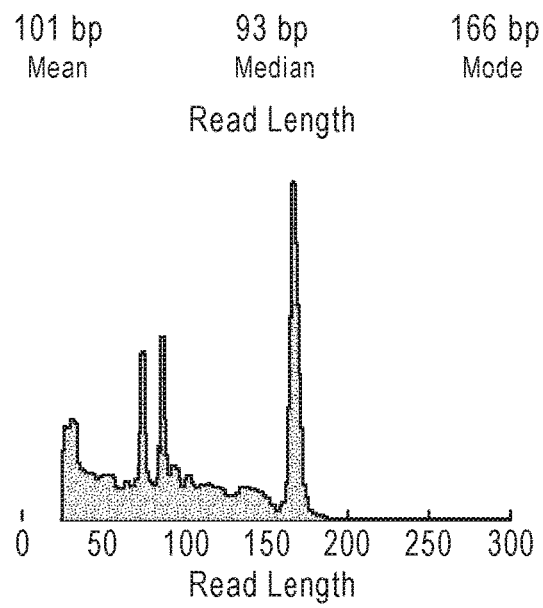
FIGS. 1A to 1D are histograms showing the read lengths in high-throughput sequencing after bulk isothermal amplification.
Figure 1B:
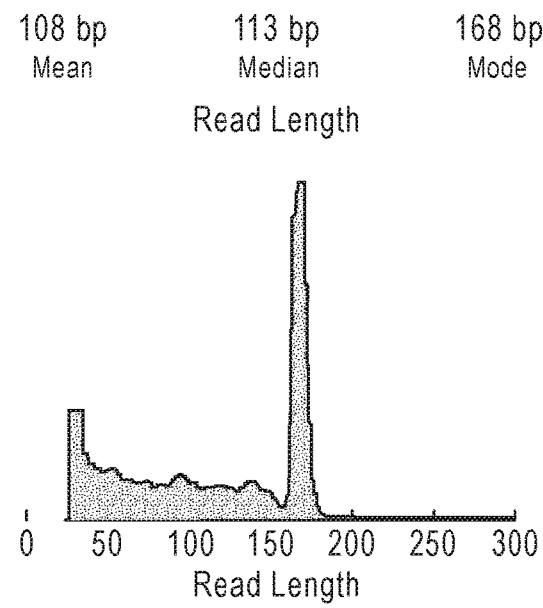
Figure 1C:
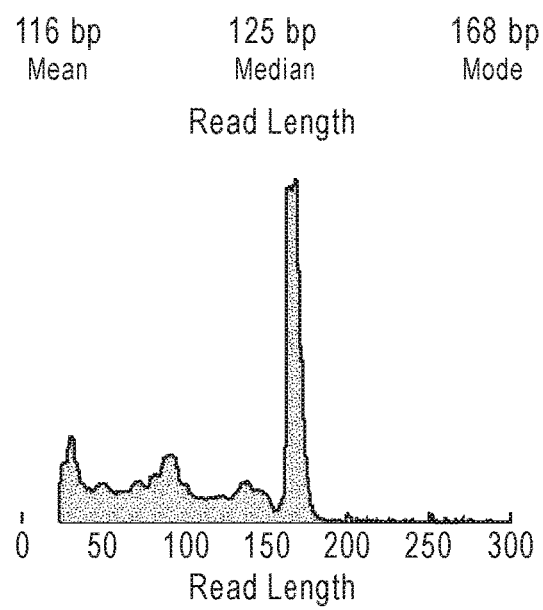
Figure 1D:
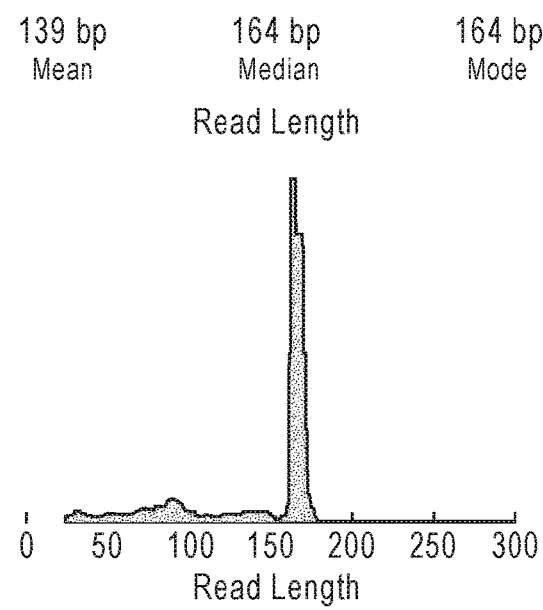

The above-identified figures are provided by way of representation and not limitation.

DEFINITIONS

As utilized in this disclosure, the following terms shall be understood to have the following meanings:

The term "monoclonal" and its variants, when used in reference to one or more polynucleotide populations, refers to a population of polynucleotides where at about 50-99%, or up to 100% of the members of the population share at least 80% identity at the nucleotide sequence level. As used herein, the phrase "substantially monoclonal" and its variants, when used in reference to one or more polynucleotide populations, refer to one or more polynucleotide populations wherein an amplified template polynucleotide molecule is the single most prevalent polynucleotide in the population. Accordingly, all members of a monoclonal or substantially monoclonal population need not be completely identical or complementary to each other. For example, different portions of a polynucleotide template can become amplified or replicated to produce the members of the resulting monoclonal population; similarly, a certain number of "errors" and/or incomplete extensions may occur during amplification of the original template, thereby generating a monoclonal or substantially monoclonal population whose individual members can exhibit sequence variability amongst themselves. In some embodiments, a low or insubstantial level of mixing of non-homologous polynucleotides may occur during nucleic acid amplification reactions of the present teachings, and thus a substantially monoclonal population may contain a minority of one or more polynucleotides (e.g., less than 50%, less than 40%, less than 30%, less than 20%, less than 10%, less than 5%, less than 1%, less than 0.5%, less than 0.1%, or less than 0.001%, of diverse polynucleotides). In certain examples, at least 90% of the polynucleotides in the population are at least 90% identical to the original single template used as a basis for amplification to produce the substantially monoclonal population. In certain embodiments, methods for amplifying yield a population of polynucleotides wherein at least 50%, 60%, 70%, 75%, 80%, 85%, 90%, 91%, 92%, 93%, 94%, 95%, 96%, 97%, 98%, 99%, or 100% of the members of a population of polynucleotides share at least 50%, 60%, 70%, 75%, 80%, 85%, 90%, 95%, 96%, 97%, 98%, 99%, or 100% sequence identity to the template nucleic acid from which the population was generated. In certain embodiments, methods for amplifying yield a population of polynucleotides in which a large enough fraction of the polynucleotides share enough sequence identity to allow sequencing of at least a portion of the amplified template using a high-throughput sequencing system.

In some embodiments, at least 50%, 60%, 70%, 75%, 80%, 90%, 95%, or 99%, of the members of the template nucleic acid molecules attached to templated supports will share greater than 90%, 95%, 97%, 99%, or 100% identity with the template nucleic acid molecule. In some embodiments, members of a nucleic acid population which are produced using any of the amplification methods, hybridize to each other under high-stringency hybridization conditions.

In some embodiments, the amplification methods generate a population of substantially monoclonal nucleic acid molecules that includes sufficiently few polyclonal contaminants such that they are successfully sequenced in a high-throughput sequencing method. For example, the amplification methods can generate a population of substantially monoclonal nucleic acid molecules that produces a signal (e.g., a sequencing signal, a nucleotide incorporation signal and the like) that is detected using a particular sequencing system. Optionally, the signal can subsequently be analyzed to correctly determine the sequence and/or base identity of any one or more nucleotides present within any nucleic acid molecule of the population. Examples of suitable sequencing systems for detection and/or analysis of such signals include the Ion Torrent sequencing systems, such as the Ion Torrent PGM™ sequence systems, including the 314, 316 and 318 systems, the Ion Torrent Proton™ sequencing systems, including Proton I, (Thermo Fisher Scientific, Waltham, Mass.) and the Ion Torrent Proton™ sequencing systems, including Ion S5 and S5XL (Thermo Fisher Scientific, Waltham, Mass.). In some embodiments, the monoclonal amplicon permits the accurate sequencing of at least 5 contiguous nucleotide residues on an Ion Torrent sequencing system.

As used herein, the term "clonal amplification" and its variants refer to any process whereby a substantially monoclonal polynucleotide population is produced via amplification of a polynucleotide template. In some embodiments of clonal amplification, two or more polynucleotide templates are amplified to produce at least two substantially monoclonal polynucleotide populations.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Other features and advantages of the present disclosure will be apparent from the following detailed description and from the claims.

DETAILED DESCRIPTION

In some embodiments, the disclosure relates generally to methods, as well as systems, compositions, kits and apparatuses for performing the methods, of manipulating nucleic acids. In some embodiments, the methods include nucleotide polymerization, nucleotide sequence modification (e.g., ligation of adapter and/or primer sequences, such as, for example, cleavable primers), nucleotide modification (e.g., addition of labels or linker molecules (e.g., biotin) to a one or more nucleotides in a nucleic acid molecule), nucleic acid amplification, nucleic acid capture, nucleic acid containment and/or nucleic acid transfer. Methods and compositions provided herein can be used, for example, to generate a monoclonal, or substantially monoclonal, population of nucleic acids. In some embodiments, the methods are used to generate a monoclonal, or substantially monoclonal, population of nucleic acids in which the nucleic acids are attached to a support, such as, for example, a solid support. In some embodiments, the methods are used to attach a nucleic acid to two or more supports. In such embodiments, the two or more supports can be the same or different, including, for example, polymeric and/or magnetic supports. In some embodiments, the methods are used to transfer a nucleic acid attached to one or more supports to a reaction chamber. In some embodiments, the methods are used to generate a monoclonal, or substantially monoclonal, population of nucleic acids within a reaction chamber or multiple reaction chambers. The methods provided herein can be performed alone or in any combination for any one or more uses and provide advantages in the analysis of nucleic acids. For example, use of methods and/or compositions disclosed herein provide for improved quality, quantity and/or accuracy of nucleic acid analysis results, such as, for example, nucleic acid sequencing results. In another example, use of methods and/or compositions disclosed herein alone and/or in any combination enhance nucleic acid manipulation processes to markedly facilitate workflow automation of nucleic acid analysis, such as, for example, nucleic acid sequencing.

In some embodiments, the disclosure relates generally to methods, as well as systems, compositions, kits and apparatuses, that improve high-throughput nucleic acid sequencing results. The methods, systems, compositions, kits and apparatuses incorporate processes and compositions for generating, containing, isolating, transferring, replicating and/or manipulating substantially monoclonal populations of nucleic acids that are rapid, efficient and cost-effective while providing for significantly increased production of high-quality reads of longer length with decreased numbers of duplicate, noninformative and/or bank reads and run times compared to existing methods. In some embodiments, the methods, as well as systems, compositions, kits and apparatuses include supports, e.g., solid supports, to confine, enrich, sequester, isolate, localize, amplify and/or transfer nucleic acids that can be used in analysis methods. In some embodiments, the supports are pre-seeded with one or a limited number of predominantly substantially identical nucleic acids from a large collection of nucleic acids (e.g., a nucleic acid library or sample) to provide an isolated single nucleic acid molecule or localized substantially monoclonal population. Such pre-seeded supports are readily manipulated and used as clean source of identical nucleic acids that can be clonaly amplified, for example, in templating reactions, to generate a relatively pure collection of templates for use in a high-throughput sequencing workflow to improve sequencing results. In some embodiments, the pre-seeded supports can be generated, at least in part, and expanded using isothermal amplification, especially recombinase-mediated amplification reactions such as recombinase-polymerase amplification (RPA). Accordingly, in illustrative aspects of the methods, a pre-seeding reaction is carried out before a templating reaction in a high-throughput sequencing workflow.

In a typical high-throughput sequencing workflow, nucleic acid molecules in a sample are used to prepare a library of template nucleic acid molecules suitable for downstream sequencing. Multiplex amplification can optionally be performed on the nucleic acid molecules before, during, or after library preparation. The library of template nucleic acid molecules is then amplified onto one or more supports to be used in a sequencing reaction. In some embodiments of the present disclosure, the amplification of a template on a solid support typically is performed in two or more reactions, including, for example, one or more pre-seeding reactions that generates one or more pre-seeded supports with substantially monoclonal populations of the template nucleic acid molecules attached, followed by a templating reaction on the pre-seeded supports that generates more copies (e.g., at least 10× more copies) of the attached template nucleic acid molecules on the one or more supports. The advantage of performing a pre-seeding reaction and a templating reaction is that this workflow generates more high-quality sequencing reads in a high-throughput sequencing reaction. In some embodiments, the pre-seeding reaction is performed with blocked primers to prevent the formation of primer dimer amplicons during the pre-seeding reaction. In previous methods, primer dimer amplicons could be generated during templating, which could generate lower quality sequencing reads and a reduction in the quantity of sequencing reads from the template nucleic acid molecules. Therefore, the addition of a separate pre-seeding reaction provides this and significant other advantages over prior methods.

In some embodiments, the disclosure relates generally to methods, as well as systems, compositions, kits and apparatuses for amplifying a template nucleic acid molecule that include a templating reaction mixture using pre-seeded supports. In various aspects, the templated supports are used for downstream sequencing methods. The templating reaction typically uses a recombinase to denature double-stranded template nucleic acid molecules and is carried out at isothermal temperatures with a suitable polymerase for an RPA reaction. In some aspects, the pre-seeded supports are generated in a separate pre-seeding reaction mixture.

Pre-seeding, also referred to herein as seeding, involves the attachment of one or more nucleic acid molecules to a support. In some embodiments, the attachment is designed to generate a single support with a single nucleic acid molecule attached thereto. In some embodiments, the attachment is designed to attach multiple copies of a nucleic acid molecule thereto and/or multiple different nucleic acids thereto. In some embodiments, the attachment is designed to attach a limited number of multiple copies of substantially the same nucleic acid thereto to generate a substantially monoclonal population of nucleic acids.

In some embodiments, a pre-seeding (or seeding) method provided herein includes hybridizing a single-stranded nucleic acid molecule to a complementary nucleic acid, e.g., an oligonucleotide, that is bound to and immobilized on the support. Such methods carried out under annealing conditions over a typically short time period. In some embodiments, the seeding method involves hybridizing under conditions in which the solid support, e.g., a bead, will have only one single-stranded nucleic acid molecule attached to it. Such conditions include contacting a population of single-stranded nucleic acids (e.g., from a library or sample of nucleic acids) with a substantial excess of supports under annealing conditions.

In some embodiments, a pre-seeding (or seeding) method provided herein includes a combined process of attaching a nucleic acid to a support through hybridization and, at the same time, amplifying the attached nucleic acid to a low level, for example, about 20 copies. In these embodiments, the pre-seeding reaction mixture typically includes a population of template nucleic acid molecules, a polymerase, nucleotides, a population of first primers, and a cofactor such as a divalent cation. A skilled artisan will understand that a variety of methods can be used to pre-seed solid supports with substantially monoclonal template nucleic acid molecules. As non-limiting examples, the pre-seeding reaction mixture can be carried out using an RPA reaction, a template walking reaction, PCR, emulsion PCR, or bridge PCR. The pre-seeding reaction and/or the templating reaction can be performed in bulk in a solution. Furthermore, the pre-seeding reaction mixture and/or the templating reaction mixture can include a first universal primer attached to one or more supports, a second universal primer in solution (a soluble second universal primer), and a plurality of template nucleic acid molecules where individual template nucleic acid molecule are joined to at least one universal primer binding sequence(s) which may be added during library preparation, and where the universal primer binding sequence(s) bind the first and optional second universal primer(s). In some embodiments, the pre-seeding reaction and/or the templating reaction is performed in wells. In illustrative examples, the pre-seeding reaction and the templating reaction are carried out using consecutive RPA reactions, wherein template nucleic acid molecules are washed away after the pre-seeding reaction before performing the templating reaction.

Loading supports, e.g., beads, modified with nucleic acid molecules into confined regions or receptacles, such as microwells or dimples, to form an array presents several advantages for nucleic acid sequencing. Placing nucleic acid-coated beads in an organized, tightly packed fashion, for example, into small microwells, can increase throughput per cycle and lower customer cost. As the density of microwells increases or as the microwell size decreases, bead loading becomes difficult, leading to many open microwells and low counts of beads in wells. Too many open microwells provides for a decreased number of base reads and thus, poor sequencing performance. Provided herein, in some embodiments, are methods, as well as systems, compositions, kits and apparatuses for use in the methods, of introducing a support, such as a solid support, e.g., a bead, into a microwell or reaction chamber. In some embodiments, the method includes linking a bead support having a captured template nucleic acid modified with a linker moiety to a magnetic bead having complementary linker moiety to form a bead assembly and loading the bead assembly into a well using a magnetic field. The bead assembly can be denatured to release the magnetic bead, leaving the bead support attached to a target nucleic acid in the well. Such methods can be used, for example, in preparing a device for sequencing of nucleic acids. In an embodiment, reactions carried out in the well can be analytical reactions to identify or determine characteristics or properties of an analyte of interest. Such reactions can generate directly or indirectly byproducts that provide a signal which can indicate if the analyte reacts in a characteristic manner. If such byproducts are produced in small amounts or rapidly decay or react with other constituents, then multiple copies of the same analyte may be analyzed in the well at the same time in order to increase the output signal generated. In an embodiment of methods provided herein, multiple copies of an analyte, e.g., a nucleic acid, may be attached to a solid phase support, either before or after deposition into the well. For example, a target nucleic acid can be amplified in the microwell to provide a clonal population of target nucleic acids useful for sequencing the target nucleic acid. The solid phase support may be, for example, microparticles, nanoparticles, beads, solid or porous comprising gels, or the like. For simplicity and ease of explanation, solid phase supports are also referred to herein as a particle or bead. For a nucleic acid analyte, multiple, connected copies may be made by rolling circle amplification (RCA), exponential RCA, or like techniques, to produce an amplicon without the need of a solid support.

In some embodiments, the disclosure relates generally to methods, as well as systems, compositions, kits and apparatuses for generating one or more templated solid supports, including: a) forming a templating reaction mixture by combining one or more pre-seeded solid supports, nucleotides, a recombinase, and a polymerase, wherein the one or more pre-seeded solid supports include a population of attached substantially identical first primers and have substantially monoclonal template nucleic acid molecules attached thereto, wherein the substantially monoclonal template nucleic acid molecules include a proximal segment including the first primer, wherein the proximal segment attaches a template nucleic acid segment to a solid support at the first primer and wherein the pre-seeded solid supports further include attached first primers that are attached to the pre-seeded solid support and are not bound to template nucleic acid molecules, wherein the templating reaction mixture further includes a population of substantially identical soluble second primers, and wherein the template nucleic acid molecules include a primer binding site for the second primer at or near the terminus opposite the proximal segment; and b) performing a templating reaction by adding a cation to the templating reaction mixture and incubating the reaction mixture under isothermal conditions for at least 10 minutes to amplify the template nucleic acid molecules in a templating reaction to generate one or more templated solid supports. In some embodiments, the method provides templated solid supports wherein each support includes at least 100,000 substantially monoclonal template nucleic acid molecules. Typically, template nucleic acid molecules are not included in solution in the templating reaction mixture. As such, template nucleic acid molecules are typically present in solution in the reaction mixture when the templating reaction is initiated. The pre-seeded solid supports are typically generated in a pre-seeding reaction that is separate from the templating reaction. In some embodiments, template nucleic acids are attached to the solid support by a proximal segment that does not include 100 or more identical nucleotides. In some embodiments, the proximal segment does not include a contiguous sequence of more than 2, 3, 4, 5, 6, 7, 8, 9 or 10 identical nucleotides. In some embodiments of the above aspect, the one or more templated solid supports are used in a sequencing reaction to determine the sequences of the template nucleic acid molecules.

In some embodiments, the disclosure relates generally to methods, as well as systems, compositions, kits and apparatuses, for determining the sequences of template nucleic acid molecules, including: a) generating a population of pre-seeded solid supports including a population of attached substantially identical first primers, wherein the pre-seeded solid supports are generated under pre-seeding conditions and wherein each of the pre-seeded solid supports has between 10 and 100,000 substantially monoclonal template nucleic acid molecules including the first primer attached thereto, and further includes attached first primers that are attached to the pre-seeded solid supports and are not bound to template nucleic acid molecules; b) forming a templating reaction mixture by combining the population of pre-seeded solid supports, nucleotides, a recombinase, and a polymerase; c) initiating a templating reaction by adding a cation to the templating reaction mixture, wherein template nucleic acid molecules are not present in solution in the reaction mixture when the templating reaction is initiated; d) incubating the initiated templating reaction mixture under isothermal conditions for at least 10 minutes to amplify the template molecules in a templating reaction to generate one or more templated solid supports including at least 10 times as many attached substantially monoclonal template nucleic acid molecules on the templated solid supports as were present on the pre-seeded solid supports; and d) sequencing template nucleic acid molecules on the one or more templated solid supports, thereby determining the sequences of template nucleic acid molecules.

In some embodiments, the disclosure relates generally to methods, as well as systems, compositions, kits and apparatuses, for determining the sequences of template nucleic acid molecules, including: a) performing a pre-seeding reaction by incubating a recombinase-polymerase amplification (RPA) reaction mixture including a population of template nucleic acid molecules and a population of solid supports including a population of attached substantially identical first primers under pre-seeding reaction conditions to generate one or more pre-seeded solid supports including substantially monoclonal population of template nucleic acid molecules attached to the solid support by the first primer and attached first primers that are attached to the pre-seeded solid supports and are not bound to template nucleic acid molecules, wherein the pre-seeding reaction conditions include incubating the RPA reaction mixture under isothermal conditions, wherein the pre-seeded solid supports each have between 10 and 100,000 substantially monoclonal nucleic acid molecules attached thereto and/or the pre-seeding reaction conditions include incubating the RPA reaction mixture for 2 to 5 minutes under isothermal conditions; b) forming a templating reaction mixture by including the one or more pre-seeded solid supports in an RPA reaction mixture, wherein template nucleic acid molecules not associated with the pre-seeded solid supports are not included in the templating reaction mixture; c) initiating a templating reaction by adding a cation to the templating reaction mixture; d) incubating the initiated templating reaction mixture under isothermal conditions for at least 10 minutes to amplify the template nucleic acid molecules in a templating reaction to generate one or more templated solid supports including at least 10 times as many substantially monoclonal template nucleic acid molecules on the templated solid supports as were present on the pre-seeded solid supports; and e) sequencing the template nucleic acid molecules on the one or more templated solid supports, thereby determining the sequence of a template nucleic acid molecule.

In some embodiments, the plurality of template nucleic acid molecules includes two or more template nucleic acid molecules with different sequences. In some embodiments, the substantially monoclonal template nucleic acid molecules, which are attached to a pre-seeded solid support and/or are attached to a templated solid support, include template nucleic acid molecules having two or more different sequences. The substantially monoclonal template nucleic acid molecules typically are attached to a solid support by a primer that can include consecutive identical nucleotides, or no consecutive identical nucleotides or no more than 2, 3, 4, 5, 6, 7, 8, 9 or 10 consecutive nucleotides or by a primer that includes consecutive non-identical nucleotides. However, the proximal segment of a template nucleic acid which is the segment attached to a solid support and is typically a primer, includes fewer than 100 identical nucleotides. In some embodiments, the templated solid supports are templated beads and the sequencing includes distributing the beads in wells of a solid support before a sequencing reaction is performed. Each pre-seeded solid support of the population of solid supports, in illustrative examples, can have, for example, between 10 and 50,000 or between 100 and 25,000 substantially monoclonal template nucleic acid molecules attached thereto. In illustrative example, the pre-seeding reaction mixture and/or the templating reaction mixture further include a population of identical second primers in solution. In these examples, the template nucleic acid molecules typically include a primer binding site for the first primer at or near a first terminus and a primer bind site for the second primer at or near the other terminus.

In another aspect, the templating reaction mixture including a population of pre-seeded solid supports, nucleotides, a recombinase, and a polymerase, wherein the population of pre-seeded solid supports have between 10 and 50,000 substantially monoclonal template nucleic acid molecules including a first primer attached thereto and further include attached first primers not bound to template nucleic acid molecules, wherein the reaction mixture does not include a cation capable of initiating a recombinase-polymerase amplification reaction, and wherein at least 75%, 80%, 85%, 90%, 95%, 98%, 99%, or 99.9% of the template nucleic acid molecules in the reaction mixture are attached to the one or more solid supports.

In some embodiments, the one or more pre-seeded supports are formed during a pre-seeding reaction using a pre-seeding reaction mixture. In some embodiments, the pre-seeding reaction mixture includes some or all of the following: a population of template nucleic acid molecules, one or more supports, a polymerase, a population of first primers, nucleotides, and a divalent cation. In some embodiments, the population of first primers is attached to the one or more supports. In any of the embodiments of the present teachings, the pre-seeding reaction mixture further includes a second primer and optionally a diffusion-limiting agent. In illustrative embodiments, the second primer is in solution. In illustrative embodiments, the pre-seeding reaction mixture includes a recombinase and optionally a recombinase accessory protein.

Figure 4:
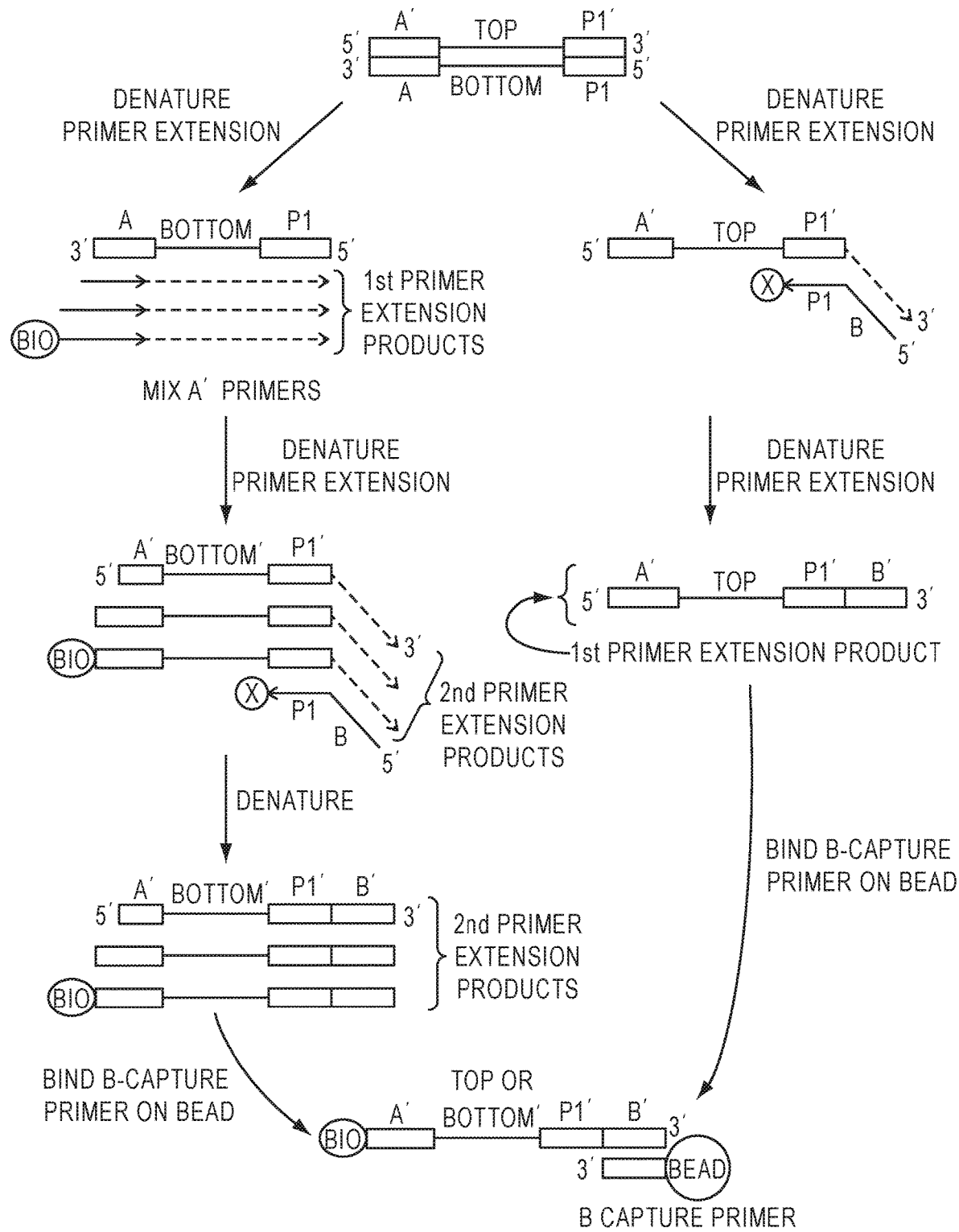
FIG. 4 is a schematic showing primer extension reactions for the top and bottom strands of a template nucleic acid molecule.

In some embodiments, the pre-seeding and/or the templating reaction(s) are conducted by employing nucleic acid amplification using (i) a plurality of nucleic acid molecules which include a target sequence and one or more universal adaptor sequences, (ii) a plurality of soluble forward primers, (iii) a plurality of soluble reverse blocked tailed primers, and (iv) a plurality of solid supports having immobilized thereon capture primers that hybridize to a universal adaptor sequence. In some embodiments, the pre-seeding and/or templating reactions are conducted in a single reaction mixture with a plurality of nucleic acid molecules having the same or different target sequences. In some embodiments, individual nucleic acid molecules generated from a sample include a target sequence joined at the ends to at least one universal adaptor sequence (e.g., an A-adaptor and/or P1-adaptor sequences). In some embodiments, the nucleic acid molecules are double-stranded molecules having complementary top and bottom strands. In some embodiments, the pre-seeding reaction is conducted to amplify and attach substantially monoclonal copies of a nucleic acid molecule to a solid support using forward and reverse soluble primers that hybridize to the adaptor sequences (see FIG. 4). Although FIG. 4 depicts a series of reactions for a single double-stranded nucleic acid molecule and a single bead within a single reaction mixture, it will be appreciated by the skilled artisan that the same single reaction mixture contains a plurality of double-stranded nucleic acid molecules and a plurality of beads that are undergoing the same series of reactions to generate at least two beads each attached with a substantially monoclonal population of target sequences. Additionally, the skilled artisan will appreciate that the bead can be attached a plurality of B capture primers. Further, the bottom of FIG. 4 depicts a biotinylated primer extension product that binds to a B capture primer, but it will be appreciated by the skilled artisan that a non-biotinylated primer extension product can bind a B capture primer. It will also be appreciated by the skilled artisan that a mixture of biotinylated and non-biotinylated primer extension products can be attached to the plurality of B capture primers that are attached to the bead. In some embodiments, the single reaction mixture contains a plurality of nucleic acid molecules, wherein individual nucleic acid molecules having the same or different target sequences are attached to at least one universal adaptor sequence. Referring now to FIG. 4, the nucleic acid molecules, having top and bottom strands, is denatured and the separated top and bottom strands is used in primer extension reactions using soluble primers (e.g., soluble A primers) and soluble blocked tailed primers (e.g., soluble blocked tailed P1/B primers), to generate a plurality of primer extension products having adapter sequences that can bind an immobilized B primer during the pre-seeding and/or templating reactions. As shown in FIG. 4, the primer extension reactions generate different products for the two strands due to the different sequences and orientations of the top and bottom strands and differences in the primers used.

In some embodiments, in a first primer extension reaction, a complementary strand of the bottom strand is generated using a soluble primer that binds the A primer binding site. For illustration purposes in FIG. 4 (left) the soluble A' primer is complementary to the A adaptor sequence. In some embodiments, a mixture of varying length soluble A' primers is used for the first primer extension reaction. The mixture of soluble A' primers can vary in length at their 5' ends, 3' ends, or both 5' and 3' ends. For example, Primer Mix S (a mix of A' primers that can include various lengths of a 5' non-complementary sequence with or without a 5' biotin adduct (depicted as "Bio" in FIG. 4), and can be used in the primer extension reaction to generate one of several possible first extension products depending on which soluble A' primer is used for the first primer extension reaction (FIG. 4, left). For example, the first extension products contain, in a 5' to 3' direction, a complementary A-adaptor sequence (shown as A' in FIG. 4, left), a complementary bottom sequence (shown as bottom' in FIG. 4, left), and a complementary P1 sequence (shown as P1' in FIG. 4, left). In some embodiments, in a second primer extension reaction, the newly synthesized P1' sequence in the first extension product can bind to a soluble P1 primer to allow primer extension to occur from the 3' end of the P1' sequence of the first primer extension product. The soluble P1 primer can be a tailed primer. The soluble P1 primer can carry a blocking moiety at its 3' end, wherein the blocking moiety can inhibit primer extension from the 3' end of the primer. The soluble P1 primer can be a reverse tailed P1 primer which includes an attached 5' B adapter sequence such that primer extension of the first extension product, using the tailed primer P1 as a template results in the addition of the complement of the B sequence (depicted as B' in FIG. 4 left) to the 3' end. In illustrative embodiments, the soluble P1 primer can have a 3' blocked end (shown as an encircled "X" in FIG. 4, left) to prevent extension from the 3' end of the soluble P1 primer (FIG. 4, left). The second primer extension reaction can generate a plurality of second extension products having various lengths, depending on which soluble A' primer was used in the first extension reaction. The plurality of second extension products contain, in a 5' to 3' direction, a complementary A-adaptor sequence (shown as A' in FIG. 4, left), a complementary bottom strand sequence (shown as bottom' in FIG. 4, left), a complementary P1 sequence (shown as P1' in FIG. 4, left), and a complementary B adaptor sequence (shown as B' in FIG. 4, left). The second primer extension products can include or lack a 5' biotin adduct (FIG. 4, left). The second extension reaction can generate a plurality of second extension products having different lengths, and which can include or lack a biotin adduct, and which include a B' adaptor sequence. Any of these second extension products can bind/hybridize to the B capture sequence which is immobilized to the solid surface (bead). The immobilized B primer can undergo a third primer extension reaction, thereby generating a third extension product which is immobilized to the bead, and is complementary to the second extension product (FIG. 4, bottom).

Referring now to FIG. 4 (right) which depicts the double-stranded nucleic acid undergoing denaturation, and a series of reactions for the top strand. In some embodiments, the P1' adaptor sequence of the top strand can bind the soluble P1 primer and undergo a first primer extension reaction to generate a first extension product (FIG. 4, right). In some embodiments, the soluble P1 primer is a tailed primer. The soluble P1 primer can carry a blocking moiety at its 3' end, wherein the blocking moiety can inhibit primer extension from the 3' end of the primer (FIG. 4, right). The soluble P1 primer can be a tailed P1 primer which includes an attached 5' B adapter sequence such that primer extension, using the tailed primer P1 as a template, results in the addition of the complement of the B sequence (B') to the 3' end of the first extension product (FIG. 4, right). In illustrative embodiments, the soluble P1 primer can have a 3' blocked end (shown as an encircled "X" in FIG. 4, right) to prevent extension from the 3' end of the P1 primer (FIG. 4, right). The first primer extension reaction generates a plurality of first extension products which contain, in a 5' to 3' direction, an A' adaptor sequence, a top strand sequence, a P1' adaptor sequence, and a B' adaptor sequence (FIG. 4, right). The first extension product, which includes a B' adaptor sequence, can bind/hybridize to the B capture sequence which is immobilized to the solid surface (bead). The immobilized B primer can undergo a second primer extension reaction, thereby generating a second extension product which is immobilized to the bead, and is complementary to the first extension product (FIG. 4, bottom).

Figure 5:
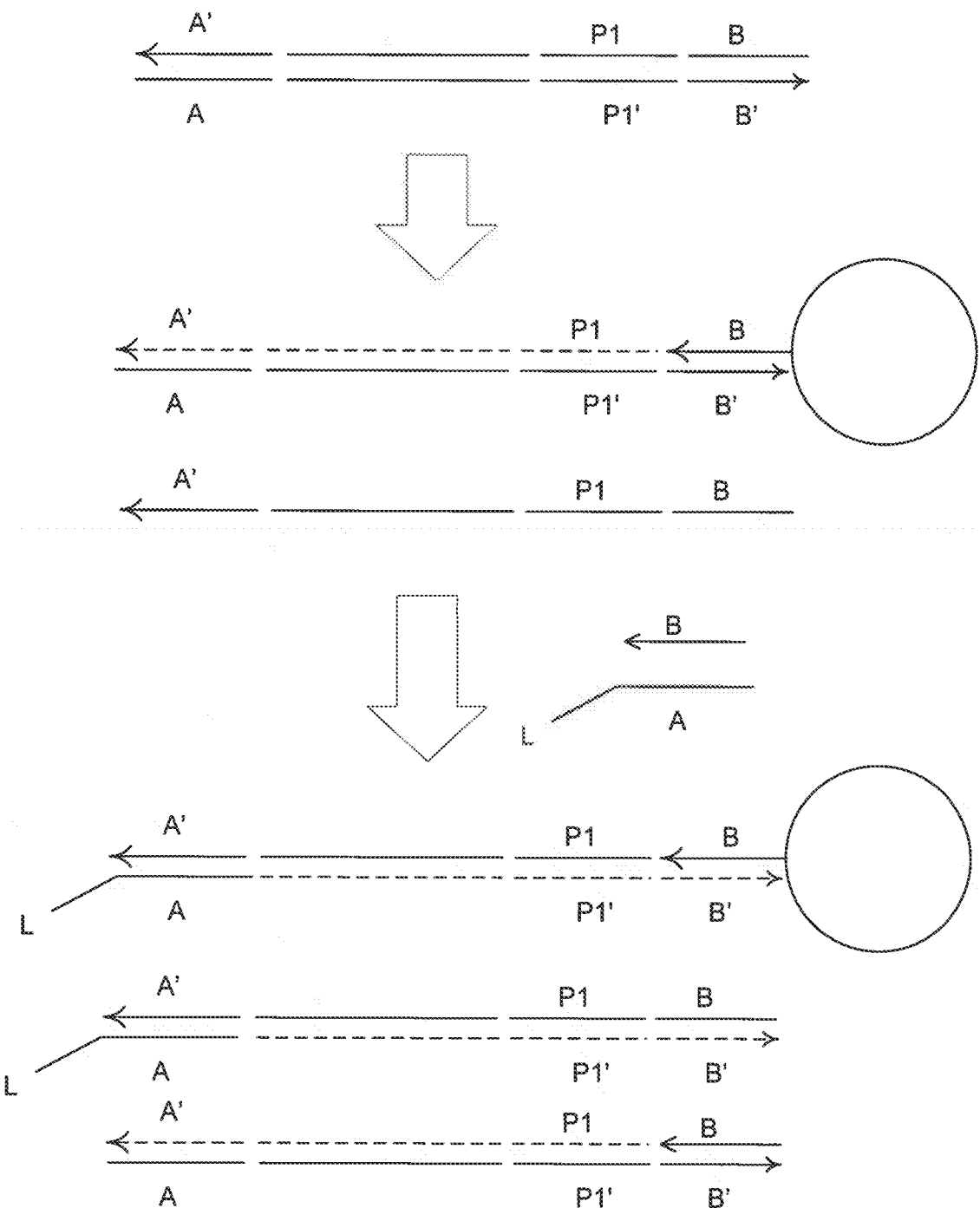
FIG. 5, FIG. 6, and FIG. 7 illustrate example schema for attaching nucleic acids to a bead.

In some embodiments, a pre-seeding (or seeding) reaction can be performed as illustrated in FIG. 5. In this example, a target polynucleotide B-A' and its complement, a template polynucleotide (A-B'), are amplified in the presence of a bead support having a capture primer. The target polynucleotide has a capture portion (B) the same as or substantially similar to a sequence of the capture primer coupled to the bead support. Substantially similar sequences are sequences whose complements can hybridize to each of the substantially similar sequences. The bead support can have a capture primer that is the same sequence or a sequence substantially similar to that of the B portion of the target polynucleotide to permit hybridization of the complement of the capture portion (B) of the target polynucleotide with the capture primer attached to the bead support. Optionally, the target polynucleotide can include a second primer location (P1) adjacent to the capture portion (B) of the target polynucleotide and can further include a target region adjacent the primers and bounded by complement portion (A') to a sequencing primer portion (A) of the target polynucleotide. When amplified in the presence of the bead support including a capture primer, the template polynucleotide complementary to the target polynucleotide can hybridize with the capture primer (B). The target polynucleotide can remain in solution. The system can undergo an extension in which the capture primer B is extended complementary to the template polynucleotide yielding a target sequence bound to the bead support. A further amplification can be performed in the presence of a free primer (B), the bead support, and a free modified sequencing primer (A) a having a linker moiety (L) attached thereto. The primer (B) and the modified primer (L-A) can interfere with the free floating target polynucleotide and template polynucleotide, hindering them from binding to the bead support and each other. In particular, the modified sequencing primer (A) having the linker moiety attached thereto can hybridize with the complementary portion (A') of the target polynucleotide attached to the bead support. Optionally, the linker modified sequencing primer L-A hybridized to the target polynucleotide can be extended forming a linker modified template polynucleotide. Such linker modified template polynucleotide hybridize to the target nucleic acid attached to the bead support can then be captured by a magnetic bead and used for magnetic loading of the sequencing device. The amplification or extensions can be performed using polymerase chain reaction (PCR) amplification, recombinase polymerase amplification (RPA), or other amplification techniques. In a particular example, each step of the scheme illustrated in FIG. 5 is performed using PCR amplification.

Figure 6:
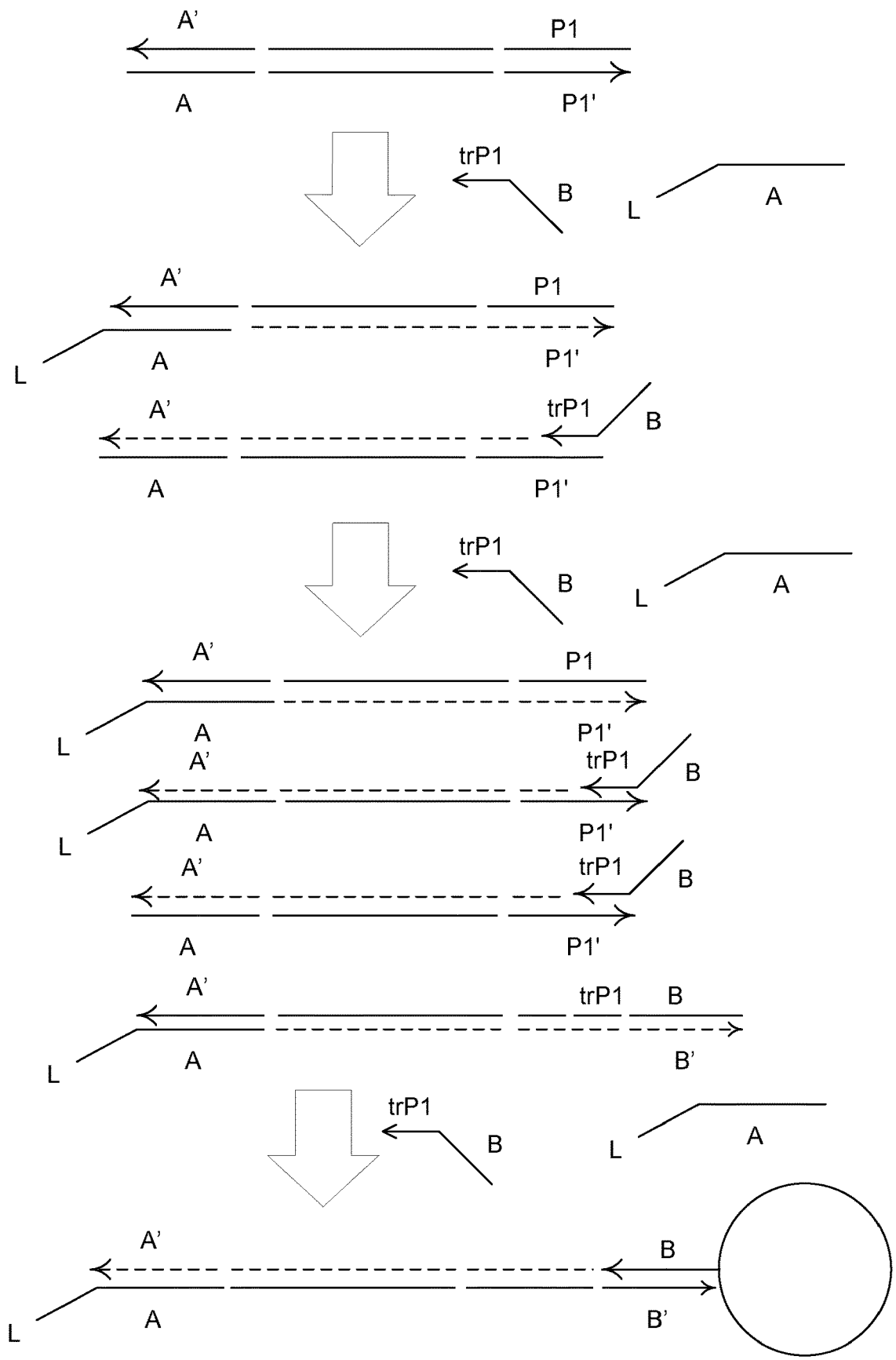

In some embodiments, a pre-seeding (or seeding) reaction can be performed as illustrated in FIG. 6. In this example, an alternative scheme includes a target polynucleotide (P1-A') and its complement template polynucleotide (A-P1'). The target polynucleotide and template polynucleotide are amplified in a solution including a linker modified sequencing primer (L-A) and a truncated P1 primer (trP1) having a portion having the sequence of the capture primer (B). In an example, the truncated P1 primer (trP1) includes a subset of the sequence of P1 or all of the sequence P1. During subsequent amplifications in the presence of the linker modified sequencing primer (L-A) and truncated P1 primer (trP1-B), a single species 702 includes a linker modified template polynucleotide (L-A-B') operable to hybridize with a bead support having a capture primer (B). Accordingly, the linker modified template polynucleotide (L-A-B') hybridizes with the capture primer (B) on the bead and is extended to form a target polynucleotide (B-A') attached to the bead support. The linker modified template polynucleotide hybridized to the target polynucleotide attached bead can be utilized to attach to a magnetic bead, which, for example, can be used to implement magnetic loading of the bead into a sequencing device and/or for enriching the nucleic acids attached to the bead. The linker moiety of the linker modified template polynucleotide can take various forms, such as biotin, which can bind to linker moieties attached to the magnetic bead, such as streptavidin. Each of the amplification reactions can be undertaken using PCR, RPA, or other amplification techniques. In the example illustrated in FIG. 6, the scheme can be implemented using three cycles of polymerase chain reaction (PCR). Such a series of PCR reactions results in a greater percentage of bead supports having a single target polynucleotide attached thereto. As a result, more monoclonal populations can be generated in wells in the sequencing device.

Figure 7:
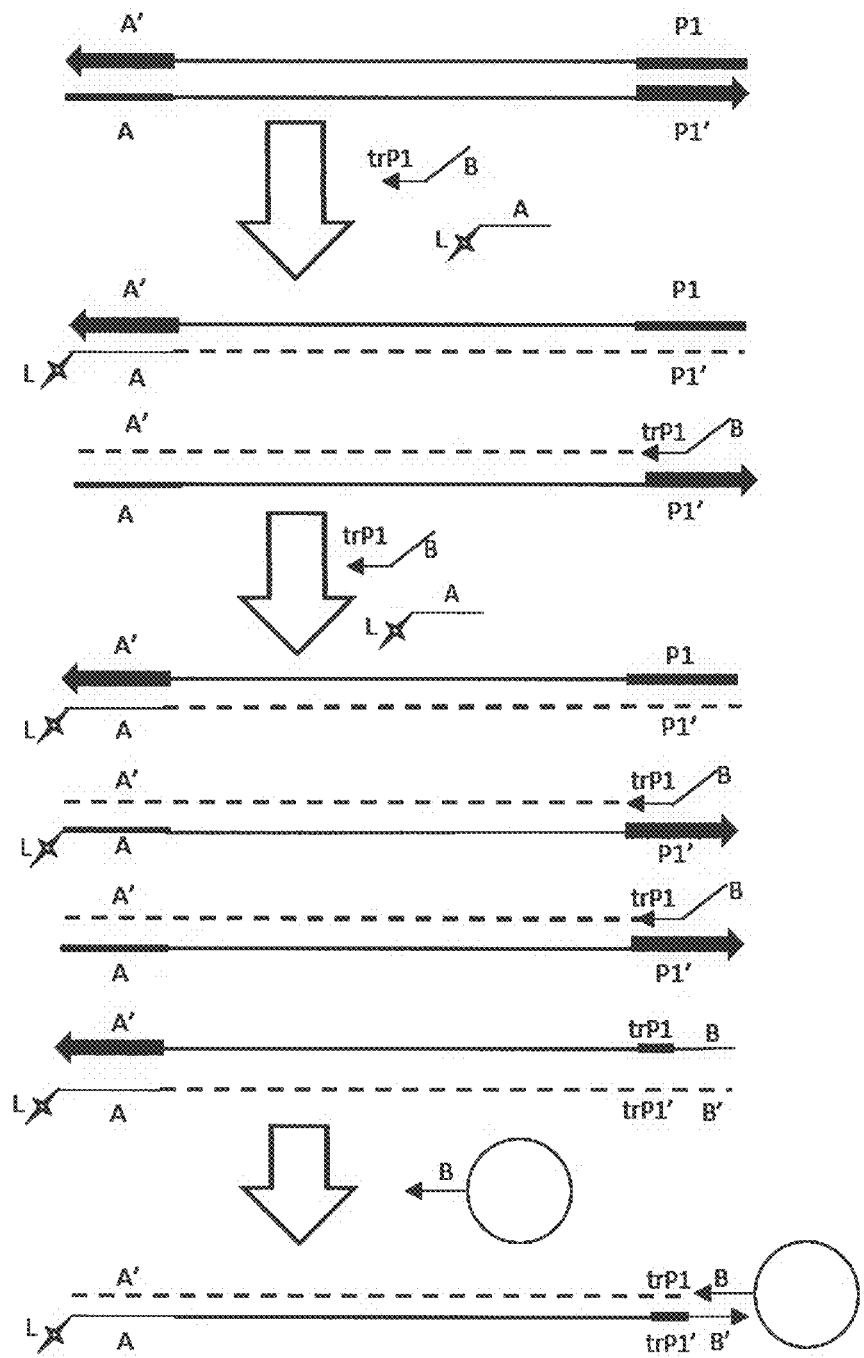

In some embodiments, a pre-seeding (or seeding) reaction can be performed as illustrated in FIG. 7. In this example, the reaction is designed to generate a desired bead-attached nucleic acid molecule from a series of amplification cycles in which only one of the amplification products, which is the desired target nucleic acid, will attach to the bead. The desired target contains a linker moiety, e.g., biotin, (labeled with the letter "L" in FIG. 7) attached to the 5' end of the nucleic acid and an adapter nucleotide sequence (labeled with the letter "B'" in FIG. 7) at the 3' end that is complementary to the primer (labeled with the letter "B" in FIG. 7) immobilized on the bead. In contrast, the method shown in FIG. 6 generates two nucleic acid amplification products that hybridize to the bead, only one of which has the desired linker moiety. In generating only one amplification product that will attach to the bead, this method avoids the production of beads that do not contain the desired target nucleic acid, for example, one lacking linker moiety, which would not be used in downstream analyses. Thus, this method avoids waste of beads and nucleic acids and ensures that only a single nucleic acid target molecule will hybridize to a bead which is desirable to maintain a high level of monoclonality in subsequent templating amplifications using the beads that have only one nucleic acid template bound thereto. As shown in FIG. 7, the double-stranded library nucleic acids contain an A adapter sequence at the 5' end and a P1 adapter sequence at the 3' end (standard Ion Torrent A and P1 library adapters; Thermo Fisher Scientific). The primers used in the amplification are a biotinylated primer A (forward primer) and reverse primer that is a fusion of trP1 and B primers (trP1 is a 23mer segment of the Ion P1 adapter with sequence CCT CTC TAT GGG CAG TCG GTG AT; SEQ ID NO: 1). The B primer sequence is identical to the sequence of the B primer immobilized on the bead. The trP1-B fusion primer will hybridize and prime at the inner portion of the P1 adapter sequence of the library nucleic acid molecules, close to the library insert sequence and does not hybridize at with the remainder of the P1 adapter sequence at the extreme 3' end of the library nucleic acids. This forms a mismatch end between the trP1-B primer sequence and the very 3' end portion of the P1 adapter on the library nucleic acids. As shown in FIG. 7, after two cycles of amplification (e.g., PCR), although four amplification products are generated, only one product will be able to seed (or hybridize) to the bead (e.g., an Ion Sphere Particle). Thus, upon subsequent denaturation of the amplification products, a single-strand of only one of the products will hybridize to the B primer on the bead. This primer can be extended to form a double-stranded template nucleic acid in which one strand contains a linker moiety that can be used, for example, to bind the bead-bound nucleic acid to a magnetic bead for use in enrichment and/or magnetic loading of wells.

In some embodiments, after conducting the pre-seeding and/or templating reactions using the soluble blocked tailed P1/B primers (e.g., as depicted in FIG. 4), streptavidin beads are used to enrich beads which are attached with target nucleic acid molecules carrying a biotin adduct. In some embodiments, the beads (enriched or not) that are attached to target nucleic acids and generated according to the series of reactions depicted in FIG. 4 are sequenced, for example in a massively parallel sequencing reaction. In some embodiments, the beads (enriched or not) that are attached with target nucleic acid molecules are deposited on an array of reaction chambers which are coupled to field effect transistors (FET) or ion-sensitive field effect sensors (ISFE), and the target nucleic acid molecules are sequenced.

In some embodiments, the template nucleic acid molecules are derived from a sample that is from a natural or non-natural source. In some embodiments, the nucleic acid molecules in the sample are derived from a living organism or a cell. Any nucleic acid molecule can be used, for example, the sample can include genomic DNA covering a portion of or an entire genome, mRNA, or miRNA from the living organism or cell. In other embodiments, the template nucleic acid molecules are synthetic or recombinant. In some embodiments, the sample contains nucleic acid molecules having substantially identical sequences or having a mixture of different sequences. Illustrative embodiments are typically performed using nucleic acid molecules that were generated within and by a living cell. Such nucleic acid molecules are typically isolated directly from a natural source such as a cell or a bodily fluid without any in vitro amplification. Accordingly, the sample nucleic acid molecules are used directly in subsequent steps. In some embodiments, the nucleic acid molecules in the sample can include two or more nucleic acid molecules with different sequences.

A variety of methods are known in the art to prepare template nucleic acid molecules from a sample and can be used in any of the aspects of the pre-seeding and/or templating methods, as well as systems, compositions, kits and/or apparatuses. In some embodiments, the nucleic acid molecules are present in the sample as fragments or unfragmented. In any of the disclosed embodiments, the nucleic acid molecules in the sample are fragmented or further fragmented to generate nucleic acid molecules of any chosen length before being used in the pre-seeding reaction. A skilled artisan will recognize methods for performing such fragmentation to obtain fragments within a range of chosen lengths. For example, the nucleic acid molecules can be fragmented using physical methods such as sonication, enzymatic methods such as digestion by DNase I or restriction endonucleases, or chemical methods such as applying heat in the presence of a divalent metal cation. In some embodiments, the nucleic acid molecules in the sample are fragmented to generate nucleic acid molecules of any chosen length. A skilled artisan will recognize methods for performing such fragmentation to achieve a range of chosen lengths. In other embodiments, nucleic acid fragments within a range of chosen lengths are selected using methods known in the art. In some aspects, nucleic acid molecules or nucleic acid fragments are selected for specific size ranges using methods known in the art. In some embodiments, the nucleic acid molecules or fragments are between about 2 and 10,000 nucleotides in length, for example between about 2 and 5,000 nucleotides, between about 2 and 3,000 nucleotides, or between about 2 and 2,000 nucleotides in length.

In some embodiments, the disclosure relates generally to methods, as well as systems, compositions, kits and apparatuses, the nucleic acid molecules from the sample are used as part of a high-throughput sequencing workflow, such as to generate a library of template nucleic acid molecules. In some embodiments, a population of different template nucleic acid molecules amplified using any of the amplification methods of the present teachings include a library of template nucleic acid molecules having a nucleic acid adapter sequence on one or both ends. For example, the template nucleic acid molecules in the library can include a first and second end, where the first end is joined to a first nucleic acid adapter. The template nucleic acid molecules in the library can also include a second end joined to a second nucleic acid adapter. The first and second nucleic acid adapters can be ligated or otherwise introduced to the template nucleic acid molecules. The adapter can be ligated or otherwise introduced to an end of a linear template, or within the body of a linear or circular template nucleic acid molecule. Optionally, the template nucleic acid molecule can be circularized after the adapter is ligated or introduced. In some embodiments, a first adapter is ligated or introduced at a first end of a linear template and a second adapter is ligated or introduced at a second end of the template. The first and second adapters can have the same or different sequences. The first and second adapters can have primer binding sequences that are the same or different. In some embodiments, at least a portion of the first or second nucleic acid adapter (i.e., as part of the template nucleic acid molecules in the library) can hybridize to the first primer, which is a universal primer.

The nucleic acid molecules can have 5' and/or 3' overhangs that can be repaired before further library preparation. In illustrative embodiments, the template nucleic acid molecules with 5' and 3' overhangs are repaired to generate blunt-ended sample nucleic acid molecules using methods known in the art. For example, in an appropriate buffer the polymerase and exonuclease activities of the Klenow Large Fragment Polymerase can be used to fill in 5' overhangs and remove 3' overhangs on the nucleic acid molecules. In some embodiments, a phosphate is added on the 5' end of the repaired nucleic acid molecules using Polynucleotide Kinase (PNK) and reaction conditions a skilled artisan will understand. In further illustrative embodiments, a single nucleotide or multiple nucleotides is added to one strand of a double stranded molecule to generate a "sticky end." For example, an adenosine (A) can be appended on the 3' ends of the nucleic acid molecules (A-tailing). In some embodiments, other sticky ends are used other than an A overhang. In some embodiments, other adapters are added, for example looped ligation adapters. In some embodiments, adapters are added during a PCR step. In any of the embodiments of the present teachings, none, all, or any combination of these modifications are carried out. Many kits and methods are known in the art for generating populations of templates nucleic acid molecules for subsequent sequencing. Such kits would typically be modified to include adapters that are customized for the amplification and sequencing steps of the methods and compositions of the present teachings. Adapter ligation can also be performed using commercially available kits such as the ligation kit found in the Agilent SureSelect kit (Agilent).

In some embodiments, the amplification methods optionally include a target enrichment step before, during, or after the library preparation and before a pre-seeding reaction. Target nucleic acid molecules, including target loci or regions of interest, can be enriched, for example, through multiplex nucleic acid amplification or hybridization. A variety of methods are known in the art to perform multiplex nucleic acid amplification to generate amplicons, such as multiplex PCR, and can be used in any of the embodiments of the present teachings. Enrichment by any method can be followed by a universal amplification reaction before the template nucleic acid molecules are added to a pre-seeding reaction mixture. Any of the embodiments of the present teachings include enriching a plurality of at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 target nucleic acid molecules, target loci, or regions of interest. In any of the disclosed embodiments, the target loci or regions of interest are at least 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, 500, 600, 700, 800, 900, or 1,000 nucleotides in length and include a portion of or the entirety of the template nucleic acid molecule. In other embodiments, the target loci or regions of interest are between about 1 and 10,000 nucleotides in length, for example between about 2 and 5,000 nucleotides, between about 2 and 3,000 nucleotides, or between about 2 and 2,000 nucleotides in length. In any of the embodiments of the present teachings, the multiplex nucleic acid amplification includes generating at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 copies of each target nucleic acid molecule, target locus, or region of interest. In any of the disclosed embodiments, methods, as well as related compositions, systems, kits, and apparatuses, for pre-seeding, include generating a population of pre-seeded solid supports using the amplicons from the multiplex nucleic acid amplification in a pre-seeding reaction.

In some embodiments, after the library preparation and optional enrichment step, the library of template nucleic acid molecules is templated onto one or more supports. In the present disclosure, the one or more supports are typically templated in two reactions, a pre-seeding reaction to generate pre-seeded solid supports and a templating reaction using the one or more pre-seeded supports to further amplify the attached template nucleic acid molecules. The pre-seeding reaction is typically an amplification reaction and can be performed using a variety of methods a skilled artisan will understand. For example, the pre-seeding reaction can be performed in an RPA reaction, a template walking reaction, or a PCR. In an RPA reaction, template nucleic acid molecules are amplified using a recombinase, polymerase, and optionally a recombinase accessory protein in the presence of primers and nucleotides. The recombinase and optionally the recombinase accessory protein can dissociate at least a portion of a double-stranded template nucleic acid molecules to allow primers to hybridize that the polymerase can then bind to initiate replication. In some embodiments, the recombinase accessory protein is a single-stranded binding protein (SSB) that prevents the re-hybridization of dissociated template nucleic acid molecules. Typically, RPA reactions are performed at isothermal temperatures. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are dissociated by thermal cycling. After cooling, primers bind to complementary sequences and can be used for replication by the polymerase. In any of the aspects of the present teachings, the pre-seeding reaction is performed in a pre-seeding reaction mixture, which is formed with the components necessary for amplification of the template nucleic acid molecules. In any of the disclosed aspects, the pre-seeding reaction mixture includes some or all of the following: a population of template nucleic acid molecules, a polymerase, one or more solid supports with a population of attached first primers, nucleotides, and a cofactor such as a divalent cation. In some embodiments, the pre-seeding reaction mixture further includes a second primer and optionally a diffusion-limiting agent. In some embodiments, the population of template nucleic acid molecules comprise template nucleic acid molecules joined to at least one adaptor sequence which hybridize to the first or second primers. In some embodiments, the reaction mixture forms an emulsion, as in emulsion RPA or emulsion PCR. In pre-seeding reactions carried out by RPA reactions, the pre-seeding reaction mixture includes a recombinase and optionally a recombinase accessory protein. The various components of the reaction mixture are discussed in further detail herein.

In some embodiments, the pre-seeding reaction mixtures include a population of template nucleic acid molecules that is typically derived from the library preparation or target enrichment. In some embodiments, template nucleic acid molecules or populations of template nucleic acid molecules are at least some, and typically all members of a library of template nucleic acid molecules. In some embodiments, the pre-seeding reaction mixture includes at least one template nucleic acid molecule. In some embodiments, the pre-seeding reaction mixture includes at least two template nucleic acid molecules with different sequences. In illustrative embodiments, the pre-seeding reaction mixture includes a population of template nucleic acid molecules with different sequences. In some embodiments, the pre-seeding reaction mixture includes a population of substantially monoclonal template nucleic acid molecules. In any of the embodiments of the present teachings, the template nucleic acid molecules are polynucleotides as they are alternatively referred to herein (the template nucleic acid molecules are interchangeably referred to herein as a template or a nucleic acid template or a polynucleotide template). In various embodiments, the template nucleic acid molecules are polymers of deoxyribonucleotides, ribonucleotides, and/or analogs thereof. In some embodiments, the polynucleotides are naturally-occurring, synthetic, recombinant, cloned, amplified, unamplified, or archived (e.g., preserved) forms. In some embodiments, the polynucleotides are DNA, cDNA, RNA, or chimeric RNA/DNA, and nucleic acid analogs.

The template nucleic acid molecule to be amplified can be double-stranded, or is rendered at least partially double-stranded using appropriate procedures prior to the pre-seeding reaction. In some embodiments, the template is linear. Alternatively, the template can be circular or include a combination of linear and circular regions. In some embodiments, the amplifying includes forming a partially denatured template. For example, the amplification can include partially denaturing a double-stranded template nucleic acid molecule. Optionally, partially denaturing includes subjecting the double-stranded template nucleic acid molecule to partially denaturing conditions. In some embodiments, the partially denatured template includes a single-stranded portion and a double-stranded portion. In some embodiments, the single-stranded portion includes the first primer binding sequence. In some embodiments, the single-stranded portion includes the second primer binding sequence. In some embodiments, the single-stranded portion includes both the first primer binding sequence and the second primer binding sequence.

Optionally, the double-stranded template nucleic acid molecule includes a forward strand. The double-stranded template nucleic acid molecule can further include a reverse strand. The forward strand optionally includes a first primer binding sequence. The reverse strand optionally includes a second primer binding sequence. The primer binding sequences are typically attached during the library preparation as disclosed above. In some embodiments, the template nucleic acid molecule already includes a first primer binding sequence and optionally a second primer binding sequence. Alternatively, the template nucleic acid molecule optionally does not originally include a primer binding sequence, and the library preparation can optionally include attaching or introducing a primer binding sequence to the template as disclosed above.

In some embodiments, the template nucleic acid molecules include single-stranded or double-stranded polynucleotides, or a mixture of both. In some embodiments, the template nucleic acid molecules include polynucleotides with the same or different nucleotide sequences. In some embodiments, the template nucleic acid molecules include polynucleotides having the same or different lengths. In various embodiments, the pre-seeding reaction mixture includes between about 2 and $10^{12}$ different template nucleic acid molecules, for example between about 2 and $10^{11}$ different template nucleic acid molecules, between about 2 and $10^{10}$ different template nucleic acid molecules, between about 2 and $10^9$ different template nucleic acid molecules, between about 2 and $10^8$ different template nucleic acid molecules, between about 2 and $10^7$ different template nucleic acid molecules, between about 2 and $10^6$ different template nucleic acid molecules, or between about 2 and 500,000 different template nucleic acid molecules. In any of the disclosed embodiments, the reaction mixture includes between $5\times10^6$ and $10^{10}$ solid supports. The solid supports can have a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). In any of the embodiments of the present teachings, the volumes of the pre-seeding reaction mixtures and/or templating reaction mixtures are between about 50 and 2,000 µl, for example between about 50 and 1,500 µl, between about 50 and 1,000 µl, between about 50 and 500 µl, between about 50 and 250 µl, or between about 50 and 150 µl.

The pre-seeding reaction is performed to generate one or more pre-seeded supports. Accordingly, in any of the disclosed aspects, the pre-seeding reaction mixture can include one or more solid or semi-solid supports to which the template nucleic acid molecules are attached. As used herein, solid or semi-solid supports can also refer to one support with sites of attachment that can be distinctly analyzed in downstream sequencing methods. In illustrative embodiments, the one or more supports include a population of attached substantially identical first primers. In some embodiments, at least one template nucleic acid molecule in the reaction mixture includes a first primer binding sequence. The first primer binding sequence can be substantially identical or substantially complementary to the sequence of the first primer. In some embodiments, at least one, some, or all of the supports include a population of first primers that are substantially identical to each other. In some embodiments, all of the primers on the supports are substantially identical to each other or all include a substantially identical first primer sequence. In some embodiments, at least one of the supports includes two or more different primers attached thereto. For example, the at least one support can include a population of a first primer and a population of a second primer. The support can be attached to a universal primer. The universal primer optionally hybridizes (or is capable of hybridizing) to all, or substantially all, of the template nucleic acid molecules within the reaction mixture. The reaction mixture can include a first support covalently attached to a first target-specific primer and a second support covalently attached to a second target-specific primer, wherein the first and second target-specific primers are different from each other. Optionally, the first target-specific primer is substantially complementary to a first target nucleic acid sequence and the second target-specific primer is substantially complementary to a second target nucleic acid sequence, and wherein the first and second target nucleic acid sequences are different.

In some embodiments, two or more different template nucleic acid molecules having a first primer binding sequence are included in the pre-seeding reaction mixture. In some embodiments, the at least two different template nucleic acid molecules are amplified directly onto a support such as a site on a support that includes a plurality of sites, a bead or microparticle, or a reaction chamber of an array. The template nucleic acid molecules can be pre-seeded in bulk in solution and then distributed into an array of wells or reaction sites on a solid support. Alternatively, solid supports can be distributed into an array of wells and template nucleic acid molecules can be pre-seeded on the solid supports while they are held in place in an array of wells. In some embodiments, methods for nucleic acid amplification include one or more surfaces.

In some embodiments, a surface has attached a population of first primers, the first primers of the population sharing a common first primer sequence. In some embodiments, a surface has attached a population of first primers and a population of second primers, the first primers of the population sharing a common first primer sequence and the second primers of the population of second primers sharing a common second primer sequence. In some embodiments, the surface has immobilized thereon a population of first primers. In other embodiments, the surface has immobilized thereon a population of first primers and a population of second primers.

A support or surface can be coated with an acrylamide, carboxylic, or amine compound for attaching a nucleic acid molecule (e.g., a first primer or second primer). In some embodiments, an amino-modified nucleic acid molecule (e.g., primer) is attached to a support that is coated with a carboxylic acid. In some embodiments, an amino-modified nucleic acid molecule is reacted with EDC (or EDAC) for attachment to a carboxylic acid coated surface (with or without NHS). A first primer can be attached to an acrylamide compound coating on a surface. Particles can be coated with an avidin-like compound (e.g., streptavidin) for binding biotinylated nucleic acids.

In some embodiments, the reaction mixture includes multiple different surfaces, for example, the pre-seeding reaction mixture includes one or more beads (such as particles, nanoparticles, microparticles, and the like) and at least two different template nucleic acid molecules are amplified onto different beads, thereby forming at least two different beads, each of which is attached to a different template nucleic acid molecule. In some embodiments, the pre-seeding reaction mixture includes a single surface (for example, a planar-like surface, a flowcell, or array of reaction chambers) and at least two different template nucleic acid molecules are amplified onto two different regions or locations on the surface, thereby forming a single surface attached to two or more template nucleic acid molecules.

In some embodiments, a surface of a solid support is porous, semi-porous or non-porous. In some embodiments, a surface is a planar surface, as well as concave, convex, or any combination thereof. In some embodiments, a surface is a bead, particle, microparticle, sphere, filter, flowcell, well, groove, channel reservoir, gel, or inner wall of a capillary. In some embodiments, a surface includes texture (e.g., etched, cavitated, pores, three-dimensional scaffolds or bumps).

In some embodiments, a surface of a solid support is a magnetic or paramagnetic bead (e.g., magnetic or paramagnetic nanoparticles or microparticles). In some embodiments, paramagnetic microparticles are paramagnetic beads attached with streptavidin (e.g., Dynabeads™ M-270 from Invitrogen, Carlsbad, Calif.). Particles can have an iron core, or can be a hydrogel or agarose (e.g., Sepharose™).

In some embodiments, the surface includes the surface of a bead. In some embodiments, a bead is a polymer material. For example, a bead can be a gel, hydrogel, or acrylamide polymers. A bead can be porous. Particles can have cavitation or pores, or can include three-dimensional scaffolds. In some embodiments, particles are Ion Sphere™ Particles (ThermoFisher Scientific, Waltham, Mass.).

In general, the polymeric particle or bead support can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

In particular, a solid phase support, such a bead support, can include copies of polynucleotides. In a particular example, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

In some embodiments, one or more nucleic acid templates are immobilized onto one or more supports. Template nucleic acid molecules may be immobilized on the support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube. A solid support means any solid phase material upon which an oligomer is synthesized, attached, ligated, or otherwise immobilized. A support can optionally include a "resin", "phase", "surface", and "support". A support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to include one or more wells, depressions or other containers, vessels, features, or locations. One or more supports may be configured in an array at various locations. A support is optionally addressable (e.g., for robotic delivery of reagents), or by detection means including scanning by laser illumination and confocal or deflective light gathering. A support (e.g., a bead) can be placed within or on another support (e.g., within a well of a second support). In some embodiments, a support is an Ion Sphere Particle.

In some embodiments, the solid support is a "microparticle," "bead," "microbead," etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments, a population of microparticles having different shapes sizes and/or colors is used. The microparticles can optionally be encoded, e.g., with quantum dots such that each microparticle or group of microparticles can be individually or uniquely identified.

In some embodiments, a bead surface is functionalized for attaching a population of first primers. In some embodiments, a bead is any size that can fit into a reaction chamber. For example, one bead can fit in a reaction chamber. In some embodiments, more than one bead fit in a reaction chamber. In some embodiments, the smallest cross-sectional length of a bead (e.g., diameter) is about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In some embodiments, the two or more different template nucleic acid molecules are localized, deposited, or positioned at different sites prior to the pre-seeding reaction. In some embodiments, the two or more different template nucleic acid molecules are pre-seeded in solution, optionally within a single pre-seeding reaction mixture, and the resulting two or more substantially monoclonal populations of template nucleic acid molecules are then localized, deposited, or positioned at different sites following such amplification. The different sites are optionally members of an array of sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

In some embodiments, the methods for pre-seeding template nucleic acid molecules onto one or more supports, as well as the templating reactions, typically use one or more enzymes capable of polymerization. In any of the embodiments of the present teachings, the one or more enzymes capable of polymerization include at least one polymerase. In some embodiments, the at least one polymerase includes a thermostable or thermolabile polymerase. In some embodiments, the at least one polymerase includes a biologically active fragment of a DNA or RNA polymerase that maintains sufficient catalytic activity to polymerize or incorporate at least one nucleotide under any suitable conditions. In various embodiments, the at least one polymerase includes a mutated DNA or RNA polymerase that maintains sufficient catalytic activity to perform nucleotide polymerization under any suitable conditions. In various embodiments, the at least one polymerase includes one or more amino acid mutations that maintains sufficient catalytic activity to perform polymerization. The polymerase optionally can have, or lack, exonuclease activity. In some embodiments, the polymerase has 5' to 3' exonuclease activity, 3' to 5' exonuclease activity, or both. Optionally, the polymerase lacks any one or more of such exonuclease activities. In some embodiments, the polymerase has strand-displacing activity. Examples of useful strand-displacing polymerases include Bacteriophage Φ29 DNA polymerase and Bst DNA polymerase.

In some embodiments, a polymerase includes any enzyme or fragment or subunit thereof, that can catalyze polymerization of nucleotides and/or nucleotide analogs. In some embodiments, a polymerase requires an extendible 3' end. For example, a polymerase requires a terminal 3' OH of a nucleic acid primer to initiate nucleotide polymerization. The polymerase can be other than a thermostable polymerase. For example, the polymerase can be active at 37° C. and/or more active at 37° C. than at 50° C., 60° C., 70° C. or higher. In various embodiments, the polymerase can be active and/or more active at 42° C., 45° C., 50° C., 55° C., or 60° C. than at 37° C.

A polymerase can include any enzyme that can catalyze the polymerization of nucleotides (including analogs thereof) into a nucleic acid strand. Typically, but not necessarily, such nucleotide polymerization can occur in a template-dependent fashion. In some embodiments, a polymerase is a high-fidelity polymerase. Such polymerases can include, without limitation, naturally-occurring polymerases and any subunits and truncations thereof, mutant polymerases, variant polymerases, recombinant, fusion or otherwise engineered polymerases, chemically-modified polymerases, synthetic molecules or assemblies, and any analogs, derivatives, or fragments thereof that retain the ability to catalyze such polymerization. Optionally, the polymerase is a mutant polymerase with one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins including at least two portions linked to each other, where the first portion can include a peptide that can catalyze the polymerization of nucleotides into a nucleic acid strand and is linked to a second portion that can include a second polypeptide, such as, for example, a reporter enzyme or a processivity-enhancing domain. Typically, the polymerase includes one or more active sites at which nucleotide binding and/or catalysis of nucleotide polymerization can occur. In some embodiments, a polymerase can include or lack other enzymatic activities, such as for example, 3' to 5' exonuclease activity or 5' to 3' exonuclease activity. In some embodiments, a polymerase is isolated from a cell, or generated using recombinant DNA technology or chemical synthesis methods. In any of the embodiments of the present teachings, a polymerase is expressed in prokaryote, eukaryote, viral, or phage organisms. In various embodiments, a polymerase is a DNA polymerase and include without limitation bacterial DNA polymerases, eukaryotic DNA polymerases, archaeal DNA polymerases, viral DNA polymerases, and phage DNA polymerases. In various embodiments, the expressed polymerase is purified using methods known in the art. In some embodiments, a polymerase is post-translationally modified proteins or fragments thereof.

In some embodiments, the polymerase includes any one or more polymerases, or biologically active fragments of a polymerase, as described in U.S. Patent Publ. No. 2011/0262903 to Davidson et al., published Oct. 27, 2011, and/or International PCT Publ. No. WO 2013/023176 to Vander Horn et al., published Feb. 14, 2013, herein incorporated by reference in their entireties.

In some embodiments, a polymerase is a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, a polymerase is any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-440. In some embodiments, a polymerase is a T3, T5, T7, or SP6 RNA polymerase.

In some embodiments, nucleic acid amplification reactions are conducted with one type or a mixture of polymerases and/or ligases. In some embodiments, nucleic acid amplification reactions are conducted with a low-fidelity or high-fidelity polymerase or without regard to fidelity.

An exemplary polymerase is Bst DNA Polymerase (Exonuclease Minus), is a 67 kDa *Bacillus stearothermophilus* DNA Polymerase protein (large fragment), exemplified in accession number 2BDP_A, which has 5' to 3' polymerase activity and strand displacement activity but lacks 3' to 5' exonuclease activity. Other polymerases include Taq DNA polymerase I from *Thermus aquaticus* (exemplified by accession number 1TAQ), Eco DNA polymerase I from *Escherichia coli* (accession number P00582), Aea DNA polymerase I from *Aquifex aeolicus* (accession number 067779), or functional fragments or variants thereof, e.g., with at least 80%, 85%, 90%, 95% or 99% sequence identity at the nucleotide level.

In illustrative embodiments, the DNA polymerase is a Bsu DNA polymerase (large fragment (NEB)). Bsu DNA Polymerase I, Large Fragment retains the 5' to 3' polymerase activity of the *Bacillus subtilis* DNA polymerase I (1), but lacks the 5' to 3' exonuclease domain. In certain embodiments, the Bsu DNA Polymerase large fragment lacks 3' to 5' exonuclease activity. In various embodiments, Bsu DNA Polymerase large fragment has optimal activity at 37° C.

In certain illustrative embodiments, especially where the pre-seeding reaction is an RPA reaction, the one or more enzymes capable of polymerization include a T5 or T7 DNA polymerase. In some embodiments, the one or more enzymes capable of polymerization include a T5 or T7 DNA polymerase having one or more amino acid mutations that reduce the 3' to 5' exonuclease activity. In some embodiments, the T5 or T7 DNA polymerase having one or more amino acid mutations that reduce the 3 to 5' exonuclease activity does not contain an amino acid mutation that disrupts the processivity of the T5 or T7 DNA polymerase. In some embodiments, the T5 or T7 DNA polymerase includes one or more amino acid mutations that eliminate detectable 3' to 5' exonuclease activity; and wherein the one or more amino acid mutations do not disrupt processivity of the T5 or T7 DNA polymerase. In certain illustrative embodiments, the pre-seeding reaction mixture includes a Sau polymerase, T7 DNA polymerase with reduced 3' to 5' exonuclease activity, Bsu polymerase, or a combination thereof. These polymerases that are especially well suited for an RPA reaction, are well-suited not only for the pre-seeding reaction, but the templating reaction as well.

In some embodiments, the one or more enzymes capable of polymerization include any suitable RNA polymerase. Suitable RNA polymerases include, without limitation, T3, T5, T7, and SP6 RNA polymerases.

In various embodiments, template nucleic acid molecules used in any of the methods of the present teachings, including the pre-seeding reaction and the templating reaction, typically include a first primer binding sequence ("forward") and optionally a second primer binding sequence ("reverse"). Accordingly, the pre-seeding reaction mixture and the templating reaction include a population of first primers and optionally a population of second primers that bind the forward primer binding and reverse primer binding sequences, respectively. In some embodiments, the first and second primers are referred to as a primer pair. In some embodiments, the first primers and/or the second primers are typically universal primers. The first primer can bind to either the forward primer binding sequence or the reverse primer binding sequence and the second primer can bind to either the forward primer binding sequence or the reverse primer binding sequence.

In any of the disclosed embodiments, the reaction mixture includes a population of first primers and a population of second primers that bind to sequences within the template nucleic acid molecules. The population of first primers can be identical copies or different sequences. The population of second primers can be identical copies or different sequences. However, the population of first primers and optional second primers, are typically a universal primer and all copies are identical. Thus, in illustrative embodiments, the population of first primers and the population of second primers are both be universal primers that bind universal primer binding sequences on the template nucleic acid molecules. In other embodiments, both the population of first primers and the population of second primers are target-specific primers. The population of first primers and the population of second primers can have the same or different sequences. In any of embodiments of the present teachings, the population of first primers and/or the population of second primers are attached to one or more supports prior to incubation with the pre-seeding reaction mixture. In other embodiments, the population of first primers and/or the population of second primers are in solution during incubation with the pre-seeding reaction mixture. In illustrative embodiments, the population of first primers is attached to one or more supports prior to incubation with the pre-seeding reaction mixture and the population of second primers is typically in solution during incubation with the pre-seeding reaction mixture.

Thus, in these illustrative embodiments that include a population of immobilized first primers and a population of second primers in solution, not to be limited by theory, during the pre-seeding reaction, a template nucleic acid is at least partially denatured, and the first primer binding site on the template binds to a first template attached to a solid support. The first primer is used by a polymerase to generate a complementary strand to one strand of the template nucleic acid. That complementary strand is now covalently attached to the solid support through the primer. A second primer in solution is in a complex with the recombinase and binds to a primer binding site on the complementary strand, thus partially denaturing the bound template nucleic acid molecule. A polymerase use the primer to synthesize a new strand, identical to the original template nucleic acid strand. This strand is then believed to be partially denatured by the binding of the complex of a recombinase and a nearby first primer attached to the solid support, and the polymerase synthesizes another complementary strand. Through repeated steps of this process, a substantially monoclonal population of template nucleic acid molecules is generated during the pre-seeding reaction, and further amplified during a templating reaction.

In some embodiments, the disclosure relates generally to methods, as well as systems, compositions, kits and apparatuses, in which the primers typically have a free 3' hydroxyl. In some embodiments, the primers are polymers of ribonucleotides, deoxyribonucleotides, or analogs thereof. In some embodiments, primers are naturally-occurring, synthetic, recombinant, cloned, amplified, or unamplified forms. In some embodiments, the primers include phosphodiester linkages between all nucleotides. In any of the embodiments of the present teachings, the primers are between about 5 and 100 nucleotides in length, for example between about 5 and 80 nucleotides in length, between about 5 and 60 nucleotides in length, between about 5 and 40 nucleotides in length, between about 10 and 75 nucleotides in length, between about 15 and 75 nucleotides in length, or between about 20 and 50 nucleotides in length.

In some embodiments, at least one of the primers has modifications. For example, ribonucleotide, deoxyribonucleotides, or analogs thereof can have biotin or azide attached to them. In some embodiments, the ribonucleotide, deoxyribonucleotides, or analogs thereof have attached fluorophores, phosphorylation, or spacers. In some embodiments, the primers are blocked and/or are fusion primers or fusion polynucleotides where different regions of the primers or polynucleotides are designed to bind to one of two primer binding sites and/or are designed to be bound by one of two primers.

In some embodiments, the primers are blocked primers to prevent extension from the 3' end of the primer. In some embodiments, the blocked primers are tailed primers wherein the 5' end includes a sequence that is non-complementary to the template nucleic acid molecules. This 5' sequence can be used as a template for primer extension reactions. In some embodiments, the primers are blocked wherein the 5' domain is 15 to 30 nucleotides in length. In some embodiments, the primers include a blocking moiety at their 5' or 3' end, or at the 5' and 3' ends. In a reaction that involves primer extension (e.g., pre-seeding amplification), the blocking moiety at the 3' end of the blocked fusion primers can reduce the level of primer-dimer formation. In certain embodiments, the pre-seeding reaction mixture includes a blocked primer wherein the 3' domain is 14 to 25 nucleotides in length. In other embodiments, the 3' domain is 15 to 25 nucleotides in length. In still other embodiments, the 5' domain is at least 15 nucleotides and the 3' domain is at least 10 nucleotides, wherein the length of the primer does not exceed 100, 90, 80, 75, 70, 60, or 50 nucleotides. In embodiments, a 3' nucleotide of the 3' domain of the forward primer is mismatched to the forward primer binding sequence. In embodiments, the ribobase separating the 5' domain and the 3' domain of the blocked primer includes rU, rG, rC, or rA. In certain embodiments, the ribobase separating the 5' domain and the 3' domain of the blocked primer includes rC. In any of the embodiments of the present teachings, the 3' domain of the blocked primers is 14 to 20 nucleotides in length and the ribobase is rU, rG, rC or rA.

In any of the embodiments of the present teachings, the reaction mixture includes an enzyme to remove a portion of the blocked primers to leave a free 3' OH. After removing the blocked end of the primer, a polymerase can initiate replication from the free 3' OH to begin replicating the template strand. In some embodiments, this enzyme is an RNase, especially RNase H. A skilled artisan will recognize other compositions of blocked primers to use and suitable enzymes for removing a portion of the blocked primers.

The pre-seeding reaction mixture, as well an any other amplification reaction in the methods provided here, including the templating reaction mixture, typically includes a source of nucleotides, or analogs thereof, that is used by the polymerase as substrates for an extension reaction. In any of the embodiments of the present teachings, the pre-seeding reaction mixture typically includes nucleotides (dNTPs) for strand extension of the template nucleic acid molecules resulting in a substantially monoclonal population of template nucleic acid molecule sequence attached to one or more supports. In some embodiments, nucleotides are not extrinsically labeled. For example, the nucleotides can be naturally-occurring nucleotides or synthetic analogs that do not include fluorescent moieties, dyes, or other extrinsic optically detectable labels. Optionally, the nucleotides do not include groups that terminate nucleic acid synthesis (e.g., dideoxy groups, reversible terminators, and the like). In other embodiments, the nucleotides include a label or tag.

In some embodiments, methods for nucleic acid amplification includes at least one cofactor, for example a cofactor that enhances activity of a DNA or RNA polymerase. In some embodiments, a cofactor includes one or more divalent cations. Examples of divalent cations include magnesium, manganese, and calcium. In various embodiments, the pre-seeding reaction mixture includes a buffer containing one or more divalent cation. In illustrative embodiments, the buffer contains magnesium or manganese ions. In any of the embodiments of the present teachings, the pre-seeding reaction or the templating reaction is initiated by the addition of a cofactor, especially a divalent cation. In some embodiments, the pre-seeding reaction mixture used herein for nucleic acid amplification may include at least one cofactor for recombinase assembly on nucleic acids or for homologous nucleic acid pairing. In some embodiments, a cofactor includes any form of ATP including ATP and ATPγS. In some embodiments, methods for nucleic acid amplification includes at least one cofactor that regenerates ATP. For example, a cofactor can include an enzyme system that converts ADP to ATP. In some embodiments, a cofactor enzyme system is phosphocreatine and creatine kinase.

In any aspects of the present teachings, the pre-seeding reaction mixture includes components to partially denature template nucleic acid molecules. In some embodiments, partially denaturing conditions include treating or contacting the template nucleic acid molecules to be amplified with one or more enzymes that are capable of partially denaturing the nucleic acid template, optionally in a sequence-specific or sequence-directed manner, as in an RPA reaction. In some embodiments, at least one enzyme catalyzes strand invasion and/or unwinding, optionally in a sequence-specific manner. Optionally, the one or more enzymes include one or more enzymes selected from the following: recombinases, topoisomerases, and helicases. In some embodiments, partially denaturing the template includes contacting the template with a recombinase and forming a nucleoprotein complex including the recombinase. Optionally, the template nucleic acid molecule is contacted with a recombinase in the presence of a first and optionally a second primer. Partially denaturing can include catalyzing strand exchange using the recombinase and hybridizing the first primer to the first primer binding sequence (or hybridizing the second primer to the second primer binding sequence). In some embodiments, partially denaturing includes performing strand exchange and hybridizing both the first primer to the first primer binding sequence and the second primer to the second primer binding sequence using the recombinase.

In some embodiments, partially denaturing the template nucleic acid molecule includes contacting the template with one or more recombinases or nucleoprotein complexes. At least one of the nucleoprotein complexes can include a recombinase. At least one of the nucleoprotein complexes can include a primer (e.g., a first primer or a second primer, or a primer including a sequence complementary to a corresponding primer binding sequence in the template). In some embodiments, partially denaturing the template includes contacting the template with a nucleoprotein complex including a primer. Partially denaturing can include hybridizing the primer of the nucleoprotein complex to the corresponding primer binding sequence in the template, thereby forming a primer-template duplex. In some embodiments, partially denaturing the template nucleic acid molecule includes contacting the template with a first nucleoprotein complex including a first primer. Partially denaturing can include hybridizing the first primer of the first nucleoprotein complex to the first primer binding sequence of the forward strand, thereby forming a first primer-template duplex. In some embodiments, partially denaturing the template includes contacting the template with a second nucleoprotein complex including a second primer. Partially denaturing can include hybridizing the second primer of the second nucleoprotein complex to the second primer binding sequence of the reverse strand, thereby forming a second primer-template duplex.

Accordingly, the pre-seeding reaction mixtures of the present disclosure, and a templating reaction of the present disclosure, include a recombinase and partial denaturation and/or amplification, including any one or more steps or methods described herein, can be achieved using a recombinase and optionally a recombinase accessory protein. The recombinase can include any agent that is capable of inducing, or increasing the frequency of occurrence, of a recombination event. A recombination event includes any event whereby two different polynucleotides strands are recombined with each other. Recombination can include homologous recombination. The recombinase optionally can associate with (e.g., bind) a first primer. In some embodiments, an enzyme that catalyzes homologous recombination can form a nucleoprotein complex by binding a single-stranded template nucleic acid molecule. In some embodiments, a homologous recombination enzyme, as part of a nucleoprotein complex, can bind a homologous portion of a double-stranded polynucleotide. In some embodiments, the homologous portion of the polynucleotide hybridizes to at least a portion of the first primer. In some embodiments, the homologous portion of the polynucleotide is partially or completely complementary to at least a portion of the first primer. Suitable recombinases include RecA and its prokaryotic or eukaryotic homologues, or functional fragments or variants thereof, optionally in combination with one or more single-strand binding proteins (SSBs). In certain embodiments, the recombinase optionally coats ssDNA to form a nucleoprotein filament strand which invades a double-stranded region of homology on a template.

In some embodiments, a homologous recombination enzyme catalyzes strand invasion by forming a nucleoprotein complex and binding to a homologous portion of a double-stranded polynucleotide to form a recombination intermediate having a triple-strand structure (D-loop formation) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308, herein incorporated by reference in their entireties).

The recombinase of the reaction mixtures, compositions, and kits includes any suitable agent that can promote recombination between polynucleotide molecules. The recombinase can be an enzyme that catalyzes homologous recombination. For example, the reaction mixture can include a recombinase that includes, or is derived from, a bacterial, eukaryotic or viral (e.g., phage) recombinase enzyme.

In any of the embodiments of the present teachings, a homologous recombination enzyme is wild-type, mutant, recombinant, fusion, or fragments thereof. In some embodiments, a homologous recombination enzyme includes an enzyme from any organism, including myoviridae (e.g., uvsX from bacteriophage T4, RB69, and the like) *Escherichia coli* (e.g., recA) or human (e.g., RAD51). In embodiments, the reaction mixture includes one or more recombinases selected from uvsX, RecA, RadA, RadB, Rad51, a homologue thereof, a functional analog thereof, or a combination thereof. In illustrative embodiments, the recombinase is uvsX. The UvsX protein can be present, for example, at 50-1000 ng/µl, 100-750 ng/µl, 200-600 ng/µl, or 250 to 500 ng/µl.

In some embodiments, methods, kits, and compositions for nucleic acid amplification includes one or more recombinase accessory proteins in the pre-seeding reaction mixture. For example, an accessory protein can improve the activity of a recombinase enzyme. In some embodiments, an accessory protein can bind single strands of template nucleic acid molecules or can load a recombinase onto a template nucleic acid molecule. In some embodiments, an accessory protein is wild-type, mutant, recombinant, fusion, or fragments thereof. In some embodiments, accessory proteins can originate from any combination of the same or different species as the recombinase enzymes that are used to conduct a nucleic acid amplification reaction. Accessory proteins can originate from any bacteriophage including a myoviral phage. Examples of a myoviral phage include T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Accessory proteins can originate from any bacterial species, including *Escherichia coli*, *Sulfolobus* (e.g., *S. solfataricus*) or *Methanococcus* (e.g., *M. jannaschii*). In some embodiments, methods for nucleic acid amplification can include single-stranded binding proteins. Single-stranded binding proteins include myoviral gp32 (e.g., T4 or RB69), Sso SSB from *Sulfolobus solfataricus*, MjA SSB from *Methanococcus jannaschii*, and *E. coli* SSB protein.

In some embodiments, methods for nucleic acid amplification include proteins that improve recombinase loading onto a nucleic acid. For example, UvsY protein is a recombinase-loading protein. In some embodiments, the reaction mixture includes recombinase accessory proteins. In illustrative embodiments, the recombinase accessory protein is uvsY. UvsY can be present between about 20 and 500 ng/µl, for example, between about 20 and 250 ng/µl, or between about 20 and 125 ng/µl. In a non-limiting example, UvsY is present at between 75 and 125 ng/µl.

In any of the embodiments of the present teachings, diffusion within the pre-seeding reaction mixture or the templating reaction mixture, is limited by the addition of a diffusion-limiting agent that is effective in preventing or slowing the diffusion of one or more of the polynucleotide templates and/or one or more of the amplification reaction products through the pre-seeding reaction mixture. Inclusion of a diffusion-limiting agent may be advantageous when amplifying two or more template nucleic acid molecules within a single continuous liquid phase of a reaction mixture. For example, the diffusion-limiting agent can prevent or slow diffusion of template nucleic acid molecules or amplified polynucleotides produced via replication of at least some portion of a template nucleic acid molecule within the pre-seeding reaction mixture, thus preventing the formation of polyclonal contaminants without requiring compartmentalization of the pre-seeding reaction mixture by physical means or encapsulation means (e.g., emulsions) during the amplification. Such methods of amplifying templates within a single continuous liquid phase of a single reaction mixture without need for compartmentalization greatly reduces the cost, time, and effort associated with generation of libraries amenable for high-throughput methods such as digital PCR, next-generation sequencing, and the like.

In some embodiments, the diffusion-limiting agent is a sieving agent. The sieving agent can be any agent that is effective in sieving one or more template nucleic acid molecules or polynucleotides present in the pre-seeding reaction mixture, such as for example amplification reaction products and/or template nucleic acid molecules. In some embodiments, the sieving agent restricts or slows the migration of polynucleotide amplification products through the pre-seeding reaction mixture. In some embodiments, the average pore size of the sieving agent is such that movement of a target component within the pre-seeding reaction mixture (e.g., a polynucleotide) is selectively retarded or prevented. In one example, the sieving agent includes any compound that provides a matrix having a plurality of pores that are small enough to slow or retard the movement of a polynucleotide or template nucleic acid molecule through a reaction mixture containing the sieving agent. Thus, a sieving agent can reduce Brownian motion of a polynucleotide.

In some embodiments, the sieving agent is a polymer compound. In some embodiments, a sieving agent is a cross-linked or a non-cross linked polymer compounds. By way of non-limiting examples, the sieving agent can include polysaccharides, polypeptides, organic polymers, or any other suitable polymer. In any of the embodiments, a sieving agent is polymers that are linear or branched. In some embodiments, a sieving agent is charged or neutral polymers. In some embodiments, the sieving agent can include a blend of one or more polymers, each having an average molecular weight and viscosity. In some embodiments, the sieving agent is a polymer with an average molecular weight of between about 10,000 and 2,000,000 Da, for example between about 10,000 and 1,000,000 Da, between about 10,000 and 500,000 Da, between about 10,000 and 250,000 Da, or between about 10,000 and 100,000 Da. In certain embodiments, the polymer has an average molecular weight between about 12,000 and 95,000 Da or between about 13,000 and 95,000 Da.

In some embodiments, a sieving agent exhibits an average viscosity range of about 5 centipoises to about 15,000 centipoises when dissolved in water at 2 weight percent measured at about 25° C., or about 10 centipoises to about 10,000 centipoises as a 2% aqueous solution measured at about 25° C., or about 15 centipoises to about 5,000 centipoise as a 2% aqueous solution measured at about 25° C.

In some embodiments, the sieving agent has a viscosity average molecular weight ($M_v$) of about 25 to about 1,5000 $kM_v$, or about 75-1,000 $kM_v$, or about 85-800 $kM_v$. In some embodiments, the reaction mixture includes a sieving agent at about 0.1 to about 20% weight per volume (w/v), or about 1-10% w/v, or about 2-5% w/v.

In some embodiments, the sieving agent is a polysaccharide polymer. In some embodiments, a sieving agent is a polymer of glucose or galactose. In some embodiments, a sieving agent is one or more of the following polymers: cellulose, dextran, starch, glycogen, agar, chitin, pectin, or agarose. In some embodiments, the sieving agent is a glucopyranose polymer. In some embodiments, the sieving agent includes a cellulose derivative, such as sodium carboxy methyl cellulose, sodium carboxymethyl 2-hydroxyethyl cellulose, methyl cellulose, hydroxyl ethyl cellulose, 2-hydroxypropyl cellulose, carboxy methyl cellulose, hydroxyl propyl cellulose, hydroxyethyl methyl cellulose, hydroxybutyl methyl cellulose, (hydroxypropyl)methyl cellulose or hydroxyethyl ethyl cellulose, or a mixture including any one or more of such polymers.

In some embodiments, the pre-seeding reaction mixture and/or the templating reaction mixture includes a mixture of different sieving agents, for example, a mixture of different cellulose derivatives, starch, polyacrylamide, and the like. In some embodiments, the pre-seeding reaction mixture includes a crowding agent. In some embodiments, the pre-seeding reaction mixture includes both a crowding agent and a sieving agent.

In some embodiments, the diffusion-limiting agent is a diffusion-reducing agent. A diffusion-reducing agent includes any compound that reduces migration of template nucleic acid molecules or polynucleotides from a region of higher concentration to one having a lower concentration. In some embodiments, a diffusion-reducing agent includes any compound that reduces migration of any component of a nucleic acid amplification reaction irrespective of size.

It should be noted that the concepts of a sieving agent and a diffusion-reducing agent are not necessarily mutually exclusive; a sieving agent can frequently be effective in reducing diffusion of target compounds through a reaction mixture, whereas a diffusion-reducing agent can frequently have a sieving effect on reaction components. In some embodiments, the same compound or pre-seeding reaction mixture additive can act both as a sieving agent and/or a diffusion-reducing agent. Any of the sieving agents of the present teachings can in some embodiments be capable of acting as a diffusion-reducing agent and vice versa.

In some embodiments, the diffusion-reducing agent and/or sieving agent includes polyacrylamide, agar, agarose or a cellulose polymer such as hydroxyethyl cellulose (HEC), methyl-cellulose (MC), or carboxymethyl cellulose (CMC).

In some embodiments, the sieving agent and/or the diffusion-reducing agent is included in the pre-seeding reaction mixture at concentrations of at least 1%, 2%, 5%, 10%, 15%, 20%, 25%, 30%, 40%, 50%, 75%, 90%, or 95% w/v (weight of agent per unit volume of reaction mixture).

In some embodiments, the diffusion-limiting agent is a crowding agent. For example, a crowding agent can increase the concentration of one or more components in a nucleic acid amplification reaction by generating a crowded reaction environment. In some embodiments, the pre-seeding reaction mixture includes both a sieving agent and/or diffusion reagent and a crowding agent.

In some embodiments, different template nucleic acid molecules are pre-seeded onto one or more different discrete supports (e.g., beads or particles) without the need for compartmentalization prior to amplification. In other embodiments, the template nucleic acid molecules are partitioned or distributed into emulsions prior to amplifying. The pre-seeding reactions can be carried out in parallel in a plurality of compartmentalized reaction volumes, as opposed to amplification within a single continuous liquid phase. Each reaction volume can include the pre-seeding reaction mixture. For example, the template nucleic acid molecules can be distributed or deposited into an array of reaction chambers, or an array of reaction volumes, such that at least two such chambers or volumes in the array receive a single template nucleic acid molecule. In some embodiments, a plurality of separate reaction volumes is formed. The reaction chambers (or reaction volumes) can optionally be sealed prior to amplification. Pre-seeding reactions can be performed in each of the reaction chambers to generate substantially monoclonal populations of template nucleic acid molecules. In another embodiment, the reaction mixture is compartmentalized or separated into a plurality of microreactors dispersed within a continuous phase of an emulsion. Each compartment or microreactor serves as an independent amplification reactor, thus the entire emulsion is capable of supporting many separate amplification reactions in separate (discontinuous) liquid phases in a single reaction vessel (e.g., an Eppendorf tube or a well). As used herein, the term "emulsion" includes any composition including a mixture of a first liquid and a second liquid, wherein the first and second liquids are substantially immiscible with each other. The compartmentalized or separate reaction volumes optionally do not mix or communicate, or are not capable of mixing or communicating, with each other. The pre-seeding reaction mixtures in the microreactors can be any of the pre-seeding reaction mixtures discussed herein.

In some embodiments, the nucleic acid synthesis method further includes recovering from the emulsion at least some of the supports attached to substantially monoclonal populations of template nucleic acid molecules. In some embodiments, the nucleic acid synthesis method further includes depositing onto a surface at least some of the supports attached to the substantially monoclonal populations of template nucleic acid molecules. In some embodiments, the nucleic acid synthesis method further includes forming an array by depositing onto a surface at least some of the supports attached to the substantially monoclonal populations of template nucleic acid molecules.

In some embodiments, the disclosure relates generally to compositions, as well as systems, methods, kits and apparatuses, which includes the pre-seeding reaction mixtures and templating reaction mixtures. Accordingly, provided herein in certain embodiments are reaction mixtures that include a polymerase and one or more pre-seeded supports. The reaction mixture compositions can include a recombinase and optionally a recombinase accessory protein as known for an RPA reaction. In such embodiments, the reaction mixture, especially the pre-seeding reaction mixtures, can include between $5 \times 10^7$ and $10^9$ template nucleic acid molecules in a solution that includes between $5 \times 10^6$ and $10^{10}$ beads, such as Ion Sphere Particles. In illustrative examples, 1 or less than 1 template nucleic acid molecule is included per bead in the pre-seeding reaction mixture. For example, between about 0.1 and 0.9 template nucleic acid molecules can be included per solid support, for example between about 0.1 and 0.7 template nucleic acid molecules, between about 0.1 and 0.5 template nucleic acid molecules, or between about 0.1 and 0.3 template nucleic acid molecules can be included per solid support. The templating reaction mixtures in certain examples, include less than 1,000,000, 500,000, 1,000, 500, 100, 10, or 0 template nucleic acid molecules in solution along with pre-seeded solid supports of the present teachings. In the pre-seeding and the templating reaction mixtures, the polymerase and optionally the recombinase are typically present at effective concentrations for amplification, such as known for an RPA reaction, or at higher concentrations such that they can be combined with other reaction components into a final pre-seeding reaction mixture. In any of the embodiments of the present teachings the volumes of the pre-seeding reaction mixtures and/or templating reaction mixtures are between about 50 and 2,000 µl, for example between about 50 and 1,500 µl, between about 50 and 1,000 µl, between about 50 and 500 µl, between about 50 and 250 µl, or between about 50 and 150 µl. In any of the disclosed embodiments, the volume of the pre-seeding reaction and the volume of the templating reaction mixture is different.

The pre-seeding reaction mixtures, and templating reaction mixtures, can further include other components. For example, the compositions can include nucleotides, a population of first primers, optionally a second primer, cofactors, and a buffer. The population of first primers and optionally a population of second primers can be attached to the one or more supports. As a non-limiting example, the composition include one or more supports, a recombinase such as uvsX, a polymerase such as Sau DNA polymerase, a recombinase-loading protein such as uvsY, a single-stranded binding protein such as gp32 protein, nucleotides, ATP, phosphocreatine, and creatine kinase. The composition can be in liquid form, or it can be in a solid form, such as a dried-down pellet form that can be rehydrated. Furthermore, components of the compositions, can be split up such that any combination of the components can be in a pellet or liquid form, and one or more combinations of the rest of the components can be in one or more separate pellet or liquid forms. Such combinations can form kits that include at least two of such combinations. For example, a kit can include a pellet that includes all the reaction mixture components of the present teachings except for the polymerase enzyme, which can be provided in a separate pellet or liquid in the kit.

In illustrative embodiments, a composition includes a population of template nucleic acid molecules, a polymerase, a recombinase, a forward primer, a reverse primer, nucleotides, and a buffer. In some embodiments, the composition includes a template nucleic acid molecule, a forward primer, a reverse primer, uvsX recombinase, uvsY recombinase loading protein, gp32 protein, Sau DNA polymerase, dNTPs, ATP, phosphocreatine, and creatine kinase.

In some embodiments, a composition includes at least two different template nucleic acid molecules with both a first primer binding sequence and a second primer binding sequence, a recombinase, a recombinase accessory protein, a polymerase, a first universal primer, a second universal primer, dNTPs, and a buffer. In some embodiments, the composition further includes one or more supports. In illustrative embodiments, the composition includes at least two different template nucleic acid molecules with both a first primer binding sequence and a second primer binding sequence, uvsX recombinase, uvsY recombinase loading protein, gp32 protein, Sau DNA polymerase, ATP, phosphocreatine, creatine kinase, a first universal primer attached to a bead support, a second universal primer, and a buffer.

In some embodiments, the pre-seeding reaction mixture or the templating reaction mixture is formed by the individual addition of each component to an aqueous or emulsion solution. In other embodiments, the reaction mixture is in the form of a dehydrated pellet that requires rehydration prior to use. The dehydrated pellet can include, for example, recombinase, an optional recombinase accessory proteins, optionally gp32, DNA polymerase, dNTPs, ATP, optionally phosphocreatine, an optional crowding agent, and optionally creatine kinase. Rehydration buffer can include, for example, Tris buffer, potassium acetate salt, and optionally a crowding agent such as PEG. The DNA polymerase, can be for example, T4 or T7 DNA polymerase, and can further include thioredoxin when the polymerase is T7 DNA polymerase. In some embodiments, when a dehydrated pellet is used that includes reaction mixture components, the pellet is rehydrated with a rehydration buffer and template nucleic acid molecules, primers, and additional nuclease-free water are added to a final volume.

In some embodiments, the pre-seeding reaction mixture or the templating reaction mixture is pre-incubated under conditions that inhibit premature reaction initiation. For example, one or more components in the pre-seeding reaction mixture can be withheld from a reaction vessel to prevent premature reaction initiation. To start the reaction, a divalent cation is added (e.g., magnesium or manganese). In another example, the pre-seeding reaction mixture is pre-incubated at a temperature that inhibits enzyme activity. The reaction can be pre-incubated at about 0-15° C. or about 15-25° C. to inhibit premature reaction initiation. The reaction is then incubated at a higher temperature to increase enzymatic activity. In illustrative embodiments, the pre-seeding reaction mixture is not exposed to a temperature above 42° C. during the reaction.

In any of the disclosed embodiments, the pre-seeding reaction optionally includes repeated cycles of nucleic acid amplification. A cycle of amplification optionally includes (a) hybridization of a first primer to a template strand, (b) primer extension to form a first extended strand, (c) partial or incomplete denaturation of the extended strand from the template strand. Optionally, the denatured portion of the template strand from step (c) is free to hybridize with a different first primer in the next amplification cycle. In some embodiments, primer extension in a subsequent amplification cycle involves displacement of the first extended strand from the template strand. A second primer can be included which hybridizes to the 3' end of the first extended strand. In some embodiments, the disclosed methods (and related compositions, systems, and kits) further include one or more primer extension steps. For example, the methods include extending a primer via nucleotide incorporation using a polymerase. In embodiments, extending a primer includes contacting the hybridized primer with a polymerase and one or more types of nucleotides under nucleotide incorporation conditions. Typically, extending a primer occurs in a template-dependent fashion. Optionally, the disclosed methods (and related compositions, systems, and kits) include extending the first primer by incorporating one or more nucleotides onto the 3' OH of the first primer of the first primer-template duplex using the polymerase, thereby forming an extended first primer. Optionally, the disclosed methods (and related compositions, systems, and kits) include binding a second primer to the second primer binding sequence of the first extended primer by any suitable method (e.g., ligation or hybridization). Optionally, the disclosed methods (and related compositions, systems, and kits) include extending the second primer by incorporating one or more nucleotides into the second primer of the second primer-template duplex using the polymerase, thereby forming an extended second primer.

In some embodiments, extending the first primer results in formation of a first extended primer. The first extended primer can include some or all of the sequence of the reverse strand of the template. Optionally, the first extended primer includes a second primer binding sequence. In some embodiments, extending the second primer results in formation of a second extended primer. The second extended primer can include some or all of the sequence of the forward strand of the template. Optionally, the second extended primer includes a first primer binding sequence. In some embodiments, the methods (and related compositions, systems, and kits) can further include attaching one or more extended primer strands to a support. The attaching can optionally be performed during the amplifying or alternatively after the amplification is complete. In some embodiments, the support is attached to a population of first primers. For example, the support can include a population of first primers, and the methods can include hybridizing at least one of the extended second primers to a first primer of the support, thereby attaching the extended second primer to the support. For example, the first primer can hybridize to a first primer binding sequence in the extended second primer. In some embodiments, the support includes multiple instances of a second primer and the methods include hybridizing at least one of the extended first primer strands to a second primer of the support, as in bridge PCR.

In any of the embodiments of the present teachings, the pre-seeding reaction is carried out using an RPA reaction where partial denaturation and/or amplification, including any one or more steps or methods described herein, is achieved using a polymerase, recombinase, and typically a recombinase accessory protein. Not to be limited by theory, it is believed that the recombinase coats single-stranded DNA (ssDNA) to form a nucleoprotein filament strand which invades a double-stranded region of homology on template nucleic acid molecules. This creates a short hybrid and a displaced strand bubble known as a D-loop. The free 3'-end of the hybridized primer is extended by DNA polymerases to synthesize a new complementary strand. The complementary strand displaces the originally-paired partner strand of the template nucleic acid molecule as it is elongated. In an embodiment, one or more of a pair of primers are contacted with one or more recombinases before being contacted with a template nucleic acid molecule, which is optionally double-stranded. RPA reactions are typically isothermal and is performed within an emulsion.

In any of the embodiments of the present teachings, the pre-seeding reaction is carried out by template walking where portions of double-stranded nucleic acid molecules become dissociated such that a primer is bound to one of the strands to initiate a new round of replication (see, for example, U.S. Patent Publ. No. 2012/0156728, published Jun. 21, 2012, incorporated by reference herein in its entirety). An embodiment of template walking includes a method of primer extension, including: (a) a primer-hybridization step, (b) an extension step, and (c) a walking step. Optionally, the primer-hybridization step includes hybridizing a first primer to a first primer binding sequence on a template nucleic acid molecule ("reverse strand"). Optionally the extension step includes generating an extended first forward strand that is a full-length complement of the reverse strand and is hybridized thereto. The extended first forward strand is, for example, generated by extending the first forward primer in template-dependent fashion using the reverse strand as template. Optionally the walking step includes hybridizing another first primer to the first primer binding sequence where the reverse strand is also hybridized to the first forward strand. For example, the walking step includes denaturing at least a portion of the first primer binding sequence from the forward strand, where another portion of the reverse strand remains hybridized to the forward strand. In any of the disclosed embodiments, the reaction mixture includes one or more supports with the first primer bound thereto, wherein the first primer binding sequence on at least one of the template nucleic acid molecules is complementary or identical to at least a portion of the first primer. In some embodiments, at least one of the template nucleic acid molecules have a second primer binding sequence that is complementary or identical to at least a portion of a second primer. In some embodiments, the second primer is also bound to the support such that amplification can occur back and forth on the surface. In various embodiments, the second primer is in solution. In other embodiments, the second primer is immobilized on the support. Template walking reactions are typically performed at isothermal temperatures and is performed within an emulsion.

Template walking can result in the introduction of many identical nucleotides at the proximal terminus of the template nucleic acid molecule attached to the support. In some embodiments, template walking is performed on one or more supports in such a way that the attached template nucleic acid molecules have fewer than 20, 25, 30, 35, 40, 45, 50, 55, 60, 65, 70, 75, 80, 85, 90, 95, 100, 125, 150, 175, 200, 250, or 300 identical nucleotides introduced at the proximal terminus of the template nucleic acid molecule attached to the support. In other embodiments, template walking is performed on one or more supports in such a way that the attached template nucleic acid molecules have between about 10 and 300 identical nucleotides introduced at the proximal terminus of the template nucleic acid molecule attached to the support, for example between about 10 and 200 identical nucleotides, between about 10 and 150, or between about 10 and 100 identical nucleotides introduced at the proximal terminus of the template nucleic acid molecule attached to the support. In any embodiment, the proximal terminus is the terminus of the template nucleic acid molecule closest to the support to which each template nucleic acid molecule is attached. In some aspects, a template nucleic acid molecule attached to the support is a series of identical nucleotides attached to the template nucleic acid molecule or template nucleic acid segment. In some embodiments, less than 5%, 10%, 15%, 20%, or 25% of each of the substantially monoclonal populations of template nucleic acid molecules have variable numbers of an identical nucleotide at the proximal terminus. For example, less than 5%, 10%, 15%, 20%, or 25% of the each of the substantially monoclonal populations of template nucleic acid molecules can have between about 10 and 300 identical nucleotides introduced at the proximal terminus of the template nucleic acid molecule attached to the support, for example between about 10 and 200 identical nucleotides, between about 10 and 150, between about 10 and 100, or between about 20 and 50 identical nucleotides introduced at the proximal terminus of the template nucleic acid molecule attached to the support.

In any of the disclosed embodiments, the pre-seeding reaction is carried out using PCR methods. A skilled artisan will recognize various methods to perform PCR that will generate substantially monoclonal populations of template nucleic acid molecules. In some embodiments, the pre-seeding reaction is carried out in a single round of PCR. In other embodiments, the pre-seeding reaction is carried out in multiple rounds of PCR. For example, the methods can include diluting the amount of template nucleic acid molecules that are reacted with the supports to reduce the percentage of supports that react with more than one template nucleic acid molecule. In some embodiments, the template nucleic acid molecules are diluted such that the pre-seeding reactions have a support-to-template nucleic acid molecule ratio that is selected to optimize the percentage of supports having a substantially monoclonal population of template nucleic acid molecules attached thereto. For example, the pre-seeding reaction can be carried out with a support-to-template nucleic acid molecule ratio of at least about 1:1, 1.25:1, 1.5:1, 1.75:1, 2:1, 2.5:1, 3:1, 3.5:1, 4:1, 4.5:1, 5:1 10:1, 25:1, 50:1, 75:1, and 100:1. In some embodiments, PCR is performed in an emulsion where the PCR is carried out in a plurality of microreactors in an emulsion as described elsewhere herein.

The described methods for pre-seeding supports include immobilizing one or more reaction components (for example, one or more template nucleic acid molecules and/or primers) during the pre-seeding reaction to prevent cross contamination of amplification reaction products and consequent reduction in monoclonality. One such example includes bridge amplification, where all of the primers required for amplification (e.g., forward and reverse primer) are attached to the surface of a matrix support. In addition to such immobilization, additional immobilization components are included in the reaction mixture. For example, the template nucleic acid molecule and/or amplification primers can be suspended in gels or other matrices during the amplification so as to prevent migration of amplification reaction products from the site of synthesis. Such gels and matrices typically require to be removed subsequently, requiring the use of appropriate "melting" or other recovery steps and consequent loss of yield.

In any of the embodiments of the present teachings, the pre-seeding reaction is carried out under isothermal conditions. In some embodiments, isothermal conditions include a reaction subjected to a temperature variation which is constrained within a limited range during at least some portion of the amplification (or the entire amplification process), including for example a temperature variation that is equal or less than about 10° C., or about 5° C., or about 1-5° C., or about 0.1-1° C., or less than about 0.1° C., or, for example a temperature variation is equal or less than or 10° C., or 5° C., or 1-5° C., or 0.1-1° C., or less than 0.1° C. The temperature of the isothermal reaction can be typically between about 15° C. and 65° C., for example between about 15° C. and 55° C., between about 15° C. and 45° C., between about 15° C. and 37° C., between about 30° C. and 60° C., between about 40° C. and 60° C., between about 55° C. and 60° C., between about 35° C. and 45° C., or between about 37° C. and 42° C. In other embodiments, the pre-seeding reaction is not exposed to a temperature above 40° C., 41° C., 42° C., 43° C., 45° C., or 50° C. Accordingly, in certain embodiments, the reaction mixture is not exposed to hot start conditions. However, it is understood the enzymes used at these temperatures will need to be optimized in combination and may require changes in the enzyme, for example, using a different DNA polymerase, such as Bst instead of Bsu. A rate limiting enzyme may be the polymerase, wherein a high concentration or excess (i.e. non-limiting) amount of the polymerase or a lower temperature ensures the amplification reaction proceeds based on the kinetics of the polymerase.

The pre-seeding reaction can be performed for 0.25 minutes to 240 minutes, thereby amplifying the nucleic acid template. In certain embodiments, the pre-seeding reaction is performed for between about 0.25 and 240 minutes, for example between about 0.25 and 120 minutes, between about 0.25 and 60 minutes, between about 0.25 and 30 minutes, between about 0.25 and 15 minutes between about 0.25 and 10 minutes, between about 0.25 and 7.5 minutes, between about 0.25 and 5 minutes, or between about 2 and 5 minutes. In further illustrative embodiments, the pre-seeding reaction is performed for between about 1.5 and 10 minutes, for example between about 1.5 and 8 minutes, between about 1.5 and 6 minutes, between about 1.5 and 5 minutes, or between about 1.5 and 4 minutes, the reaction is isothermal, and the temperature of the reaction is between about 35° C. and 65° C., for example between about 35° C. and 55° C., between about 35° C. and 45° C., between about 30° C. and 60° C., between about 40° C. and 60° C., between about 40° C. and 55° C., between about 50° C. and 60° C., or between about 37° C. and 42° C. For example, the pre-seeding reaction can be between performed for between about 1 and 10 minutes in an isothermal reaction where the temperature of the reaction can be between about 35° C. and 45° C. or the pre-seeding reaction can be between performed for between about 2 and 5 minutes in an isothermal reaction where the temperature of the reaction can be between about 37° C. and 42° C.

In some embodiments, the methods are performed without subjecting the double-stranded template nucleic acid molecules to extreme denaturing conditions during the amplifying. For example, the methods can be performed without subjecting the template nucleic acid template(s) to temperatures equal to or greater than the $T_m$ of the template(s) during the amplifying. In some embodiments, the methods are performed without contacting the template(s) with chemical denaturants such as NaOH, urea, guanidium, and the like, during the amplifying. In some embodiments, the amplifying includes isothermally amplifying.

In some embodiments, the methods are performed without subjecting the template nucleic acid molecules to extreme denaturing conditions during between about 2 and 50 consecutive cycles, between about 2 and 40 consecutive cycles, between about 2 and 30 consecutive cycles, between about 2 and 25 consecutive cycles, between about 2 and 20 consecutive cycles, or between about 2 and 15 consecutive cycles. For example, the methods can include between about 2 and 50 consecutive cycles, between about 2 and 40 consecutive cycles, between about 2 and 30 consecutive cycles, between about 2 and 25 consecutive cycles, between about 2 and 20 consecutive cycles, or between about 2 and 15 consecutive cycles of nucleic acid synthesis without contacting the nucleic acid template(s) with a chemical denaturant or raising the temperature above 50° C. or 55° C. In some embodiments, the methods include performing between about 2 and 50 consecutive cycles, between about 2 and 40 consecutive cycles, between about 2 and 30 consecutive cycles, between about 2 and 25 consecutive cycles, between about 2 and 20 consecutive cycles, or between about 2 and 15 consecutive cycles of nucleic acid synthesis without subjecting the nucleic acid template(s) to temperatures that are greater than 25° C., 20° C., 15° C., 10° C., 5° C., 2° C. or 1° C. below the actual or calculated $T_m$ of the template or population of templates (or the actual or calculated average $T_m$ of the template or population of templates). The consecutive cycles of nucleic acid synthesis may or may not include intervening steps of partial denaturation and/or primer extension. Optionally, the at least one cycle of template-based replication includes a partial denaturation step, an annealing step, and an extension step. In some embodiments, the attached identical primers in the pre-seeding reaction is a sequence of adenosines or uridines or some combination of adenosines and uridines between about 5 and 100 nucleotides in length, for example between about 5 and 80 nucleotides in length, between about 5 and 60 nucleotides in length, between about 5 and 40 nucleotides in length, between about 10 and 75 nucleotides in length, between about 15 and 75 nucleotides in length, or between about 20 and 50 nucleotides in length.

The pre-seeding reaction result in the formation of a population of pre-seeded supports with populations of substantially monoclonal template nucleic acid molecules attached thereto. In various aspects, the substantially monoclonal populations of template nucleic acid molecules are template nucleic acid molecules with at least 50%, 55%, 60%, 65%, 70%, 75%, 80%, 85%, 90%, 95%, 96%, 97%, 98%, 99%, 99.5%, 99.9% or 100% identity at the sequence level. In some embodiments, the percentage of substantially monoclonal template nucleic acid molecules attached to a pre-seeded support are 50%, 55%, 60%, 65%, 70%, 75%, 80%, 85%, 90%, or 95% of the template nucleic acid molecules attached thereto.

In various embodiments, at least 5%, 10%, 15%, 20%, 25%, 30%, 35%, 40%, 45% 50%, 55%, 60%, 65%, 70%, 75%, 80%, 85%, 90%, 95%, 96%, 97%, 98%, or 99% of the supports in a population of pre-seeded supports have substantially monoclonal populations of nucleic acid molecules attached during the pre-seeding reaction. In illustrative embodiments, at least 50%, 55%, 60%, 65%, 70%, 75%, 80%, 85%, 90%, 95%, 96%, 97%, 98%, or 99% of the supports in a population of pre-seeded supports have substantially monoclonal populations of nucleic acid molecules attached during the pre-seeding reaction.

In some embodiments, a pre-seeding reaction generate supports having zero template nucleic acid molecules attached thereto (empty solid supports), other pre-seeded supports having one type of template nucleic acid molecule attached thereto, and other pre-seeded supports having more than one type of template nucleic acid molecule attached thereto. In any of the embodiments of the present teachings, the number of attached template nucleic acid molecules in the populations of substantially monoclonal template nucleic acid molecules attached to one or more pre-seeded supports are the pre-seeding number. In any of the disclosed embodiments, the pre-seeding number is between about 1 and 150,000 template nucleic acid molecules, for example between about 1 and 100,000, between about 1 and 75,000, between about 1 and 50,000, between about 1 and 25,000, between about 1 and 10,000, between about 1 and 5,000, or between about 1 and 2,500 template nucleic acid molecules. In illustrative embodiments, the pre-seeding number is between about 10 and 100,000 template nucleic acid molecules, for example between about 10 and 75,000, between about 10 and 50,000, between about 10 and 25,000, between about 10 and 10,000, between about 10 and 5,000, or between about 10 and 2,500 template nucleic acid molecules.

In some embodiments, after the pre-seeding reaction, a majority of any primers attached to a support are not bound to a template nucleic acid molecule. These unbound primers can be used in the subsequent templating reaction for further amplification of the template nucleic acid molecules. For example, after the pre-seeding reaction, at least 90%, 95%, 96%, 97%, 98%, or 99% of primers attached to a support are typically not bound to a template nucleic acid molecule.

In some embodiments, the disclosure relates generally to methods, as well as systems, compositions, kits and apparatuses, wherein the methods typically include a templating reaction after the pre-seeding reaction wherein the template nucleic acid molecules on the pre-seeded supports are further amplified (herein referred to as the templating reaction). The templating reaction mixture does not include additional template nucleic acid molecules in solution such that the template nucleic acid molecules attached to the one or more pre-seeded supports are the predominant or only source of template nucleic acid molecules in the templating reaction mixture before the templating reaction is initiated. In illustrative embodiments, one or more washes are carried out on the one or more pre-seeded supports before introducing them into the templating reaction mixture. In some embodiments, less than 10%, 9%, 8%, 7%, 6%, 5%, 4%, 3%, 2%, 1%, or 0.1% of the template nucleic acid molecules in solution at the end of the pre-seeding reaction mixture are present in the templating reaction. In any of the embodiments of the present teachings, the percentage of template nucleic acid molecules in the templating reaction mixture that are attached (have been pre-seeded) on one or more supports before the templating reaction is initiated are at least 50%, 55%, 60%, 65%, 70%, 75%, 80%, 85%, 90%, 95%, 96%, 97%, 98%, 99%, 99.5%, or 99.9% of the template nucleic acid molecules in the reaction mixture.

In any of the embodiments of the present teachings, the templating reaction is typically an RPA reaction. As such, any details regarding components and conditions for an RPA reaction discussed above for a pre-seeding reaction apply to the templating reaction except that template nucleic acids are typically present in the initial reaction mixture for a pre-seeding reaction, but not for a templating reaction. The templating reaction mixture typically includes all or some of the following: one or more pre-seeded solid supports that include a population of attached substantially identical first primers and have substantially monoclonal template nucleic acid molecules attached thereto, a polymerase, a recombinase, an optional single-stranded binding protein, an optional recombinase loading protein, an optional second or reverse primer, which can be attached to the solid support, but in illustrative examples, is in solution, dNTPs, ATP, a buffer, and optionally one or both of phosphocreatine and creatine kinase. A divalent cation, such as $MgCl_2$ or $Mg(OAc)_2$, can be added to start the reaction. In various embodiments, the buffer included a crowding agent, such as PEG, Tris buffer, and/or a potassium acetate salt. A forward primer binding sequence on template nucleic acid molecules is complementary or identical to at least a portion of the forward primer and the optional reverse primer binding sequence on the template nucleic acid molecules is complementary or identical to at least a portion of the reverse primer. Reaction mixtures for templating reactions themselves form separate aspects of the invention. In further illustrative embodiments, the RPA templating reaction is a bulk isothermal amplification or is performed in wells of a multi-well solid support (e.g. see the pre-seeding amplification reaction discussed further herein).

In some embodiments, the templating reaction mixture is pre-incubated under conditions that inhibit premature reaction initiation. For example, one or more components in the templating reaction mixture can be withheld from a reaction vessel to prevent premature reaction initiation. To start the reaction, a divalent cation is added (e.g., magnesium or manganese). In another example, the templating reaction mixture is pre-incubated at a temperature that inhibits enzyme activity. The reaction is pre-incubated at about 0-15° C. or about 15-25° C. to inhibit premature reaction initiation. The reaction can then be incubated at a higher temperature to increase enzymatic activity. In illustrative embodiments, the templating reaction mixture is not exposed to a temperature above 42° C. during the reaction.

Since the templating reaction is typically an RPA reaction, it is carried out under isothermal conditions. In some embodiments, isothermal conditions include a reaction subjected to a temperature variation which is constrained within a limited range during at least some portion of the amplification (or the entire amplification process), including for example a temperature variation that is equal or less than about 10° C., or about 5° C., or about 1-5° C., or about 0.1-1° C., or less than about 0.1° C., or, for example a temperature variation is equal or less than or 10° C., or 5° C., or 1-5° C., or 0.1-1° C., or less than 0.1° C. The temperature of the isothermal reaction is typically between about 15° C. and 65° C., for example between about 15° C. and 55° C., between about 15° C. and 45° C., between about 15° C. and 37° C., between about 30° C. and 60° C., between about 40° C. and 60° C., between about 55° C. and 60° C., between about 35° C. and 45° C., or between about 37° C. and 42° C. about 15° C. In other embodiments, the pre-seeding reaction is not exposed to a temperature above 40° C., 41° C., 42° C., 43° C., 45° C., or 50° C. Accordingly, in certain embodiments, the reaction mixture is not exposed to hot start conditions. However, it is understood the enzymes used at these temperatures will need to be optimized in combination and may require changes in the enzyme, for example, using a different DNA polymerase, such as Bst instead of Bsu. A rate limiting enzyme may be the polymerase, wherein a high concentration or excess (i.e. non-limiting) amount of the polymerase or a lower temperature ensures the amplification reaction proceeds based on the kinetics of the polymerase.

In any of embodiments of the present teachings, the templating reaction is typically an RPA reaction that is performed for between about 0.25 and 240 minutes, for example between about 0.25 and 120 minutes, between about 0.25 and 60 minutes, between about 0.25 and 30 minutes, between about 0.25 and 15 minutes between about 0.25 and 10 minutes, between about 0.25 and 7.5 minutes, between about 0.25 and 5 minutes, or between about 2 and 5 minutes. In illustrative embodiments, the templating reaction is performed for between about 10 and 120 minutes, for example between about 10 and 60 minutes, between about 10 and 45 minutes, between about 10 and 30 minutes, or between about 10 and 20 minutes. In further illustrative embodiments, the templating reaction is performed for between about 20 and 60 minutes, for example between about 20 and 50 minutes, between about 20 and 40 minutes, between about 20 and 35 minutes, or between about 20 and 30 minutes.

In any of embodiments of the present teachings, the templating reaction includes amplifying a population of different template nucleic acid molecules on one or more pre-seeded supports to generate one or more templated supports. For example, after the templating reaction, there can be at least 2, 3, 4, 5, 6, 7, 8, 9, 10, 25, 50, 100, 250, 500, 1,000, 2,500, 5,000, 10,000, 25,000, 50,000, 100,000, 250,000, 500,000, or $10^6$ times as many attached substantially monoclonal template nucleic acid molecules present on the templated solid supports as were present on the pre-seeded solid supports. In illustrative embodiments, there is at least 10, 25, 50, 100, 250, 500, 1,000, 2,500, 5,000, 10,000, 25,000, or 50,000 times as many attached substantially monoclonal template nucleic acid molecules present on the templated solid supports as were present on the pre-seeded solid supports. In some embodiments, at least 50,000, 75,000 or 100,000 substantially monoclonal template nucleic acid molecules or between about 25,000 and 1,000,000 substantially monoclonal template nucleic acid molecules are present on the pre-seeded solid supports, for example between about 25,000 and 500,000, between about 25,000 and 250,000, between about 25,000 and 125,000, or between about 25,000 and 100,000 substantially monoclonal template nucleic acid molecules are present on the pre-seeded solid supports. The support or supports typically remain in fluid communication during the templating reaction.

Since the pre-seeding reaction can be an RPA reaction and the templating reaction is typically an RPA reaction according to the present teachings, the methods include sequential RPA reactions. A first RPA reaction is a pre-seeding reaction, followed by a second RPA templating reaction. The reactions are carried out under the same conditions. However, in illustrative embodiments, the pre-seeding RPA reaction is carried out such that less amplification cycles occur, than for the templating RPA reaction. For example, a pre-seeding RPA reaction can be carried out for less time than a templating RPA reaction that amplifies template nucleic acid molecules attached to pre-seeded solid supports generated by the pre-seeded RPA reaction. As non-limiting illustrative examples, a pre-seeding RPA reaction is carried out for 2 to 5 minutes to generate one or more, for example a population of pre-seeded solid supports, which are then subjected to a templating RPA reaction that is carried out for between 10 and 60 minutes. In these non-limiting illustrative examples, reaction components including template nucleic acids are washed away from the pre-seeded solid supports before the templating RPA reaction. All other reaction components of the pre-seeding and templating reaction, except for template nucleic acid molecules in solution, are included in both the pre-seeding and templating reactions.

In some embodiments, after the templating reaction the percentage of sites on a support or supports in a population of supports with substantially monoclonal template nucleic acid molecules attached thereto are at least 5%, 10%, 15%, 20%, 25%, 30%, 35%, 40%, 50%, 55%, 60%, 65%, 70%, 75%, 80%, 85%, 90%, 95%, 96%, 97%, 98%, or 99% of the total amplified supports (i.e., total supports include empty, polyclonal or substantially monoclonal populations of template nucleic acid molecules). In illustrative embodiments, after the templating reaction the percentage of sites on a support or supports in a population of supports with substantially monoclonal template nucleic acid molecules attached thereto are at least 50%, 55%, 60%, 65%, 70%, 75%, 80%, 85%, 90%, 95%, 96%, 97%, 98%, or 99% of the total amplified supports (i.e., total supports include empty, polyclonal or substantially monoclonal populations of template nucleic acid molecules) recovered from the reaction mixture. In some embodiments, after the templating reaction the percentage of sites on a support or supports in a population of supports with substantially monoclonal template nucleic acid molecules attached thereto are at least 5%, 10%, 15%, 20%, 25%, 30%, 35%, 40%, 50%, 55%, 60%, 65%, 70%, 75%, 80%, 85%, 90%, 95%, 96%, 97%, 98%, or 99% of the total supports recovered from the reaction mixture (i.e., total supports including supports with no attached template nucleic acid molecules and supports with either polyclonal or substantially monoclonal population of template nucleic acid molecules). In illustrative embodiments, after the templating reaction the percentage of sites on a support or supports in a population of supports with substantially monoclonal template nucleic acid molecules attached thereto are at least 50%, 55%, 60%, 65%, 70%, 75%, 80%, 85%, 90%, 95%, 96%, 97%, 98%, or 99% of the total supports recovered from the reaction mixture (i.e., total supports including supports with no attached template nucleic acid molecules and supports with either polyclonal or substantially monoclonal population of template nucleic acid molecules).

In some embodiments, at least a portion of a primer hybridize with a portion of at least one strand of a polynucleotide in the templating reaction mixture. For example, at least a portion of a primer can hybridize with a nucleic acid adapter that is joined to one or both ends of the polynucleotide. In some embodiments, at least a portion of a primer is partially or fully complementary to a portion of the polynucleotide or to the nucleic acid adapter. In some embodiments, a primer is compatible for use in any type of sequencing platform including chemical degradation, chain-termination, sequencing-by-synthesis, pyrophosphate, massively parallel, ion-sensitive, and single-molecule platforms.

In some embodiments, a primer (e.g., first, second or third primer) has a 5' or 3' overhang tail (tailed primer) that does not hybridize with a portion of at least one strand of a polynucleotide in the reaction mixture. In some embodiments, a tailed primer is any length, including between about 1 and 100 nucleotides in length, for example between about 1 and 90, between about 1 and 80 nucleotides in length, between about 1 and 70 nucleotides in length, between about 1 and 60 nucleotides in length, between about 1 and 50 nucleotides in length, between about 1 and 40 nucleotides in length, or between about 1 and 30 nucleotides in length.

The disclosed methods result in the production of a population of amplicons, at least some of which amplicons in certain embodiments, include an amplified nucleic acid population. The amplified populations produced by the methods of the disclosure are useful for a variety of purposes. In some embodiments, the disclosed methods (and related compositions, systems, and kits) optionally include further analysis and/or manipulation of the amplified populations (amplicons). For example, in some embodiments, the numbers of amplicons exhibiting certain desired characteristics are detected and optionally quantified. In some embodiments, the amplifying is followed by sequencing the amplified product. The amplified product that is sequenced can be an amplicon that is a substantially monoclonal nucleic acid population. In some embodiments, the disclosed methods include amplifying single members of a population of amplicons at different sites or on different supports. The different sites optionally form part of an array of sites. In some embodiments, the sites in the array of sites include wells (reaction chambers) on the surface of an isFET array. Optionally, the nucleic acid molecule to be sequenced is positioned at a site. The site can include a reaction chamber or well. The site can be part of an array of similar or identical sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like). In any of the embodiments of the present teachings, the site is operatively coupled to a sensor. The method includes detecting the nucleotide incorporation using the sensor. Optionally, the site and the sensor are located in an array of sites coupled to sensors.

In any of the embodiments of the present teachings, after the templating reaction the templated supports have at least 50,000, 75,000, 100,000, 125,000, 150,000, 200,000, 250,000, 300,000, 350,000, 400,000, 450,000, or 500,000 substantially monoclonal template nucleic acid molecules attached to each templated support. In some embodiments, after the templating reaction the templated supports have between about 50,000 and 500,000 substantially monoclonal template nucleic acid molecules attached to each templated support, for example between about 50,000 and 400,000 substantially monoclonal template nucleic acid molecules, between about 50,000 and 300,000 substantially monoclonal template nucleic acid molecules, between about 50,000 and 200,000 substantially monoclonal template nucleic acid molecules, or between about 50,000 and 100,000 substantially monoclonal template nucleic acid molecules attached to each templated support. In illustrative embodiments, after the templating reaction the templated supports have between about 100,000 and 400,000 substantially monoclonal template nucleic acid molecules attached to each templated support, between about 100,000 and 300,000 substantially monoclonal template nucleic acid molecules, between about 100,000 and 200,000 substantially monoclonal template nucleic acid molecules, or between about 150,000 and 300,000 substantially monoclonal template nucleic acid molecules attached to each templated support.

In any of the disclosed embodiments, the amplified template nucleic acid molecules on the supports is sequenced. Sequencing methods can include any suitable method of sequencing known in the art. In some embodiments, template nucleic acid molecules that have been amplified according to the present teachings are used in any nucleic acid sequencing workflow, including sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeq™, from Illumina), pyrophosphate sequencing (e.g., Genome Sequencer FLX from 454 Life Sciences), ion-sensitive sequencing (e.g., Personal Genome Machine (PGM™), Ion Proton™ Sequencer, Ion S5, and Ion S5 XL, all from Ion Torrent™ Systems, Inc.), single molecule sequencing platforms (e.g., HeliScope™ from Helicos™) nanopore sequencing via read of individual bases as they pass through the nanopores (e.g. MinION from Oxford Nanopore Technologies), chemical degradation sequencing, capillary electrophoresis, gel electrophoresis, and any other next-generation, massively parallel sequencing platforms.

Figure 8:
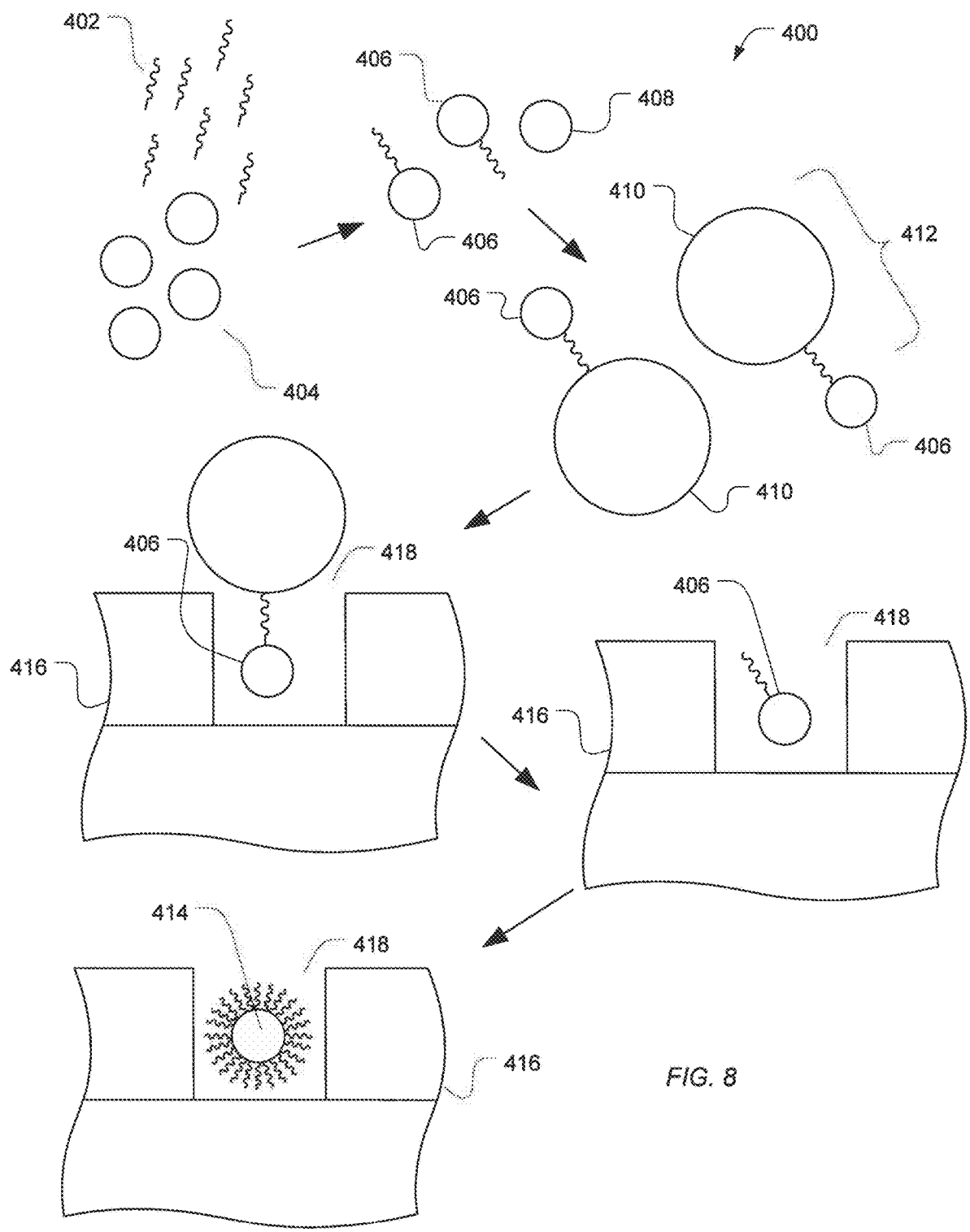
FIG. 8 is an illustration of an example method for preparing a sequencing device.

In some sequencing devices, e.g., Ion Torrent Systems, sequencing reactions are conducted in microwells of a surface such as, for example, a semiconductor chip. An exemplary embodiment of the use of a bead support in a sequencing device that includes reaction chambers such as wells is depicted in FIG. 8. For example, with reference to FIG. 8, an exemplary sequencing device 416 includes an array of wells 418. A bead support 406 including a target polynucleotide 402 to be sequenced is attached to a magnetic bead 410 to form a bead assembly 412 that is designed for introduction of the bead support with attached target polynucleotide into a well. In some embodiments, the magnetic bead 410 is attached to the bead support 406 by a double stranded polynucleotide linkage. In some instances, a linker moiety is hybridized to a portion of the target polynucleotide on the bead support 406. In this example, the linker moiety attaches to a complementary linker moiety on the magnetic bead 410. In another example, the template polynucleotide used to form the target nucleic acid attached to beads 406 includes a linker moiety that attaches to the magnetic bead 410. In another example, the template polynucleotide complementary to target polynucleotide attached to the bead support 406 is generated from a primer that is modified with a linker that attaches to the magnetic bead 410. The linker moiety attached to the polynucleotide and the linker moiety attached to the magnetic bead are, in some embodiments, complementary to and attach to each other. In an example, the linker moieties have affinity and include: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement. In a particular example, the linker moiety attached to the polynucleotide includes biotin and the linker moiety attached to the magnetic bead includes streptavidin.

Figure 9:
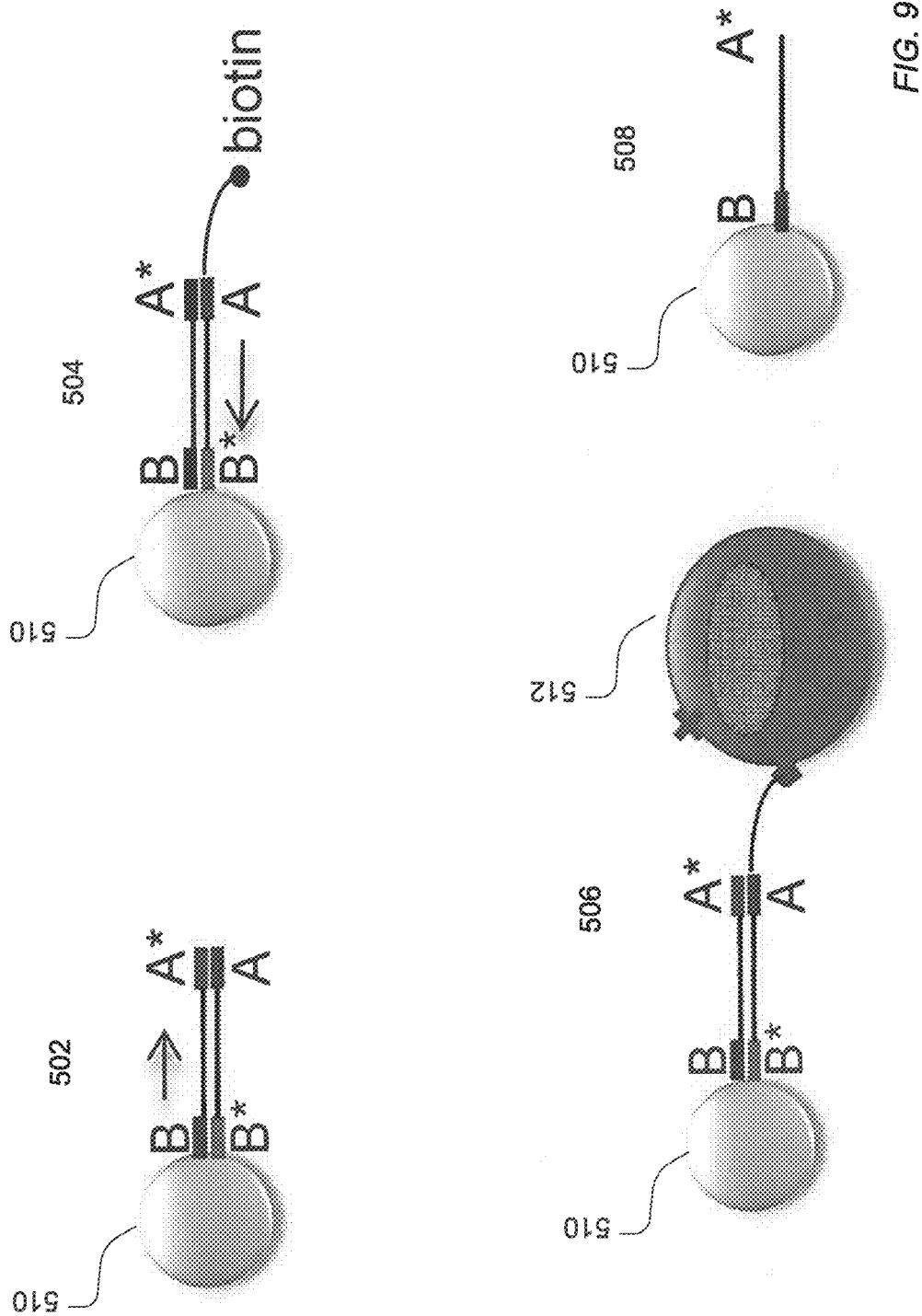
FIG. 9 illustrates example schema for attaching nucleic acids to a bead.

As illustrated in the embodiment depicted in FIG. 8, a plurality of bead supports 404 is placed in a solution along with a plurality of polynucleotides 402 (target or template polynucleotides). The plurality of bead supports 404 is activated or otherwise prepared to bind with the polynucleotides 402. For example, the bead supports 404 include an oligonucleotide (capture primer) complementary to a portion of a polynucleotide of the plurality of polynucleotides 402. In another example, the bead supports 404 are modified with target polynucleotides 402 using techniques such as biotin-streptavidin binding. In a particular embodiment 400, the hydrophilic bead particles and polynucleotides are subjected to polymerase chain reaction (PCR) amplification or recombinase polymerase amplification (RPA). The template polynucleotide will hybridize to the capture primer. The capture primer is extended to form beads 406 that include a target polynucleotide attached thereto. Other beads 408 may remain unattached to a target nucleic acid and other template polynucleotides may be free floating in solution. Various methods are available for seeding the bead supports and capture by the magnetic beads. For example, turning to FIG. 9 at 502, a template polynucleotide (B*-A) is captured by a capture probe (B) attached to a bead support 510. The capture probe (B) is extended complementary to the template polynucleotide producing B-A*. Optionally, the resultant double-stranded polynucleotide is denatured removing the template nucleic acid (B*-A) and leaving a single-stranded (B-A*) attached to the bead support 510. As illustrated at 504 of FIG. 9, a primer (A) modified with a linker moiety, such as biotin, is hybridized to a portion (A*) of the nucleic acid (B-A*) attached to the bead support 510. Optionally, the primer (A) is extended to form a complementary nucleic acid (A-B*). As shown at 506, a magnetic bead 512 is introduced to the solution. The magnetic bead 512 includes a linker complementary to the linker moiety attached to the primer (A). In this example, the linker attached to the primer (A) is biotin and the magnetic bead 512 is coated with streptavidin. The magnetic bead 512 may be utilized to clean the solution and to assist with deposition of the bead support 510 and the attached nucleic acid (B-A*) into a well of a sequencing device. As illustrated in 508 of FIG. 9, in some instances double-stranded polynucleotide of 506 is denatured, resulting in the dehybridization of the nucleic acid (B*-A) from the nucleic acid (B-A*) attached to the bead support 510. As such, the bead support 510 is deposited into the wells of the sequencing device and has a single stranded target nucleic acid (B-A*). Alternatively, the linker modified probe (A) may not be extended to form a complementary polynucleotide with a length the polynucleotide (B-A*). Extension reactions can be carried out using polymerase chain reaction (PCR), recombinase polymerase amplification (RPA), or other amplification reactions.

Turning back to FIG. 8, in an embodiment in which a magnetic bead is utilized to assist with deposition of the bead support and the attached nucleic acid into a well of a sequencing device, bead assemblies 412 are applied over a substrate 416 of a sequencing device that includes wells 418. In an example, a magnetic field can be applied to the substrate 416 to draw the magnetic beads 410 of the bead assembly 412 towards the wells 418. The bead support 406 enters the well 418. For example, a magnet can be moved in parallel to a surface of the substrate 416 resulting in the deposition of the bead support 406 in the wells 418. The bead assembly 412 is denatured to remove the magnetic bead 410 leaving the bead support 406 in the well 418. For example, hybridized double-stranded DNA of the bead assembly 412 can be denatured using thermal cycling or ionic solutions to release the magnetic bead 410 and template polynucleotides having a linker moiety attached to the magnetic bead 410. Optionally, the target polynucleotides 406 can be amplified, such as in a templating reaction, while in the well 418, to provide a bead support 414 with multiple copies of the target polynucleotides. In particular, the bead 414 has a monoclonal population of target polynucleotides. Such amplification reactions are performed, for example, using polymerase chain reaction (PCR) amplification, recombination polymerase amplification (RPA) or a combination thereof. In a particular embodiment, an enzyme such as a polymerase is present, bound to, or is in close proximity to the particles or beads. In an example, a polymerase is present in solution or in the well to facilitate duplication of the polynucleotide. A variety of nucleic acid polymerases may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof. While the polynucleotides of bead support 414 are illustrated as being on a surface, the polynucleotides may extend within the bead support 414. Hydrogel and hydrophilic particles having a low concentration of polymer relative to water may include polynucleotide segments on the interior of and throughout the bead support 414 or polynucleotides may reside in pores and other openings. In particular, in some examples, the bead support 414 permits diffusion of enzymes, nucleotides, primers and reaction products used to monitor the reaction. A high number of polynucleotides per particle generally produces a better signal.

In some embodiments, sequencing includes extending a template nucleic acid molecule or amplified template nucleic acid molecule, or extending a sequencing primer hybridized to a template or amplified template, via nucleotide incorporation by a polymerase. In some embodiments, sequencing includes sequencing a template or amplified template that is attached to a support by contacting the template or extended primer with a sequencing primer, a polymerase, and at least one type of nucleotide. In some embodiments, the sequencing includes contacting the template, or amplified template, or extended primer, with a sequencing primer, a polymerase, and with only one type of nucleotide that does not include an extrinsic label or a chain terminating group. In some embodiments, a sequencing reaction is conducted using at least one sequencing primer that hybridizes to any portion of the polynucleotide constructs, including a nucleic acid adapter or a target polynucleotide sequence.

Returning to FIG. 8, in an example, a sequencing primer is added to the wells 418 or the bead support 414 is pre-exposed to the primer prior to placement in the well 418. In particular, the bead support 414 includes bound sequencing primer. The sequencing primer and polynucleotide form a nucleic acid duplex including the polynucleotide (e.g., a template nucleic acid) hybridized to the sequencing primer. The nucleic acid duplex is an at least partially double-stranded polynucleotide. Enzymes and nucleotides are provided to the well 418 to facilitate detectable reactions, such as nucleotide incorporation. In some embodiments, sequencing involves detecting nucleotide addition. Methods of detecting nucleotide addition include fluorescent emission methods or ion detection methods. For example, a set of fluorescently labeled nucleotides is provided to the system 416 and migrates to the well 418. Excitation energy is also provided to the well 418. When a nucleotide is captured by a polymerase and added to the end of an extending primer, a label of the nucleotide fluoresces, indicating which type of nucleotide is added. In an alternative example, solutions including a single type of nucleotide are fed sequentially. In response to nucleotide addition, the pH within the local environment of the well 418 may change. Such a change in pH is detectable by ion sensitive field effect transistors (ISFET). As such, a change in pH may be used to generate a signal indicating the order of nucleotides complementary to the polynucleotide of the particle 410.

In a typical embodiment of ion-based nucleic acid sequencing, nucleotide incorporations is detected by detecting the presence and/or concentration of hydrogen ions generated by polymerase-catalyzed extension reactions. In one embodiment, template nucleic acid molecules, optionally pre-bound to a sequencing primer and/or a polymerase, can be loaded into reaction chambers after which repeated cycles of nucleotide addition and washing are carried out. In some embodiments, such templates are attached as substantially monoclonal populations to a support, such as particles, bead, or the like, and said substantially monoclonal populations are loaded into reaction chambers.

In each addition step of the cycle, the polymerase extends the primer by incorporating added nucleotide only if the next base in the template is the complement of the added nucleotide in solution. If there is one complementary base on the template nucleic acid molecule, there is one incorporation, if there two complementary bases in a row on the template nucleic acid molecule, there are two incorporations, if three, there are three incorporations, and so on. With each such incorporation, there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released. In some embodiments, after each step of adding a nucleotide, an additional step is performed, in which an unbuffered wash solution at a predetermined pH is used to remove the nucleotide of the previous step in order to prevent misincorporations in later cycles. In some embodiments, after each step of adding a nucleotide, an additional step is performed wherein the reaction chambers are treated with a nucleotide-destroying agent, such as apyrase, to eliminate any residual nucleotides remaining in the chamber, which may result in spurious extensions in subsequent cycles.

In particular embodiments, a sequencing system includes a well, or a plurality of wells, disposed over a sensor pad of an ionic sensor, such as a field effect transistor (FET). In some embodiments, the FET is a FET array. The FET or array may include, for example, $10^2$, $10^3$, $10^4$, $10^5$, $10^6$, $10^7$ or more FETs. In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET is a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor changes accordingly. In some embodiments, one or more microfluidic structures are fabricated above the FET sensor array to provide for containment or confinement of a biological or chemical reaction. For example, in one implementation, the microfluidic structure(s) are configured as one or more wells (or wells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 8, in another example, a well 418 of the array of wells is operatively connected to measuring devices. For example, for fluorescent emission methods, a well 418 may be operatively coupled to a light detection device. In the case of ionic detection, the lower surface of the well 418 may be disposed over a sensor pad of an ionic sensor, such as a field effect transistor.

In some embodiments, different kinds of nucleotides are added sequentially to the reaction chambers, so that each reaction is exposed to the different nucleotides one at a time. For example, nucleotides are added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, the methods (and related compositions, systems, and kits) include detecting the presence of one or more nucleotide incorporation byproducts at a site of the array, optionally using the FET. In some embodiments, the methods include detecting a pH change occurring within the at least one reaction chamber, optionally using the FET. In some embodiments, the disclosed methods further include detecting a change in ion concentration in at least one of the sites as a result of the at least one amplification cycle.

An exemplary system involving sequencing via detection of ionic byproducts of nucleotide incorporation is the Ion Torrent PGM™, Proton™ or S5™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™, or S5™ sequencer detects the nucleotide incorporations by detecting the hydrogen ion byproducts of the nucleotide incorporations. In some embodiments, the Ion Torrent PGM™, Proton™ or S5™ sequencer includes a plurality of template polynucleotides to be sequenced, each template disposed within a respective sequencing reaction well in an array. The wells of the array are each be coupled to at least one ion sensor that detects the release of H+ ions or changes in solution pH produced as a byproduct of nucleotide incorporation. The ion sensor comprises a field effect transistor (FET) coupled to an ion-sensitive detection layer that senses the presence of H+ ions or changes in solution pH. The ion sensor provides output signals indicative of nucleotide incorporation which may be represented as voltage changes whose magnitude correlates with the H+ ion concentration in a respective well or reaction chamber. Different nucleotide types are flowed serially into the reaction chamber, and may be incorporated by the polymerase into an extending primer (or polymerization site) in an order determined by the sequence of the template. For example, a sequencing system containing a fluidics circuit is connected by inlets to at least two reagent reservoirs, a waste reservoir, and to a biosensor by a fluid pathway for fluidic communication. Reagents from reservoirs are driven to the fluidic circuit by a variety of methods including pressure, pumps, such as syringe pumps, gravity feed, and the like, and are selected by control of valves. Reagents from the fluidics circuit are driven through the valves receiving signals from a control system. The control system includes controllers for valves, which generate signals for opening and closing via an electrical connection. The control system also includes controllers for other components of the system, such as a wash solution valve connected thereto by an electrical connection and a reference electrode. Each nucleotide incorporation is accompanied by the release of H+ ions in the reaction well, along with a concomitant change in the localized pH. The release of H+ ions is registered by the FET of the sensor, which produces signals indicating the occurrence of the nucleotide incorporation. Nucleotides that are not incorporated during a particular nucleotide flow may not produce signals. The amplitude of the signals from the FET may also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers permits the instrument to resolve the sequence of many nucleic acid templates simultaneously.

In some embodiments, methods of downstream analysis include sequencing at least some of the population of amplicons in parallel. Optionally, the multiple templates/amplified templates/extended first primers situated at different sites of the array are sequenced in parallel.

In some embodiments, the sequencing includes binding a sequencing primer to the nucleic acid molecules of at least two different template nucleic acid molecules, or at least two different substantially monoclonal populations. In some embodiments, the sequencing includes incorporating a nucleotide onto the 3' OH of the sequencing primer using the polymerase. Optionally, the incorporating includes forming at least one nucleotide incorporation byproduct.

In the embodiments of the present disclosure involving distribution of template nucleic acid molecules into the wells of an isFET array and subsequent amplification of templates inside the wells of the array, an optional step of downstream analysis is performed after the amplification that quantifies the number of sites or wells that include amplification product. In some embodiments, the products of the nucleic acid amplification reactions are detected in order to count the number of sites or wells that include an amplified template. In some embodiments, after the amplification, at least 50%, 55%, 60%, 65%, 70%, 75%, 80%, 85%, 90%, 95%, 96%, 97%, 98%, 99% or 100% of the wells includes a substantially monoclonal population of template nucleic acid molecules.

In some embodiments, the templated supports are distributed into distributed into separate reaction chambers (e.g., an array of wells) for sequencing. In some embodiments, at least 25%, 30%, 35%, 40%, 45%, 50%, 55%, 60%, 65%, 70%, 75%, 80%, 85%, 90%, or 95% of the reaction chambers have a templated support with substantially monoclonal populations of template nucleic acid molecules. In some embodiments, between about 25% and 95% of the reaction chambers have a templated support with substantially monoclonal populations of template nucleic acid molecules, for example between about 25% and 85%, between about 25% and 75%, between about 35% and 95%, between about 35% and 85%, between about 35% and 75%, between about 45% and 95%, between about 45% and 85%, between about 45% and 75%, between about 55% and 95%, between about 55% and 85%, between about 55% and 75%, between about 65% and 95%, between about 65% and 85%, between about 65% and 75%, between about 75% and 95%, between about 75% and 85%, or between about 85% and 95% of the reaction chambers have a templated support with substantially monoclonal populations of template nucleic acid molecules. In some embodiments, the separate reaction chambers are wells on a sequencing chip. In some embodiments, no more than 1%, 2%, 3%, 4%, 5%, 10%, 15%, 20% or 25% of the wells give low quality results, where low quality wells are determined by the sequencing method.

In various embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a template nucleic acid molecule, which may be a fragment of a nucleic acid sequence of interest, for example, and which may be directly or indirectly attached as a substantially monoclonal population of nucleic acid molecules on a support, such as a particle, microparticle, bead, etc. The sample or template nucleic acid may be operably associated to a primer and polymerase and may be subjected to repeated cycles or "flows" of nucleotide addition (which may be referred to herein as "nucleotide flows" from which nucleotide incorporations may result) and washing. The primer may be annealed to the sample or template so that the 3' end of the primer is extended by a polymerase whenever nucleotides complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

In the templating reaction, a sufficient number of substantially monoclonal or monoclonal populations can be produced to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. With respect to related high-throughput systems, a sufficient number of substantially monoclonal or monoclonal amplicons can be produced in a single amplification reaction to generate at least 100 MB, 200 MB, 300 MB, 400 MB, 500 MB, 750 MB, 1 GB, 2 GB, 5 GB, 10 GB or 15 GB of AQ20 sequencing reads on an Ion Torrent Proton, S5 or S5XL sequencer. The term "AQ20" and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores are useful to filter and remove lower quality reads prior to downstream alignment. In some embodiments, the accuracy is reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction is filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy is calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction is filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the present disclosure provides kits for nucleic acid amplification in a pre-seeding reaction followed by a templating reaction. The compositions discussed herein are also amendable to kit format wherein the primers, and amplification components may be in the same container, separate containers and in liquid or dehydrated form. The kit can include instructions for performing the methods for amplification of template nucleic acid molecules including a pre-seeding reaction for downstream sequencing methods. In one embodiment, the kit provides instructions for nucleic acid sequencing preparation.

In some embodiments, a kit that includes at least two containers, at least one of which includes a primer and at least one of which includes a recombinase. The recombinase and the primer can be in the same or different tubes. In some embodiments, at least one primer is attached to one or more supports. The kits can further include one or more pre-seeded solid supports.

In some embodiments, the container including the recombinase further include one or more amplification reagents including a recombinase accessory protein, a polymerase, dNTPs, and a buffer. In certain embodiments, the kit includes one or more containers with uvsX recombinase, uvsY recombinase loading protein, gp32 protein, Sau DNA polymerase, dNTPs, ATP, phosphocreatine, and creatine kinase.

In some embodiments, the kits include any combination of: one or more solid supports, optionally with a population of at least one primer attached, polynucleotides, recombinase, recombinase loading protein, single-stranded binding protein (SSB), polymerase, nucleotides, ATP, phosphocreatine, creatine kinase, hybridization solutions, washing solutions, buffers and/or cations (e.g., divalent cations). A kit can include all or some of these components, typically in at least two separate vessels. The kit can include any of the components of pre-seeding reaction mixtures or templating reaction mixtures.

In certain embodiments, provided is a method for generating a nucleic acid template comprising a specific nucleotide sequence, comprising obtaining a population of nucleic acid molecules in which each molecule comprises a first sequence of contiguous nucleotides at the 5' end of the molecule, a second sequence of contiguous nucleotides at the 3' end of the molecule and a third nucleotide sequence positioned between the first and second nucleotide sequences, wherein the first nucleotide sequence and second nucleotide sequence are different from each other, and wherein the first nucleotide sequences of the nucleic acid molecules are substantially identical and the second nucleotide sequences of the nucleic acid molecules are substantially identical among the population; subjecting the population of nucleic acid molecules to a cycle of nucleic acid amplification in the presence of a forward primer and a reverse primer, wherein the forward primer comprises an oligonucleotide sequence substantially identical to the first nucleotide sequence and the reverse primer comprises an oligonucleotide sequence complementary to a subsequence of the 5' end of the second nucleotide sequence that is linked at the 3' end of the subsequence to a fourth nucleotide sequence that is not complementary to the second nucleotide sequence; and subjecting the products of the cycle of amplification of (b) to a cycle of amplification in the presence of the forward and reverse primers to generate multiple different nucleic acid products; wherein the reverse primer includes a nucleotide sequence complementary to the 5' end of the second nucleotide sequence but does not contain a nucleotide sequence complementary to the 3' end of the second nucleotide sequence, and only one of the products comprises a sequence of nucleotides complementary to the fourth nucleotide sequence. In some embodiments the forward primer comprises a modified nucleotide containing an attachment thereto. In some embodiments the attachment to the modified nucleotide comprises biotin. In some embodiments the method further comprises combining the single-stranded nucleic acids of the products to a single-stranded oligonucleotide that is substantially identical to the fourth nucleotide sequence under annealing conditions thereby hybridizing the product that comprises a sequence of nucleotides complementary to the fourth nucleotide sequence to the single-stranded oligonucleotide that is substantially identical to the fourth nucleotide sequence to generate a partially double-stranded oligonucleotide-bound product. In some embodiments the single-stranded oligonucleotide that is substantially identical to the fourth nucleotide sequence is attached to a support. In some embodiments the support is a solid support. In particular embodiments the support is a particle or bead. In some embodiments the method further comprises extending the 3' end of the oligonucleotide that is hybridized to the product that comprises a sequence of nucleotides complementary to the fourth nucleotide sequence thereby generating a double-stranded nucleic acid by synthesizing a nucleic acid strand comprising the single-stranded oligonucleotide that is substantially identical to the fourth nucleotide sequence and having a nucleotide sequence that is complementary to the product to which it is hybridized. In some embodiments the method further comprises separating the strands of the double-stranded nucleic acid. In some embodiments the nucleic acid strand comprising the single-stranded oligonucleotide that is substantially identical to the fourth nucleotide sequence is attached to a support at the 5' end of the strand through the portion of the strand that is the oligonucleotide sequence. In some embodiments the method further comprises isolating the nucleic acid strand attached to the support by removing the support from any other nucleic acids that are not bound to the support.

In certain aspects, provided is a method for generating nucleic acid molecules comprising a specific nucleotide sequence, comprising obtaining a population of nucleic acid molecules in which each molecule comprises a first sequence of contiguous nucleotides at the 5' end of the molecule, a second sequence of contiguous nucleotides at the 3' end of the molecule and a third nucleotide sequence positioned between the first and second nucleotide sequences, wherein the first nucleotide sequence and second nucleotide sequence are different from each other, and wherein the first nucleotide sequences of the nucleic acid molecules are substantially identical and the second nucleotide sequences of the nucleic acid molecules are substantially identical among the population, and subjecting the population of nucleic acid molecules to two or more cycles of nucleic acid amplification in the presence of one or more forward primers comprising an oligonucleotide sequence substantially identical to the first nucleotide sequence and a reverse primer that is blocked at the 3' end and comprises an oligonucleotide sequence complementary to the second nucleotide sequence that is linked at the 5' end of the oligonucleotide sequence to a fourth nucleotide sequence that is not complementary to the second nucleotide sequence to generate nucleic acid products in which substantially all of the products comprise a sequence of nucleotides complementary to the fourth nucleotide sequence. In some embodiments the forward primer comprises a modified nucleotide containing an attachment thereto. In some embodiments the attachment to the modified nucleotide comprises biotin. In some embodiments the method further comprises exposing single-stranded nucleic acids of the products of (b) to a single-stranded oligonucleotide that is substantially identical to the fourth nucleotide sequence under annealing conditions thereby hybridizing the products of (b) that comprise a sequence of nucleotides complementary to the fourth nucleotide sequence to the single-stranded oligonucleotide that is substantially identical to the fourth nucleotide sequence to generate a partially double-stranded oligonucleotide-bound product. In some embodiments the single-stranded oligonucleotide that is substantially identical to the fourth nucleotide sequence is attached to a support. In some embodiments the support is a solid support. In certain embodiments the support is a particle or bead. In some embodiments the method further comprises extending the 3' end of the oligonucleotide that is hybridized to the product that comprises a sequence of nucleotides complementary to the fourth nucleotide sequence thereby generating a double-stranded nucleic acid by synthesizing a nucleic acid strand comprising the single-stranded oligonucleotide that is substantially identical to the fourth nucleotide sequence and having a nucleotide sequence that is complementary to the product to which it is hybridized. In some embodiments the method further comprises separating the strands of the double-stranded nucleic acid. In some embodiments the nucleic acid strand comprising the single-stranded oligonucleotide that is substantially identical to the fourth nucleotide sequence is attached to a support at the 5' end of the strand through the portion of the strand that is the oligonucleotide sequence. In some embodiments the method further comprises isolating the nucleic acid strand attached to the support by removing the support from any other nucleic acids that are not bound to the support.

In one aspect, provided is a templating reaction mixture comprising a population of pre-seeded solid supports, nucleotides, a recombinase, and a polymerase, wherein the population of pre-seeded solid supports comprise between 10 and 50,000 substantially monoclonal template nucleic acid molecules comprising a first primer attached thereto and further comprise attached first primers not bound to template nucleic acid molecules, wherein the reaction mixture does not comprise a cation capable of initiating a recombinase-polymerase amplification reaction, and wherein at least 95% of the template nucleic acid molecules in the reaction mixture are attached to the one or more pre-seeded solid supports. In some embodiments the template nucleic acid molecules comprise two or more template nucleic acid molecules with different sequences. In some embodiments the substantially monoclonal template nucleic acid molecules comprise a proximal segment having 20 to 50 identical nucleotides attaching a template nucleic acid molecule to a solid support. In some embodiments the substantially monoclonal template nucleic acid molecules comprise fewer than 100 identical nucleotides at a proximal segment attaching a template nucleic acid molecule to a solid support. In some embodiments the pre-seeded solid supports are pre-seeded beads. In some embodiments each pre-seeded solid support of the population of pre-seeded solid supports has between 10 and 10,000 substantially monoclonal template nucleic acid molecules attached thereto and wherein the one or more pre-seeded solid supports are beads. In some embodiments less than 10% of the substantially monoclonal template nucleic acid molecules on each pre-seeded solid support comprise 50-100 identical nucleotides attaching them to the pre-seeded solid support. In some embodiments the templating reaction mixture further comprises a recombinase-accessory protein. In some embodiments the recombinase-accessory protein is a single-stranded binding protein and/or a recombinase-loading protein. In some embodiments the pre-seeded solid supports are generated using a first recombinase-polymerase amplification (RPA) reaction. In some embodiments the first RPA reaction is performed by incubating an RPA reaction mixture for 2 to 5 minutes at a temperature between 35° C. and 45° C. In some embodiments the pre-seeding reaction mixture further comprises a population of identical second primers in solution, and wherein the template nucleic acid molecules comprise a primer binding site for the first primer at or near a first terminus. In some embodiments the reaction mixture further comprises a cation capable of initiating the recombinase-polymerase amplification reaction.

In another aspect of the invention, provided is a method of generating one or more template nucleic acid populations on a solid support, comprising: a) obtaining a population of nucleic acid molecules wherein each molecule comprises a first adapter sequence of contiguous nucleotides at the 5' end of the molecule, a second adapter sequence of contiguous nucleotides at the 3' end of the molecule and a third nucleotide sequence positioned between the first and second nucleotide sequences, wherein the first adapter nucleotide sequence and the second adapter nucleotide sequence are different; wherein the first adapter nucleotide sequences of the nucleic acid molecules are substantially identical, the second adapter nucleotide sequences of the nucleic acid molecules are substantially identical, and the nucleotide sequence positioned between the first and second nucleotide sequences differ among the population; and wherein the first adapter nucleotide sequence comprises a first linker moiety attached thereto; b) generating single strands of the population of nucleic acid molecules and contacting the single-stranded nucleic acids with solid supports under annealing conditions to generate solid supports having single-stranded nucleic acids attached thereto through hybridization with the second adapter sequence of the nucleic acids, wherein the solid supports comprise a plurality of primer oligonucleotides having a nucleotide sequence complementary to the second adapter sequence of the nucleic acids immobilized thereto; c) extending the immobilized primers of the solid support that are hybridized to a nucleic acid strand to generate double-stranded nucleic acids bound to the solid supports; d) subjecting the nucleic acid molecules bound to the solid supports to a cycle of nucleic acid amplification in the presence of a first primer comprising an oligonucleotide sequence substantially identical to the first adapter nucleotide sequence and a linker moiety attached thereto, wherein a limited number of single-stranded nucleic acids attach to each solid support, and the nucleic acids attached to an individual support are substantially monoclonal; e) combining the solid supports having nucleic acids bound thereto with magnetic beads comprising a second linking moiety to which the first linking moiety attaches to generate solid support-magnetic bead assemblies; f) applying a magnetic field to the bead assemblies thereby separating the bead assemblies from elements that do not include a magnetic bead; g) releasing the solid supports having nucleic acids attached thereto from the magnetic beads; h) combining the solid supports having nucleic acids attached thereto with magnetic beads wherein the nucleic acids on the solid supports will not attach to the magnetic beads; i) delivering the combined solid supports having nucleic acids attached thereto and magnetic beads to a surface comprising microwells and applying a magnetic field to the surface whereby the solid supports having nucleic acids attached thereto are loaded into separate microwells; and j) subjecting the nucleic acid molecules bound to the solid supports in the microwells to at least one cycle of nucleic acid amplification in the presence of a first primer in solution, wherein the first primer comprises an oligonucleotide sequence substantially identical to the first adapter nucleotide sequence and wherein the amplification generates at least 10-fold more nucleic acids attached to the solid support than were attached after the amplification set out in (d); wherein the reverse primer includes a nucleotide sequence complementary to the 5' end of the second nucleotide sequence but does not contain a nucleotide sequence complementary to the 3' end of the second nucleotide sequence. In some embodiments the number of solid supports in (b) exceeds the number of nucleic acid molecules by a factor of at least 2. In some embodiments the number of solid supports in (b) exceeds the number of nucleic acid molecules by a factor of at least 5. In some embodiments the amplification in (j) generates at least 100,000-fold more nucleic acids attached to the solid support than were attached after the amplification in (d). In some embodiments the amplification in (j) generates at least 1,000,000-fold more nucleic acids attached to the solid support than were attached after the amplification in (d). In some embodiments the method further comprises subjecting the amplified nucleic acids attached to the solid supports to nucleic acid sequencing. In some embodiments the sequencing process produces at least 60 million sequence reads which are at least 300 nucleotides in length. In some embodiments the sequencing process produces at least 80 million sequence reads which are at least 100 nucleotides in length. In some embodiments the sequencing process produces at least 80 million sequence reads between about 100 and about 400 nucleotides in length.

In another aspect, provided is a method of generating one or more template nucleic acid populations on a solid support, comprising: a) obtaining a population of nucleic acid molecules in which each molecule comprises a first adapter sequence of contiguous nucleotides at the 5' end of the molecule, a second adapter sequence of contiguous nucleotides at the 3' end of the molecule and a third nucleotide sequence positioned between the first and second nucleotide sequences, wherein the first adapter nucleotide sequence and the second adapter nucleotide sequence are different and the first adapter nucleotide sequences of the nucleic acid molecules are substantially identical and the second adapter nucleotide sequences of the nucleic acid molecules are substantially identical and wherein the first adapter nucleotide sequence is modified to comprise a first linker moiety attached thereto; b) generating single strands of the population of nucleic acid molecules and contacting the single-stranded nucleic acids with solid supports under annealing conditions to generate solid supports having single-stranded nucleic acids attached thereto through hybridization with the second adapter sequence of the nucleic acids, wherein the solid supports comprise a plurality of primer oligonucleotides having a nucleotide sequence complementary to the second adapter sequence of the nucleic acids immobilized thereto and the number of solid supports exceeds the number of nucleic acid molecules by a factor of at least 5. c) transferring the solid supports having nucleic acids attached thereto to a surface comprising microwells whereby the solid supports having nucleic acids attached thereto are individually loaded into separate microwells; d) extending the immobilized primers of the solid support that are hybridized to a nucleic acid strand to generate double-stranded nucleic acids bound to the solid supports; e) subjecting the nucleic acid molecules bound to the solid supports to a cycle of nucleic acid amplification in the presence of a first primer in solution, wherein (1) the first primer comprises an oligonucleotide sequence substantially identical to the first adapter nucleotide sequence and is modified to comprise a linker moiety attached thereto, (2) the amplification generates a limited number of additional single-stranded nucleic acids attached to the solid supports through hybridization between the primer oligonucleotides having a nucleotide sequence complementary to the second adapter sequence immobilized on the solid supports and the second adapter sequence of the nucleic acids, (3) the nucleic acids attached to an individual support are substantially monoclonal, and (4) the amplification is conducted in the presence of a composition that attaches to the linker moiety of the first adapter; f) stopping the amplification of (e) and removing the composition that attaches to the linker moiety of the first adapter from the microwells; and g) subjecting the nucleic acid molecules bound to the solid supports in the microwells to at least one cycle of nucleic acid amplification in the presence of a first primer in solution, wherein the first primer comprises an oligonucleotide sequence substantially identical to the first adapter nucleotide sequence and wherein the amplification generates at least 1000-fold more nucleic acids attached to the solid support than were attached after the amplification of step (e); wherein the reverse primer includes a nucleotide sequence complementary to the 5' end of the second nucleotide sequence but does not contain a nucleotide sequence complementary to the 3' end of the second nucleotide sequence and the nucleic acids attached to an individual support are substantially monoclonal.

In another aspect, provided is a method of preparing a device for nucleic acid analysis, the method comprising: generating a template nucleic acid including a capture sequence portion, a template portion, and primer portion modified with a linker moiety; capturing the template nucleic acid on a bead support having a plurality of capture primers complementary to the capture sequence portion of the template nucleic acid, the capture primers hybridizing to the capture sequence portion of the template nucleic acid; linking the captured template nucleic acid to a magnetic bead having second linker moiety to form a bead assembly, the second linker moiety attaching to the first linker moiety; and loading the bead assembly into a well of the sequencing device using a magnetic field. In some embodiments the method further comprises extending the capture primer complementary to the template nucleic acid to form a sequence target nucleic acid attached to the bead support. In some embodiments the method further comprises denaturing the template nucleic acid and the sequence target nucleic acid to release the magnetic bead from the bead support. In certain embodiments denaturing includes enzymatic denaturing. In certain embodiments denaturing includes denaturing in the presence of an ionic solution. In some embodiments the method further comprises washing the magnetic bead from the sequencing device. In some embodiments the method further comprises amplifying the sequence target nucleic acid to form a population of sequence target nucleic acids on the bead support in the well. In some embodiments amplifying include performing recombinase polymerase amplification (RPA). In some embodiments performing RPA includes performing RPA for a first period, washing, and performing RPA for a second period, the first period shorter than the second period. In some embodiments generating includes extending a linker modified primer complementary to a target nucleic acid. In certain embodiments generating comprises amplifying a target nucleic acid having a first primer portion, a target portion, and a second primer portion in the presence of a bead support having a capture primer, a linker modified first primer complementary to the first primer portion, and a second primer having a portion complementary to at least a portion of the second primer portion, the second primer having a capture primer portion ligated to the portion and complementary to the capture primer, wherein the bead support capture primer is extended to include a sequence of the target nucleic acid. In some embodiments amplifying includes performing three polymerase chain reaction (PCR) cycles.

In another aspect, provided is a method of preparing a sequencing device, the method comprising: generating a template nucleic acid including a capture sequence portion, a template portion, and primer portion; capturing the template nucleic acid on a bead support coupled to a capture primer complementary to the capture sequence portion, the capture primer hybridizing to the capture sequence portion of the template nucleic acid; extending the capture primer complementary to the template nucleic acid to form a target nucleic acid complementary to and hybridized to the template nucleic acid; denaturing to separate the hybridized template nucleic acid and the target nucleic acid; hybridizing a linker modified primer to the target nucleic acid on the bead support, the linker modified primer including a linker moiety; extending the linker modified primer complementary to the target nucleic acid; coupling a magnetic bead to the linker moiety, the magnetic bead having a second linker moiety attaching to the linker moiety; and depositing the bead support into a well of a sequencing device using a magnetic field. In some embodiments the method further comprises denaturing the template nucleic acid and the sequence target nucleic acid to release the magnetic bead from the bead support. In some embodiments denaturing includes enzymatic denaturing. In some embodiments denaturing includes denaturing in the presence of an ionic solution. In some embodiments the method further comprises washing the magnetic bead from the sequencing device. In some embodiments the method further comprises amplifying the sequence target nucleic acid to form a population of sequence target nucleic acids on the bead support in the well. In some embodiments amplifying include performing recombinase polymerase amplification (RPA). In some embodiments performing RPA includes performing RPA for a first period, washing, and performing RPA for a second period, the first period shorter than the second period. In some embodiments generating includes extending a linker modified primer complementary to a target nucleic acid. In some embodiments the extending includes performing polymerase chain reaction (PCR).

The following examples are put forth so as to provide those of ordinary skill in the art with a complete disclosure and description of how to use the embodiments of the present teachings, and are not intended to limit the scope of the disclosure nor are they intended to represent that the Examples below are all of the experiments or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

EXAMPLES

Example 1

Pre-Seeding P1 Ion Sphere Particles (ISPs) with a Single-Cycle PCR Before Bulk Isothermal Amplification This example provides a method to pre-seed ISPs with monoclonal templates before isothermal amplification for downstream next-generation sequencing. These pre-seeded ISPs require no additional templates in solution during the isothermal amplification step and are able to generate templates that produce better sequencing results than ISPs with no pre-seeded template (non-template control or "NTC"). Ion Torrent ISPs with forward P1 adapters ("P1 ISPs") were pre-seeded with different copy numbers of monoclonal templates and amplified in bulk isothermal amplification ("Bulk IA"). The pre-seeded ISPs were compared to no template control ("NTC") ISPs, which had the same template polynucleotides added during the templating reaction instead of during the pre-seeding reaction before the templating reaction. Sequencing results from the different amplification reactions were compared using various metrics.

Generating Template Nucleic Acid Molecules

DNA was amplified from genomic DNA using PCR primers 1, 12, and 13 from the Oncomine Focus Assay (OFA) (Thermo Fisher Scientific, Waltham, Mass.). Adapters that facilitated binding to immobilized primer B and a primer A in solution used in the seeding reaction, were added to the amplicons during 10 cycles of a second tailed PCR. The amplification generated 3 templates: OFA 1 AB, 19.2 ng/µl (148 nM); OFA 12 AB, 15.6 ng/µl (100 nM); and OFA 13 AB, 17.2 ng/µl (76 nM).

Pre-Seeding Reaction

Dilutions of the OFA 1 AB, OFA 12 AB, and OFA 13 AB templates were made and used to generate separate pre-seeded P1 ISPs in a pre-seeding reaction. The pre-seeding reaction included 6.67 µl P1 ISPs with immobilized primer B (400,000,000 ISPs), 88.33 µl 1× Platinum HiFi Mix (Thermo Fisher Scientific, Waltham, Mass.), and 5 µl of the appropriate template dilution to generate a desired number of substantially monoclonal template molecules (copy numbers 70, 665, and 4,170 for P1 ISPs). The ISP pre-seeding reaction mixtures were placed in a thermocycler for a denaturation step of 98° C. for 2 min followed by 98° C. for 25 sec and 56° C. for 10 min to generate pre-seeded ISPs. To check the relative sizes of the ISPs, 1 µl of each of the pre-seeded P1 ISPs was diluted in 999 µl Annealing Buffer (Ion PGM™ Hi-Q™ View Sequencing Solutions, (Part No. A30275)) and analyzed using a Guava easyCyte Flow Cytometer (EMD Millipore, Billerica, Mass.). The NTC P1 ISPs were also analyzed for relative size in the absence of bound template.

The remaining pre-seeded P1 ISPs were washed twice in Ion OneTouch Wash Solution wash buffer in a total volume of 1 ml. After the first wash, the samples were centrifuged at >21,000 g for 8 min and the supernatant was removed to leave ~100 µl. After the second wash and centrifugation, the supernatant was removed to leave ~50 µl sample in the tube. The sample was then treated with 300 µl of freshly prepared melt off solution (125 mM NaOH, 0.1% Tween 20) and thoroughly vortexed before incubation for 5 minutes at room temperature. These samples were then washed three times with nuclease-free (NF) $H_2O$ in a final volume of 1 ml. After each wash, the samples were centrifuged at >21,000 g for 8 mM and the supernatants were removed to leave ~100 µl. To check the size of the pre-seeded P1 ISPs after the last wash, 1 µl of each of the pre-seeded P1 ISPs was diluted in 99 µl Annealing Buffer and analyzed using a Guava easyCyte Flow Cytometer. The NTC P1 ISPs were also analyzed for relative size in the absence of bound template.

Determining the Numbers of Copies on the Pre-Seeded P1 ISPs

Based on the counts from the Guava easyCyte Flow Cytometer of the samples after washing, dilutions were made of the pre-seeded P1 ISPs to give 50,000, 5,000, 500, or 50 ISPs/µl. These dilutions were used in a qPCR reaction as follows: 10 µl Fast SYBR (Thermo Fisher Scientific, Waltham, Mass.), 0.2 µl 10 µM Truncated PCR A Primer (5' CCA TCT CAT CCC TGC GTG TC 3'; SEQ ID NO: 2), 0.2 µl 10 µM Truncated PCR B Primer (5'-CCT ATC CCC TGT GTG CCT TG-3'; SEQ ID NO: 3), 2 µl pre-seeded P1 ISPs, and 7.6 µl NF $H_2O$. The reaction mixes were placed in a real-time PCR instrument for a denaturation step of 95° C. for 20 sec followed by 40 cycles of 95° C. for 3 sec and 60° C. for 30 sec. The $C_t$ of each qPCR reaction was compared to $C_t$ values of qPCR reactions with known numbers of molecules to calculate the number of copies of monoclonal template on each ISP. Samples with the same amount of template pre-seeded were combined to obtain an average number of copies per ISP for each group.

Templating Reaction

The pre-seeded P1 ISPs with the same number of copies of each monoclonal template were pooled, i.e. the P1 ISPs that had been pre-seeded with 70 copies of OFA 1 AB, OFA 12 AB, or OFA 13 AB were all pooled and similarly the P1 ISPs pre-seeded with 665 copies of the templates were pooled and the P1 ISPs pre-seeded with 4,170 copies of the templates were pooled. The pools of pre-seeded P1 ISPs (100 μl containing ~375,000,000 pre-seeded P1 ISPs) were combined with 4 μl Primer Mix S (Ion PGM™ Template IA 500 Kit, ThermoFisher Scientific) in solution not attached to any substrate, wherein the template nucleic acid molecules include a primer binding site for the second primer at or near the terminus opposite the proximal segment) and 146 ISP Dilution Buffer, both from the Ion PGM™ Template IA 500. The NTC P1 ISPs (100 μl containing 375,000,000 ISPs) were combined with 4 μl Primer Mix S, 131 μl ISP Dilution Buffer, and three 5 μl aliquots of the library. Two Ion PGM™ Template IA (isothermal amplification) pellets were rehydrated, each with 720 μl Rehydration Buffer, vortexed, and briefly spun. Dehydrated Template IA pellets contained T7 polymerase, uvsX recombinase, uvsY recombinase loading protein, gp32 protein, Bsu DNA polymerase, dNTPs, ATP, thioredoxin, phosphocreatine, and creatine kinase. Four pellets from a TwistAmp™ Basic kit were rehydrated in 120 μL of Rehydration Buffer (25 mM Tris, pH 8.3; 5 mM DTT; 3 mM dNTP; 3.5625% Trehalose; 0.1 mg/ml Creatine Kinase; 1.1375 mg/ml Twist gp32; 0.4 mg/ml UvsX; 0.1 mg/ml UvsY; 0.25 mU/ul PPiase; 0.02 mg/ml Sau Pol; 0.03063 mg/ml T7 Dbl Exo-Pol; 0.0225 mg/ml Thioredoxin (5×); 1.425% PEG 35) supplied from the kit (tube 2). The recombinase solution was vortexed and spun, then iced. To each pool of pre-seeded P1 ISPs and the NTC ISPs, 360 μl of the rehydrated pellet solution were add. The solutions were thoroughly vortexed and briefly spun. The templating reaction was performed at 40° C. for 30 minutes. To stop the templating reaction, 650 μl of 100 mM EDTA was added, the solution was vortexed, and the tubes were briefly spin.

Enriching the Templated ISPs

The templated ISPs were enriched using MyOne beads (ThermoFisher Scientific, Waltham, Mass.). Briefly, each stopped templating reaction was split into 2 tubes and 100 μl of MyOne beads were added to each tube. The tube was rotated for 15 minutes at room temperature, spun, and placed on a magnetic tube rack. After the beads were fully pelleted, the supernatant was removed and discarded. Then, like samples were pooled using 500 μl 3 mM SDS solution per tube such that each like-sample set had a total of 1 ml 3 mM SDS. The tubes were vortexed thoroughly, briefly spun, and placed on a magnetic tube rack for 2 minutes. The supernatant was removed and the tubes were removed from the magnetic tube rack. The beads were resuspended with 200 μl of melt-off solution (125 mM NaOH and 0.1% Tween 20), vortexed thoroughly, and briefly spun. After a 2 minute room temperature incubation, the bead solution was placed on a magnetic tube rack for 2 minutes and the supernatant was transferred to a new 0.2 ml tube. The tube was spun for 8 minutes at maximum speed and the supernatant was removed to leave ~10-15 μl solution. 90 μl water was added to the templated ISPs and 2 μl was removed for analysis on a Guava easyCyte Flow Cytometer. The tube was spun for 5 minutes at 15,000 rcf and the supernatant was removed to leave 10 μl of solution containing the templated ISPs. 20 μl of 100% PBST and 20 μl of sequencing primer were added to the ISPs and the tubes were vortexed and spun briefly. The sequencing primer was annealed according to the manufacturer's instructions using the Ion Torrent PI™ Sequencing HiQ 200 Kit (Life Technologies, Carlsbad, Calif.).

Sequencing

A standard sequencing reaction was conducted on an Ion Torrent PGM according to the manufacturer's instructions using an Ion Torrent PI™ Sequencing HiQ 200 Kit (Life Technologies, Carlsbad, Calif.). The sequencing signals were analyzed by Torrent Suite Software to determine the sequence present within the amplicon of these ISPs.

Results

Figure 2A:
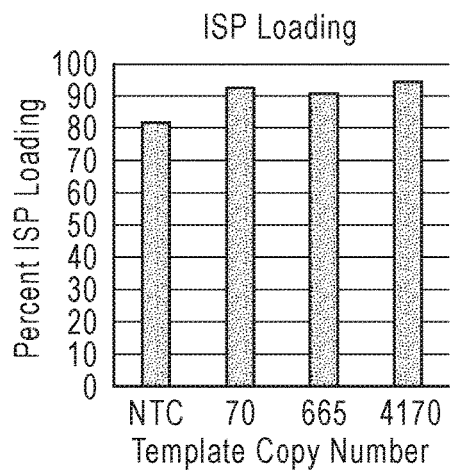
FIGS. 2A-2F are bar graphs showing various metrics of high-throughput sequencing after bulk isothermal amplification using NTC P1 ISPs and ISPs pre-seeded with ~70, ~665, and ~4,170 copies/ISP.
Figure 2B:
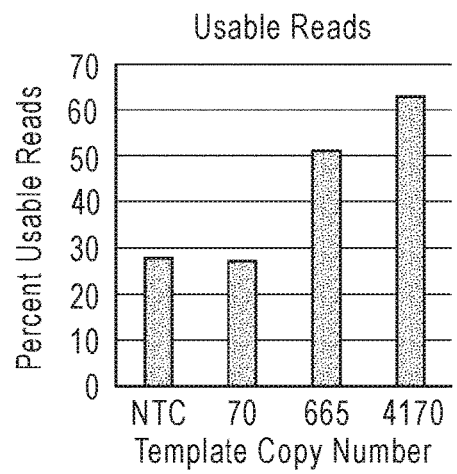
Figure 2C:
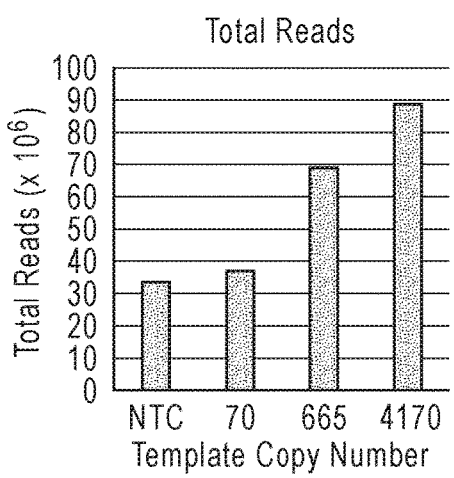
Figure 2D:
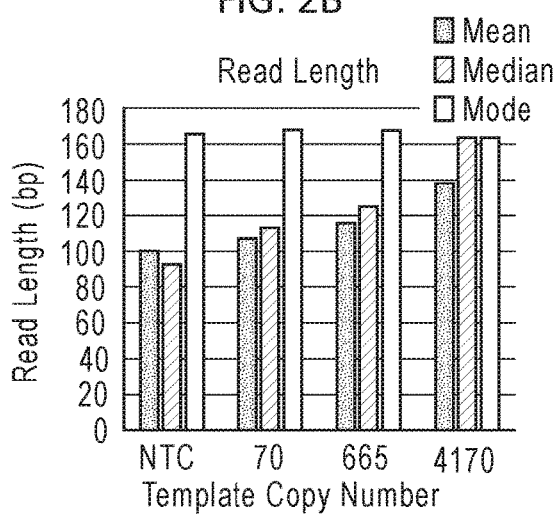
Figure 2E:
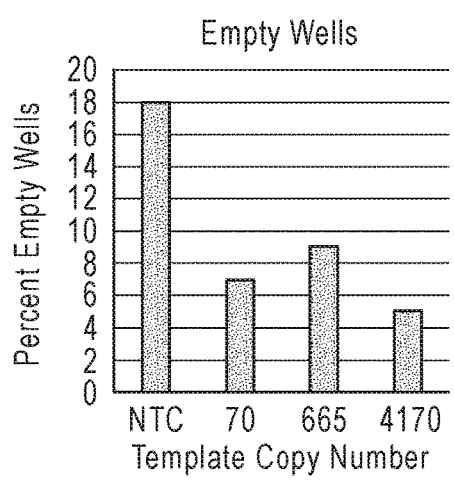
Figure 2F:
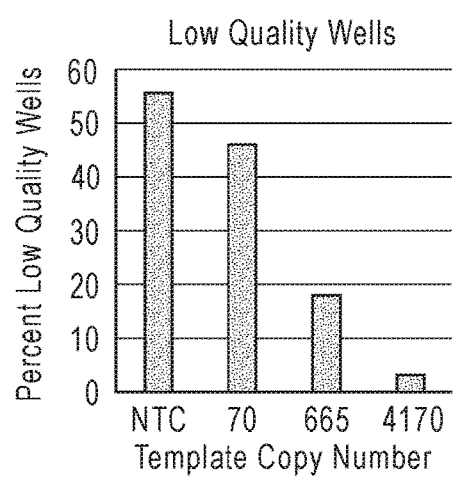

Pre-seeding the P1 ISPs with monoclonal templates before Bulk IA generated better sequencing metrics than similar reactions without pre-seeding (i.e. NTC P1 ISPs). Furthermore, the P1 ISPs pre-seeded with more copies of the monoclonal templates up to 4170, the largest number tested in this example, had better sequencing metrics than ISPs pre-seeded with fewer copies. For example, read length histograms illustrated that the pre-seeded samples had fewer small length reads (FIGS. 1A-1D). Furthermore, the percentages of ISPs loaded and the usable reads from these loaded ISPs both increased with higher numbers of copies pre-seeded onto ISPs (FIGS. 2A-2B). The total reads and mean and median of the read lengths also increased with number of copies pre-seeded (FIGS. 2C-2D). Negative metrics of sequencing were reduced with pre-seeding in a copy number dependent manner. For example, the percentages of empty wells and low quality wells were reduced with pre-seeded P1 ISPs (FIGS. 2E-2F). Overall, this experiment demonstrates P1 ISPs can be pre-seeded a monoclonal template before Bulk IA to provide significant improvements in next-generation sequencing.

Example 2

Pre-Seeding ISPs with a Single-Cycle PCR Followed by Isothermal Amplification

As in the previous example, this example provides a method to pre-seed ISPs with monoclonal templates before an isothermal amplification (templating reaction) for downstream next-generation sequencing. However, in the method disclosed in this example, the templating reaction was performed after pre-seeded ISPs were distributed into wells of an Ion Torrent chip. The pre-seeded ISPs were compared to no template control ("NTC") ISPs, which had the same template polynucleotides in solution during the templating reaction instead of before the templating reaction and during the pre-seeding reaction. Sequencing results from the different amplification reactions were compared using various metrics.

Pre-Seeding Reaction

Accordingly, ISPs with P1 adapters were pre-seeded with OFA 1 AB, OFA 12 AB, or OFA 13 AB template nucleic acid molecules as provided in Example 1. After pre-seeding, the pre-seeded ISPs were washed and counted as provided in Example 1. The pre-seeded ISPs with the same number of copies of each monoclonal template were pooled, i.e. the ISPs that had been pre-seeded with 82 copies of OFA 1 AB, OFA 12 AB, or OFA 13 AB were all pooled and similarly the ISPs pre-seeded with 775 copies of the templates were pooled and the ISPs pre-seeded with 5,400 copies of the templates were pooled.

Cassette Loading

Ion Torrent 541 chips were washed with 100 µl of 100 mM NaOH for 60 seconds, rinsed with 200 µl nuclease-free water, rinsed with 200 µl isopropyl alcohol, and aspirated dry. To load the chip, ISPs (500,000,000 NTC ISPs or pooled, pre-seeded ISPs) were vortexed, brought to 45 µl with Annealing Buffer (Ion PI™ Hi-Q™ Sequencing 200 Kit, Ion Torrent), and injected into the treated chip through the loading port. The chip was centrifuged for 2 minutes at 1424 rcf. 1 ml of foam (980 µl 50% Annealing Buffer with 20 µl 10% Triton X-100 were combined, 1 ml of air was pipetted in, and foam was further mixed by pipette for 5 seconds) was injected into the chip and the excess was aspirated. 200 µl of a 60% Annealing Buffer/40% isopropyl alcohol flush solution was injected into the chip and the chip was aspirated to dryness. The chip was rinsed with 200 µl Annealing Buffer and the chip was vacuumed dry. For the chips with pre-seeded ISPs, 40 µl of PBST was added to the chip and each port was filled with 35 µl PBST. For the chip with NTC ISPs, 5 µl of 100 µM library (equal parts OFA 1 AB, OFA 12 AB, and OFA 13 AB) was added to 110 µl Annealing Buffer to make a library mix. 40 µl of the library mix was added to the chip and each port was filled with 35 µl library mix. The chips were placed on a thermocycler and cycled one time at 95° C. for 1 minute, then 37° C. for 2 minutes, then 4° C. The chips were rinsed once with 200 µl Annealing Buffer and left wet.

Templating Reaction

An Ion PGM™ Template IA Pellet was rehydrated with 871 µl of Ion PGM™ Rehydration Buffer, vortexed thoroughly, and spun briefly. Each chip was injected with 40 µl pellet IA solution and the displaced Annealing Buffer was aspirated from the exit port. 20 µl pellet IA solution was added to the loading port and the chips were spun for 2 minutes at 1424 rcf. To activate the pellet IA solution, 218.2 µl Ion PGM™ Start Solution was combined with 8 µl Primer A and added to the pellet IA solution. The activated pellet IA solution was vortexed and spun briefly. To each chip, 60 µl of activated pellet IA solution was injected and the displaced fluid was aspirated. Each chip had an additional 35 µl of pellet IA solution added to each port. The chips were placed on a thermocycler set to 40° C., covered, and incubated for 15 minutes. The chips were rinsed with 200 µl 0.5 M EDTA under vacuum and aspirated dry. The chips were rinsed with 200 µl Annealing Buffer under vacuum and aspirated dry. The chips were rinsed twice with 200 µl 1% SDS under vacuum and aspirated dry. The chips were rinsed with 200 µl Flush solution (50% isopropyl alcohol/50% Annealing Buffer) under vacuum and aspirated dry. Then the chips were rinsed with 200 µl Annealing Buffer and aspirated dry. To each chip 40 µl primer mix (250 µl Sequencing Primer and 250 µl Annealing Buffer) was injected into the flow cell and 35 µl primer mix were added to each port. The chips were placed on a thermocycler and cycled one time at 95° C. for 2 minutes, then 37° C. for 2 minutes, then 4° C. The chips were rinsed once with 200 µl Annealing Buffer and aspirated. To each chip, 60 µl Enzyme Mix was added (60 µl Annealing Buffer and 6 µl PSP4 enzyme) and incubated for 5 minutes. The chips were vacuum dried and 100 µl Annealing Buffer was added immediately. The chips were loaded onto the Ion Proton System for sequencing.

Sequencing

The Ion Proton System was initialized with Hi-Q 200 materials and sequencing was performed using 400 flows.

Results

Figure 3A:
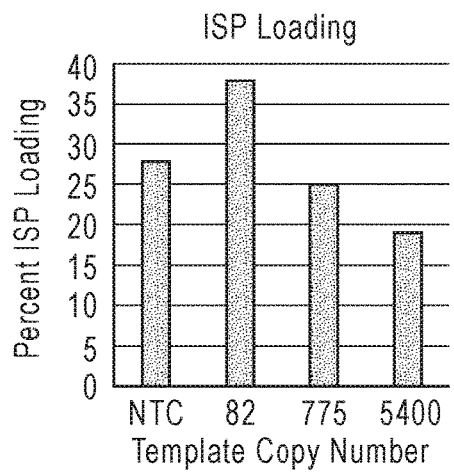
FIGS. 3A-3F are bar graphs showing various metrics of high-throughput sequencing after a pre-seeding amplification reaction using ISPs with no template control (NTC) and ISPs pre-seeded with ~82, ~775, and ~5,400 copies/ISP.
Figure 3B:
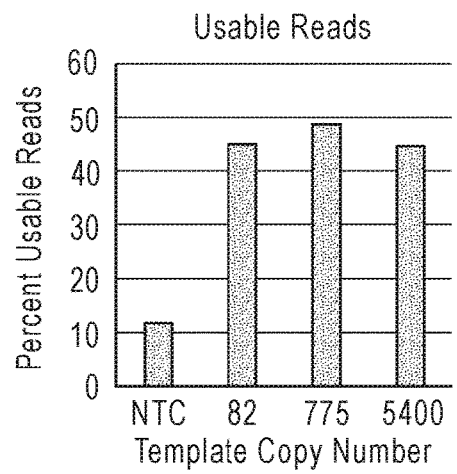
Figure 3C:
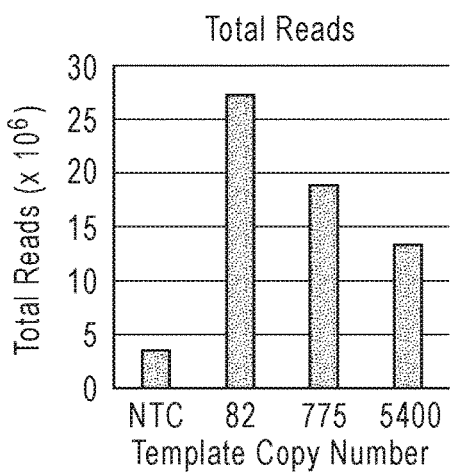
Figure 3D:
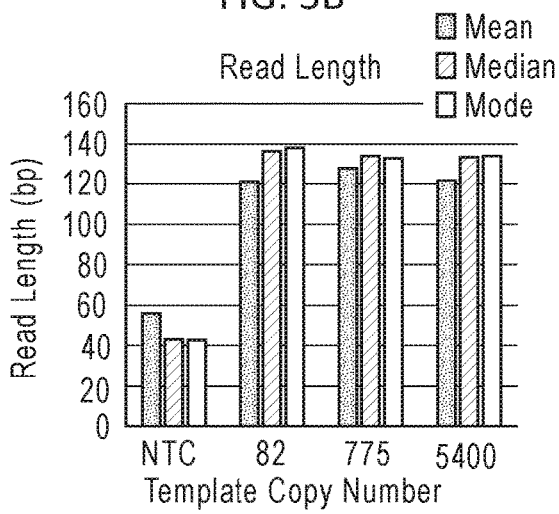
Figure 3E:
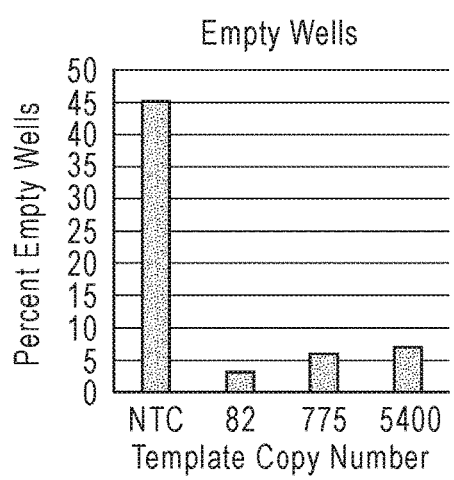
Figure 3F:
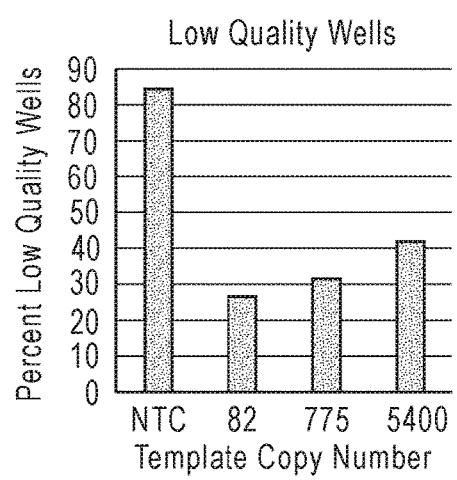

Pre-seeding the ISPs with monoclonal templates and then loading the pre-seeded onto an Ion Torrent sequencing chip generated better sequencing metrics than the NTC ISPs, which had monoclonal templates attached and amplified in one reaction. The percentage of ISP loaded increased with 82 copies of template pre-seeded onto the ISPs although higher levels of pre-seeding decreased the percentage of ISP loaded below the NTC ISPs (FIG. 3A). The percentage of usable reads increased with the pre-seeded ISPs (FIG. 3B). The pre-seeded ISPs also had up to a 9-fold increase in total reads relative to the NTC ISPs and greater than 2-fold increases in the mean, median, and mode of the read lengths (FIGS. 3C-3D). All the pre-seeded ISPs showed lower percentages of low quality wells and wells with no template (FIGS. 3E-3F). This example demonstrates that ISPs can be pre-seeded with monoclonal template nucleic acid molecules in a method where templating is performed on ISPs distributed within the wells of an Ion Torrent chip, to achieve improved sequencing data.

Example 3

Pre-Seeding ISPs with a Complex Library in an RPA Reaction

As in the previous example, this example provides a method to pre-seed ISPs. However, in the method disclosed in this example the templating reaction was done using a short RPA reaction instead of a single PCR cycle. Furthermore, the reaction was performed on ISPs in the wells of an Ion Torrent 541 Chip. After the RPA pre-seeding reaction, the pre-seeded ISPs were washed before a second isothermal RPA reaction (a templating reaction) was performed. The ISPs generated with a two-step process of pre-seeding ISPs followed by a templating reaction where template nucleic acid molecules were washed away before the templating reaction, were compared to ISPs that underwent a single RPA amplification without washing, which had the same template polynucleotides in the reaction mixture for the entire incubation. Four replicates of each of the one-step and two-step reactions were performed and compared.

Pre-Seeding Reaction

Accordingly, 500,000,000 ISPs were added to the wells of an Ion Torrent Chip and were pre-seeded with 160,000,000 copies of 130 base pair fragments of the *E. coli* genome with adapters on the ends of the fragments (A-B, A-AV5, or A-AV6) and the other components in the pre-seeding reaction mixture (same as in Example 2). The adapters included primer binding sites that facilitated binding to an immobilized universal primer (primer B, AV5, or AV6) attached to the ISPs, a universal primer in solution (primer A) during the pre-seeding and templating reaction, and sequencing primers. Briefly, 40 µl of the pre-seeding reaction mixture was added to the chip and each port was filled with 35 µl of pre-seeding reaction mixture. The pre-seeding reaction was incubated for 2.5 minutes at 40° C. and then stopped by rinsing with 200 µl 0.5 M EDTA under vacuum and then aspirated dry. The pre-seeded ISPs were washed with Annealing Buffer.

The templating reactions for the NTC ISPs were assembled as above and incubated at 40° C. incubation for 30 minutes. The NTC ISPs were processed in the same fashion as the pre-seeded ISPs after the templating reaction.

Templating Reaction

The templating reaction was performed as in Example 2. The templating reaction for the pre-seeded ISPs incubated for 30 minutes at 40° C.

Sequencing

Sequencing was performed using an Ion Torrent PI™ Sequencing HiQ 200 Kit as in Example 1.

Results

Pre-seeding the ISPs with template nucleic acid molecules and then templating the attached template nucleic acid molecules in a second reaction (i.e. a templating reaction) generated an average of 7,750,000 more reads than the templated ISPs generated without a separate pre-seeding reaction. Furthermore, other sequencing metrics were better with a pre-seeding reaction. For the one-step and two-step (separate pre-seeding followed by templating) reactions, the mean AQ20 scores were 109 and 110.75 and the mean AQ20GBases scores were 2.375 and 3.075, respectively. This example demonstrates that ISPs pre-seeded with a complex population of template nucleic acid molecules improves sequencing data generated on the template.

Example 4

Pre-Seeding ISPs with a Complex Library in a Bulk Isothermal Amplification

As in the previous example, this example provides a method to pre-seed ISPs with a complex population of template nucleic acid molecules. However, this example provides a pre-seeding RPA reaction with a longer incubation. After the pre-seeding reaction, the pre-seeded ISPs were enriched using MyOne magnetic beads before a second isothermal RPA reaction (i.e. templating reaction) was performed. After the templating reaction, the templated ISPs were further enriched using MyOne magnetic beads before being processed for downstream sequencing. The ISPs generated with a two-step process of pre-seeding ISPs followed by a templating reaction where template nucleic acid molecules were washed away before the templating reaction, were compared to ISPs that underwent a single RPA amplification without washing, which had the same template polynucleotides in the reaction mixture for the entire incubation.

Pre-Seeding Reaction

A pre-seeding reaction with a mix of A' primers and a blocked P1 primer was performed (see FIG. 4). A tube comprising 50 µl of an Annealing Buffer (Ion PGM™ Hi-Q™ View Sequencing Solutions, (Part No. A30275)), Primer Mix S (a mix of 3 A' primers: 5'-ACG ATC CAT CTC ATC CCT GCG TGT C-3' (SEQ ID NO: 4); 5'-TCC ATA AGG TCA GTA ACG ATC CAT CTC ATC CCT GCG TGT-3' (SEQ ID NO: 5); and 5'-/5-Bio/TCC ATA AGG TCA GTA ACG ATC CAT CTC ATC CCT GCG TGT-3' (SEQ ID NO: 5)), a blocked fusion primer (5'-CCT ATC CCC TGT GTG CCT TGG CAG TCT CAG CCA CTA CGC CTC CGC TTT CCT CTC TAT GGA A/3-Phos/-3'; SEQ ID NO: 6), $7.5 \times 10^6$ ISPs, and 35 pM 130 bp template nucleic acid molecules from a human genome library was vortexed, briefly spun and incubated at 98° C. for 2 minutes, and then incubated at 37° C. for 2 minutes. Another aliquot of Annealing Buffer was added (75 µl) and the solution was transferred to a new tube and vortexed. An Ion PGM™ Template IA Pellet (ThermoFisher Scientific, Waltham, Mass.) was rehydrated with 720 µl Ion PGM™ Template IA Rehydration Buffer, thoroughly mixed, and stored on ice. 375 µl of the rehydrated Ion PGM™ Template IA Pellet were combined with the previously prepared 125 µl solution containing the library, vortexed, then placed back on ice. The mixture was combined with 150 µl of pre-mixed Ion PGM™ Template IA Start Solution, thoroughly mixed to form the pre-seeding reaction mixture, briefly centrifuged, and placed on ice. To initiate the pre-seeding reaction, the tube was placed in a 40° C. heat block and then incubated for 4 minutes at 40° C. to generate pre-seeded ISPs. The pre-seeding reaction was stopped by the addition of 650 µl of 100 mM EDTA followed by vortexing.

A control reaction was assembled as above, with the following differences: $5.625 \times 10^6$ ISPs and 11 pM template were used and the 40° C. incubation was maintained for 30 minutes. These control reactions were processed in the same fashion as the pre-seeded samples subsequent to enriching the templated ISPs.

Enriching the Pre-Seeded ISPs

The pre-seeded ISPs were enriched using MyOne beads (ThermoFisher Scientific, Waltham, Mass.). Briefly, 100 µl of MyOne beads were added to the tube with the pre-seeded ISPs and vortexed. The tube was rotated for 10 minutes, spun, and placed on a magnetic tube rack. After the beads were fully pelleted, the supernatant was removed and discarded. The beads were washed once with 1 ml of Ion PGM™ Wash Solution using the magnetic tube rack. Then the beads were washed once with 1 ml 3 mM SDS solution using the magnetic tube rack and the supernatant was transferred to a new tube for further processing. The supernatant from the SDS wash was spun for 8 minutes at 21,000 rcf and the supernatant was removed to leave approximately 50 µl. The pre-seeded ISPs were resuspended with 150 µl of melt-off solution (125 mM NaOH and 0.1% Tween 20) and transferred to a new tube. The tube was spun for 5 minutes at 15,000 rcf and the supernatant was removed to leave 10 µl solution. 190 µl water was added to the pre-seeded ISPs and 2 µl was removed for analysis on a Guava easyCyte Flow Cytometer. The tube was spun for 5 minutes at 15,000 rcf and the supernatant was removed to leave 10 µl of solution containing the remaining pre-seeded ISPs.

Templating Reaction

111 µl of Annealing Buffer and 4 µl of Primer Mix S were added to the tube containing the pre-seeded ISPs. The pre-seeded ISPs were pipetted up and down to combine and the entire solution was transferred to a new tube. 375 µl of a rehydrated Ion PGM™ Template IA Pellet was added to the tube and the tube was vortexed, briefly spun, and placed on ice. The reaction mixture was combined with 150 µl of pre-mixed Ion PGM™ Template IA Start Solution, thoroughly mixed, briefly centrifuged, and placed on ice. To initiate the templating reaction, the tube was placed in a 40° C. heat block and then incubated for 30 minutes at 40° C. The templating reaction was stopped by the addition of 650 µl of 100 mM EDTA followed by vortexing.

Enriching the Templated ISPs

The templated ISPs were enriched using MyOne beads (ThermoFisher Scientific, Waltham, Mass.). Briefly, 100 µl of MyOne beads were added to the tube with the templated ISPs and vortexed. The tube was rotated for 10 minutes, spun, and placed on a magnetic tube rack. After the beads were fully pelleted, the supernatant was removed and discarded. The beads were washed once with 1 ml of Ion PGM™ Wash Solution using the magnetic tube rack. 200 µl of melt-off solution (125 mM NaOH and 0.1% Tween 20) was added to the tube, mixed, and the solution was transferred to a new tube. The tube was spun for 5 minutes at 15,000 rcf and the supernatant was removed. The ISPs were washed with 200 µl water and 2 µl was removed for analysis on a Guava easyCyte Flow Cytometer. The ISPs were then processed for sequencing according to the Proton Hi-Q user guide.

Results

Pre-seeding the ISPs with template nucleic acid molecules and then templating the attached template nucleic acid molecules in a second reaction (i.e. a templating reaction) generated an average of 9,167,000 more reads than the templated ISPs generated without a separate pre-seeding reaction. Furthermore, other sequencing metrics were better with a pre-seeding reaction. For the one-step and two-step (separate pre-seeding followed by templating) reactions, the mean AQ20 scores were 105 and 110.25 and the mean AQ20GBases scores were 2.889 and 4.267, respectively. This example demonstrates that ISPs pre-seeded with a complex population of template nucleic acid molecules yield improved sequencing data for the template.

Example 5

Seeding

A library (2.4B copies) was mixed with biotin TPCRA (1 uL at 100 uM) in a PCR tube. The tube is filled to 20 uL with 1× Platinum HiFi mix. The tube was thermo cycled on a thermocycler one time (2 min at 98 C, 5 min at 37 C, 5 min at 54 C). 6 billion beads were added to the tube from. 1× HiFi was added to increase volume by 50% (i.e. 20 uL of beads+10 uL of Platinum Hifi mix). The solution was thermo cycled on a thermocycler once (2 min at 98 C, 5 min at 37 C, 5 min at 54 C).

1 mL myOne beads are pipetted into a 1.5 mL tube (1 mL myOne beads used for 2 samples) and the tube was put on a magnet and the supernatant discarded. 1 mL 3% BSA in 1×PBS is added to the MyOne mixture, vortexed, pulse spun. The mixture was put on a magnet and the supernatant discarded. 1 mL AB is added to MyOne mixture, vortexed, pulse spun. The mixture was put on a magnet and the supernatant discarded. 250 uL AB is added to the MyOne mixture (one sample uses 125 uL 4× concentrated MyOnes). The purified MyOne mixture was transferred to new 1.5 mL tube.

Samples from the PCR tube were transfer to new 1.5 mL tube. 125 uL 4× concentrated MyOnes were added to the ISP mix. The mixture was pipetted up and down 3 times (200 uL/s) and let sit for 10 min. The mixture was put on a magnet, MyOne captured ISP were pulled out (chef speed 80 uL/s) and the supernatant was discarded. 20 uL NF water was added, pulse vortexed, pulse spun, and put on magnet to pellet MyOne.

Chip Preparation

A chip was rinsed 2× with 200 µL NF water.

Magnetic ISP Loading 20 ul of ISP mixture was mixed with 4.5 uL 10× annealing buffer and 20.5 uL water (total 45 ul). ISPs were vortexed and combined with 10× annealing buffer and water. The ISP solution was vortexes and quick spun. The ISP solution was slowly injected into the chip through the loading port. Magnetic loading was performed for 40 minutes at 30 sec/sweep. 200 µL of foam (0.2% Triton in 1× AB) was injected through the chip, and the excess is extracted. While vacuuming exit port, 200 µL 1× AB was added and then aspirated to dry chip. While vacuuming exit port, 200 µL Flush (60% AB/40% IPA) was aspirated and then aspirated to dry chip. While vacuuming exit port, 200 µL 1× AB was added. The chip is kept in 1× AB until ready to amplify ISPs on chip.

Amplification—Keep all Reagents on Ice

1st Step Amplification

A tube with biotinylated primer A and blocking molecule (Neutravidin) was prepared and incubated on ice for >15 minutes. Solutions include 1.1 uL 100 uM primer per chip and 1 uL 10 mg/mL NAv (rehydrated in 0-PEG buffer) per chip. 871 µL of Rehydration buffer was added to 1× IA pellet (lot LTBP0047, PN 100032944). The solution was pulse vortexed 10×, quick spun to collect tube contents. The contents were split into two tubes of equal volume (Put 900 uL in separate tube). One tube of 900 µL was used for 1st step amplification, save other tube of 900 µL for 2nd step amplification.

For each chip to be run, 60 µL pellet solution was slowly injected into the chip. The displaced annealing buffer was aspirated from exit port. The chip was incubated with pellet solution at RT for 4 minutes. 177.4 µL start solution was added to tube of pellet solution, pulse vortexed 10× and quick spun. 110 uL/chip of starter solution was transferred to tube of primer and blocker, pulse vortexed 10× and quick spun. For each chip, ~60 µL activated pellet solution was slowly injected into the chip. All displaced fluid was aspirated from both ports. 25 µL pellet solution was added to each port. Chips were placed onto hot plate (thermocycler) set to 40° C. The chips were covered with pipette tip box lid or similar (not the heated thermocycler cover) and let incubate for 2.5 minutes.

Short Reaction Stop and Clean Between Amplification Steps

Amplified chips were placed near hood equipped with vacuum. While vacuuming exit port, 200 µL 0.5 M EDTA pH 8 (VWR E522-100ML) was added then aspirated to dry the chip. While vacuuming exit port, 200 µL 1× AB was aspirated and then aspirate to dry the chip. The addition of AB was repeated and the chip is left wet for 2nd step amplification. (Vac out the AB twice and leave the 3rd AB in chip)

2nd Step Amplification (No Blocker)

A tube with biotinylated primer A was prepared and incubated on ice for >15 minutes. Solutions include 1.1 uL 100 uM primer per chip. 871 µL of Rehydration buffer was added to 1× IA pellet (lot LTBP0047, PN 100032944). The solution was pulse vortexed 10×, quick spun to collect tube contents. After discarding appropriate volume of pellet solution, 6.6 µL 100 uM biotinylated primer was added to pellet mix and it was pulse vortexed 10×.

177.4 µL start solution was added to tube of pellet solution, pulse vortex 10× and quick spin. For each chip, ~60 µL activated pellet solution was injected into the prespun chip. Displaced fluid was aspirated from both ports. An additional 25 µL pellet solution was added to each port. Chips were placed onto hot plate (thermocycler) set to 40° C. The chips were covered with pipette tip box lid or similar (not the heated thermocycler cover) and let incubate for 20 minutes.

Reaction Stop and Clean Up

Amplified chips were placed near hood equipped with vacuum. While vacuuming exit port, 200 µL 0.5 M EDTA pH 8 was added and the chips are aspirated to dry chip. While vacuuming exit port, 200 µL 1× AB) was added and then aspirated to dry chip. While vacuuming exit port, 200 µL 1% SDS solution in water (Ambion PN AM9822) was added and then aspirated to dry chip. The SDS wash is repeated. While vacuuming exit port, 200 µL formamide was added. The chip was incubated 3 minutes at 50 C, then aspirated to dry the chip. While vacuuming exit port, 200 µL Flush (50% IPA/50% AB) solution was added. The chip was aspirated to dry. While vacuuming exit port, 200 µL annealing buffer was added. The chip was left in 1× AB until ready for priming.

On Chip Sequencing Primer Hybridization and Enzyme

Sequencing primer tube was thawed. Primer mix of final 50%/50% AB/primer mixture was prepared and vortexed well. If tube of sequencing primer has a volume of 250 µL, 250 µL 1×AB was added. The chip was aspirated to dry then 80 µL primer mix was added to the chip (50 µL in flow cell, 30 µL in ports). The chip was placed on thermocycler & incubated at 50° C. for 2 min, 20° C. for 5 min. 200 µL 1× AB was injected while vacuuming exit port. The enzyme mix was prepared with 60 µL annealing buffer & 6 µL PSP4 enzyme. The ports were cleaned and vacuumed to dry chip from the inlet port. 60 µL enzyme mix was added to the chip and incubated at RT for 5 minutes. The chip was aspirated to dry the chip from the inlet port. 100 µL of 1× AB was added to the chip immediately. The ports were cleaned, the back of the chip was dried, and the chip was loaded on the Proton for sequencing.

Example 6

Seeding

An Ampliseq Exome library (2.4B copies) with A and B adapters was mixed with a 5'-biotinylated primer complimentary to the A adapter, TPCRA, (1 uL at 100 uM) in a PCR tube. The tube was filled to 20 uL with 1× Platinum HiFi mix containing Taq DNA polymerase high fidelity, salts, magnesium and dNTPs. The tube was thermo cycled on a thermocycler one time (2 min at 98° C., 5 min at 37° C., 5 min at 54° C.). Ion Sphere Particle (ISP) beads (6 billion), each having thousands of B primer immobilized thereto, were added to the tube. 1× HiFi was added to increase volume by 50% (i.e. 20 uL of beads+10 uL of Platinum Hifi mix). The solution was thermo cycled on a thermocycler once (2 min at 98° C., 5 min at 37° C., 5 min at 54° C.).

In an alternative method, in a PCR tube, 1.2 billion copies of Ion Ampliseq Exome library (20 µL 100 pM, with standard Ion Torrent A and P1 library adapters) was mixed with 3 µL 3 µM biotin-TPCRA (sequence 5'biotin-CCA TCT CAT CCC TGC GTG TC-3'; SEQ ID NO: 2) and 3 µL 1.5 µM B-trP1 (trP1 is a 23mer segment of the Ion P1 adapter with sequence CCT CTC TAT GGG CAG TCG GTG AT (SEQ ID NO: 1); B is the ISP primer sequence) primers, and 9 µL Ion Ampliseq HiFi Master Mix 5×. The volume was filled up to 45 µL with 10 µL nuclease-free water. The tube was thermocycled on a thermocycler with the following temperature profile: 2 min at 98° C., 2 cycles of [15 sec at 98° C.-2 min at 58° C.], final hold at 10° C. After the thermocyling, 6 billion ISPs (75 µL 80 million/µL), and 6 Ion Ampliseq HiFi Master Mix 5× were added to the tube. 5 µL nuclease-free water was also added to bring up total volume to 131 µL. The solution was mixed well and the tube was returned to the thermocycler. A third cycle of amplification was performed with the following temperature profile: 2 min at 98° C., 5 min at 56° C., final hold at 10° C. After thermocycling, add 5 µL EDTA 0.5M and mix to stop the reaction Enriching of the ISPs MyOne superparamagnetic beads (1 mL) with streptavidin covalently coupled to the bead surface were pipetted into a 1.5 mL tube (1 mL MyOne beads used for 2 samples) and the tube was put on a magnet and the supernatant discarded. 1 mL 3% BSA in 1×PBS was added to the MyOne mixture which was then vortexed and pulse spun. The mixture was put on a magnet and the supernatant discarded. Annealing buffer (AB; 1 mL) was added to the MyOne mixture, vortexed and pulse spun. The mixture was put on a magnet and the supernatant discarded. AB (250 uL) was added to the MyOne mixture (one sample uses 125 uL 4× concentrated MyOnes). The purified MyOne mixture was transferred to a new 1.5 mL tube.

Samples from the PCR tube containing the ISP mix were transferred to a new 1.5 mL tube. Concentrated (4×) MyOne beads (125 uL) were added to the ISP mix. The mixture was pipetted up and down 3 times (200 uL/s) and then allowed to sit for 10 min. The mixture was put on a magnet, MyOne-captured ISPs were pulled out (chef speed 80 uL/s) and the supernatant was discarded. Nuclease-free (NF) water (20 uL) was added to the tube which was then pulse vortexed, pulse spun, and put on magnet to pellet the MyOne beads.

In an alternative method of enriching the ISPs, 120 µL of MyOne Streptavidin C1 beads were transferred into a separate tube and the tube was placed on a magnet to pellet the magnetic beads. The supernatant was discarded and the tube was removed from the magnet. The beads were washed by resuspending in 150 µL Ion Torrent Annealing Buffer, then pelleting on a magnet. The supernatant was discarded, and the wash was repeated one more time with 150 µL Annealing Buffer. After discarding supernatant from the second wash, the washed MyOne C1 beads were resuspended with 50 µL Annealing Buffer. The whole content of the washed MyOne C1 in Annealing Buffer was transferred to the thermocycled PCR tube containing library and ISPs. The pipette volume was set to 160 µL, and the contents were mixed slowly by pipetting up and down three times at 1 sec per aspiration or dispensing motion. The mixture was allowed to sit at room temperature for 30 min without agitation to allow magnetic beads to capture library seeded ISPs. The tube was then put on a magnet to pellet magnetic beads and the supernatant was discarded. Tween-20 (25 µL 0.1%) in water was added to the pellet. The mixture was vortexed vigorously to elute seeded ISPs from MyOne C1 beads. The tube was pulse spun then returned to magnet. The supernatant (eluent) containing seeded ISPs was collected in a fresh tube for downstream chip loading and amplification steps.

Chip Preparation

A chip was rinsed 2× with 200 µL NF water.

Magnetic Loading of ISPs onto Chips

Several methods of preparing the ISP/library mixture and loading it onto an Ion Torrent semiconductor chip containing reaction chamber microwells were used. In one method, the ISP/Library mixture (20 ul) was mixed with 4.5 µl 10× annealing buffer and 20.5 µl water (total 45 µl). The mixture was vortexed and spun. The ISP solution was slowly injected into the chip through the loading port. Magnetic loading was performed for 40 minutes at 30 sec/sweep. A foam (200 µL) containing 0.2% Triton in 1× AB was injected through the chip, and the excess was extracted. While vacuuming the exit port of the chip, 200 µL 1× AB was injected into the chip and then aspirated to dry the chip. While vacuuming exit port, 200 µL Flush (60% AB/40% IPA) was then injected into the chip and then aspirated to dry chip. While vacuuming exit port, 200 µL 1× AB was then added by injection into the chip. The chip was kept in 1× AB until ready to amplify the nucleic acids on the ISPs on the chip.

In another method, 150 µL Dynabeads M-270 streptavidin (Thermo Fisher Scientific), which are magnetic beads with streptavidin bound to the surface thereof, were transferred to a tube which was then placed in a magnet to pellet magnetic beads. The supernatant was discarded and the tube was removed from the magnet. The following was then added to the tube containing the M-270 pelleted beads: 20 µL ISP mixture from the seeding process, 9 µL 5× Annealing Buffer, and 16 μL nuclease-free water for a total 45 μL. Alternatively, 20 ul of ISP/Library mixture was mixed with 3.2 uL 10× annealing buffer 3 uL concentrated M270 magnetic beads and 5.8 uL water for a total of 32 ul. The mixture was mixed to resuspend the M-270 pellet, and slowly injected into the chip through the loading port. A magnet placed beneath the chip was swept across the chip back and forth repeatedly to load ISPs into chip microwells. The magnetic loading sweeping was performed for 40 minutes at 30 sec/sweep. After loading, a 15 mL falcon tube containing 5 mL 1% SDS was vigorously shaken to generate a dense foam, 800 μL of which was then injected through the chip to remove magnetic beads from the chip flow cell. Flow through at the chip exit was discarded. Annealing Buffer (200 μL) was then injected through the chip, and the flow through was discarded. The chip was vacuumed dry from the chip exit. Flush (200 μL of 60% Annealing Buffer, 40% IPA) was injected through the chip which was then vacuumed dry. Annealing Buffer (200 μL) was injected to fill the chip flow cell, and the flow through was discarded at the chip exit. The chip was left filled with Annealing Buffer until ready to amplify in downstream amplification steps.

Amplification

First Step Amplification

For each chip being amplified, 1.1 uL biotinylated primer A (100 uM) and 1 uL blocking molecule (10 mg/mL Neutravidin rehydrated in buffer) were combined in a tube and incubated on ice for >15 minutes.

Rehydration buffer (871 μL) was added to 1× IA pellet (PN 100032944) containing reaction components for conducting recombinase-polymerase amplification (e.g., recombinase, polymerase, single-stranded binding protein, nucleotides, buffers and other ingredients) from the ION PGM™ TEMPLATE IA 500 kit. The solution was pulse vortexed 10× and quick spun to collect tube contents. The rehydrated contents (referred to as "pellet solution", at roughly 900 ul) were kept on ice during the process.

For each Ion Torrent chip, 60 μL of rehydrated IA pellet solution was slowly injected into the chip. The displaced annealing buffer was aspirated from the exit port. The chip was incubated with rehydrated IA pellet solution at RT for 4 minutes.

For each chip being amplified, 90 uL of rehydrated IA pellet solution was transferred to a new tube. The previously prepared biotinylated primer A and neutravidin blocking molecule (2.1 uL) was added and pulse mixed. A start solution (30 μL), containing an aqueous solution of 28 mM Mg(OAc)$_2$, 10 mM Tris acetate and 3.75% (V/V) methyl cellulose, was added to the tube of rehydrated IA pellet solution, pulse vortexed 10× and quick spun to form an activated amplification solution in a ~120 uL total volume. For each chip, ~60 μL activated amplification solution was slowly injected into the chip. All displaced fluid was aspirated from both ports. Next, 25 μL of remaining activated amplification solution was added to each chip port. Chips were placed onto a hot plate (thermocycler) set to 40° C. The chips were covered with a pipette tip box lid or similar cover (not the heated thermocycler cover) and allowed to incubate for 2.5 minutes.

Short Reaction Stop and Clean Between Amplification Steps

Amplified chips were taken off the hot plate or thermocycler. While vacuuming the exit port, 200 μL 0.5 M EDTA pH 8 (VWR E522-100ML) was injected into the chip and the chip was then aspirated to dry using a vacuum. While vacuuming the exit port, 200 μL 1× AB was injected into the chip which was then aspirated to dry. The addition of AB was repeated two more times and the chip was left filled for the 2nd step amplification. (The AB was vacuumed out twice and the third addition of AB was left in the chip.)

Second Step Amplification (No Blocker)

For each chip, 60 uL rehydrated pellet solution was slowing injected into the chip. The displaced annealing buffer was aspirated from the exit port. The chip was incubated with pellet solution at RT for 4 minutes.

For each chip being prepared, 90 uL of rehydrated pellet solution was transferred to a fresh tube. Biotinylated Primer A (1.1 uL of 100 uM) was added and the tube pulse vortexed and spun.

Start solution (30 μL) was added to the tube containing rehydrated pellet solution and Primer A and was pulse vortexed 10× and quick spun to generate an activated amplification solution. Approximately 60 μL activated amplification solution was injected into the chip. Displaced fluid was aspirated from both ports. An additional 25 μL of remaining amplification solution was added to each port. Chips were placed onto a hot plate (thermocycler) set to 40° C. The chips were covered with a pipette tip box lid or similar cover and allowed to incubate for 20 minutes.

Reaction Stop and Clean Up

Chips that had been subjected to amplification reactions were placed near a hood equipped with a vacuum. While vacuuming the exit port, 200 μL 0.5 M EDTA pH 8 was added and the chips were aspirated to dry the chips. While vacuuming the exit port, 200 μL 1× AB was added and then aspirated to dry the chip. While vacuuming the exit port, 200 μL 1% SDS solution in water (Ambion PN AM9822) was added and then aspirated to dry the chip. The SDS wash was repeated. While vacuuming the exit port, 200 μL formamide was added. The chip was incubated 3 minutes at 50° C., then aspirated to dry the chip. While vacuuming the exit port, 200 μL Flush (50% IPA/50% AB) solution was added. The chip was aspirated to dry. While vacuuming the exit port, 200 μL annealing buffer was added. The chip was left in 1× AB until ready for priming.

On Chip Sequencing Primer Hybridization and Enzyme Reaction

A tube containing Ion sequencing primer (100 uM) was thawed. For each chip being sequenced, a primer mixture of 40 uL annealing buffer and 40 uL sequencing primer was prepared and vortexed well. The chip was aspirated to dry then 80 μL of primer mixture was added to the chip (50 μL in flow cell, 15 μL in each port). The chip was placed on a thermocycler and incubated at 50° C. for 2 min, 20° C. for 5 min. 200 μL 1× AB was injected while vacuuming the exit port. An enzyme mixture was prepared with 60 μL annealing buffer and 6 μL sequencing enzyme (Ion PSP4 Sequencing Polymerase). The ports were cleaned and vacuumed to dry the chip from the inlet port. Enzyme mixture (60 μL) was added to the chip and incubated at RT for 5 minutes. The chip was aspirated to dry. AB (100 μL of 1×) was injected to fill the chip immediately. The ports were cleaned, the back of the chip was dried, and the chip was loaded on the Ion Torrent Proton (Thermo Fisher Scientific) apparatus for sequencing of the library nucleic acids.

Example 7

Figure 10:
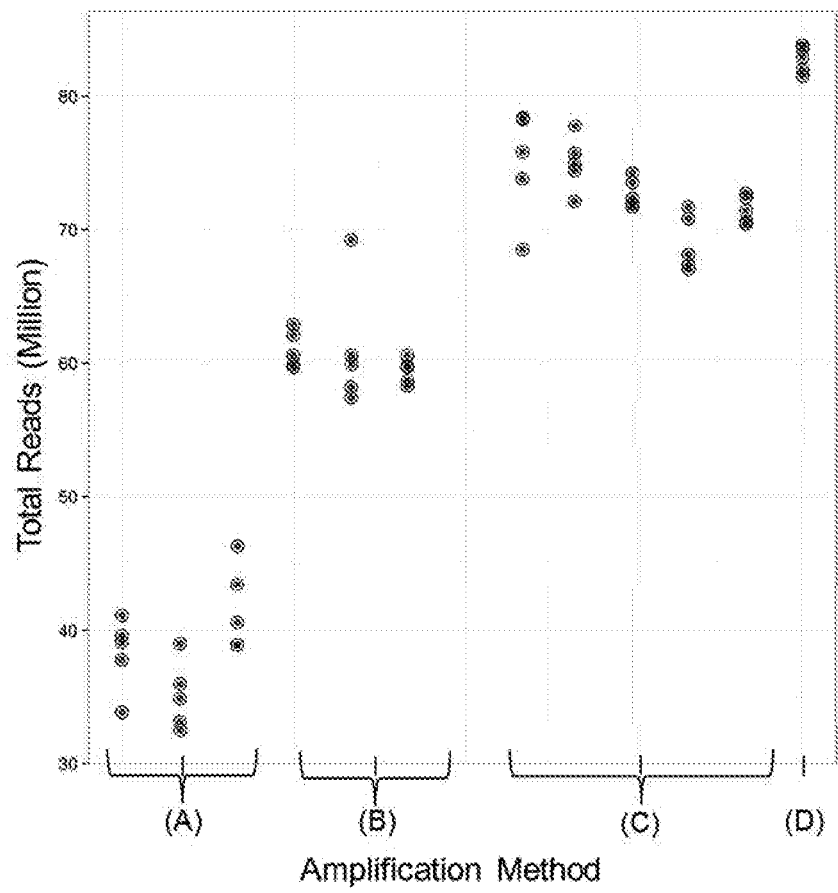
FIG. 10 is a graph of results of sequencing runs of nucleic acid templates generated using several different methods.

Comparison of Sequencing Results Using Different Nucleic Acid Manipulation Methods FIG. 10 shows the total usable reads for groups of nucleic acid sequencing runs of nucleic acid templates generated using four different amplification conditions (A-D in the figure). In method A, non-templated Ion Sphere Particles (ISPs) were loaded into microwells of Ion Torrent 541 chips according to methods described in Example 2 herein. Subsequently, library molecules (a 110-bp hg19 fragment library) with adaptors complimentary to the ISP primer were hybridized to the pre-loaded ISPs with a single 95° C. 1 min/37° C. 1 min thermocycling step following injection of the library amplicons into the chip. Following library hybridization, amplification was performed using a single-step RPA templating amplification method essentially as described in Example 2. The primers were not biotinylated. Method B employed two important changes to amplification protocol A: 1) an additional amplification step (a "first" amplification step) prior to the templating amplification and 2) incorporation of neutravidin and biotinylated solution primers in the added first amplification step. In this example, the first amplification step, which is an isothermal RPA amplification, is 2.5 minutes and contains an equivalent concentration of biotinylated solution primer and neutravidin. The second amplification step is 15 minutes and does not contain neutravidin. In this method, the first amplification step serves to locally amplify template copies while adding drag (via neutravidin) to limit well-2-well diffusion of nascent strands. After 2.5 minutes, enough local copies are created that the drag component is no longer needed. The second amplification step was then carried out as described in Example 2. In Methods C and D, a 220-bp hg19 Ampliseq Exome Library was used. Method C improves upon method B by replacing the library hybridization method in methods A and B, with a solution based pre-amplification ISP enrichment method as described in Example 6 herein. Thus, instead of performing all steps in wells, the first step of hybridizing the library to the ISPs was done in solution, then magnetic beads were added to the tube, the template-containing ISPs were enriched, and then separated from the magnetic beads and loaded into the wells for the 2-step amplification as was done in Method B. The pre-amplification enrichment method enables loading of ISPs with single library template copies. Finally, amplification method D, which was carried out according to Method C, employed a modified ISP primer sequence compared with method C. The modified primer, AV4, has the following sequence: ATTCGAGCTGTTCATCTGTATCTTGCGCTACCAA (SEQ ID NO: 7). As shown in FIG. 10, the combination of improvements made from Methods A-D enable total reads equivalent to sequencing carried out on template nucleic acids amplified through emulsion PCR The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Note that not all of the activities described above in the general description or the examples are required, that a portion of a specific activity may not be required, and that one or more further activities may be performed in addition to those described. Still further, the order in which activities are listed are not necessarily the order in which they are performed. Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment. When multiple low and multiple high values for ranges are given, a skilled artisan will recognize that a selected range will include a low value that is less than the high value. All headings in this specification are for the convenience of the reader and are not limiting. In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention. Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for generating nucleic acid molecules comprising a specific nucleotide sequence, comprising:

(a) obtaining a population of nucleic acid molecules in which each molecule comprises a first sequence of contiguous nucleotides at the 5' end of the molecule, a second sequence of contiguous nucleotides at the 3' end of the molecule and a third nucleotide sequence positioned between the first and second nucleotide sequences, wherein the first nucleotide sequence and second nucleotide sequence are different from each other, and wherein the first nucleotide sequences of the nucleic acid molecules are identical and the second nucleotide sequences of the nucleic acid molecules are identical among the population; and (b) subjecting the population of nucleic acid molecules to two or more cycles of nucleic acid amplification in the presence of one or more forward primers comprising an oligonucleotide sequence identical to the first nucleotide sequence and a reverse primer that is blocked at the 3' end and comprises an oligonucleotide sequence complementary to the second nucleotide sequence that is linked at the 5'end of the oligonucleotide sequence to a fourth nucleotide sequence that is not complementary to the second nucleotide sequence to generate nucleic acid products which comprise a sequence of nucleotides complementary to the fourth nucleotide sequence.

2. The method of claim 1, further comprising exposing single-stranded nucleic acids of the products of (b) to a single-stranded oligonucleotide that is identical to the fourth nucleotide sequence under annealing conditions thereby hybridizing the products of (b) that comprise a sequence of nucleotides complementary to the fourth nucleotide sequence to the single-stranded oligonucleotide that is identical to the fourth nucleotide sequence to generate a partially double-stranded oligonucleotide-bound product.

3. The method of claim 2, further comprising extending the 3' end of the oligonucleotide that is hybridized to the product that comprises a sequence of nucleotides complementary to the fourth nucleotide sequence thereby generating a double-stranded nucleic acid by synthesizing a nucleic acid strand comprising the single-stranded oligonucleotide that is identical to the fourth nucleotide sequence and having a nucleotide sequence that is complementary to the product to which it is hybridized.

4. The method of claim 3, wherein the nucleic acid strand comprising the single-stranded oligonucleotide sequence that is identical to the fourth nucleotide sequence is attached to a support at the 5' end of the strand, and further comprising isolating the synthesized single-stranded nucleic acid strand attached to the support by removing the support from any other nucleic acids that are not bound to the support.

5. The method of claim 4, wherein the support is a solid support bead.

6. The method of claim 4, wherein the extending is carried out using a recombinase-polymerase amplification (RPA) reaction.

7. The method of claim 6, wherein the RPA reaction is performed by incubating an RPA reaction mixture for 2 to 5 minutes at a temperature between 35° C. and 45° C.

8. The method of claim 4, wherein the extending is carried out using a polymerase chain reaction (PCR).

9. The method of claim 8, wherein the extending includes performing three PCR cycles.

10. A method of preparing a device for nucleic acid analysis, the method comprising:
generating a template nucleic acid including a capture sequence portion, a template portion, and a primer portion modified with a linker moiety according to the method of claim 1, wherein the sequence of nucleotides complementary to the fourth nucleotide sequence corresponds to a capture sequence portion, the third nucleotide sequence is a template portion, and the forward primer is modified with a linker moiety and the forward primer sequence corresponds to the primer portion;
capturing the template nucleic acid on a bead support having a plurality of capture primers complementary to the capture sequence portion of the template nucleic acid, the capture primers hybridizing to the capture sequence portion of the template nucleic acid;
linking the captured template nucleic acid to a magnetic bead having a second linker moiety to form a bead assembly, the second linker moiety attaching to the first linker moiety; and
loading the bead assembly into a well of a device for nucleic acid analysis using a magnetic field, wherein the device is a sequencing device.

11. The method of claim 10, further comprising extending the capture primer complementary to the template nucleic acid to form a sequence target nucleic acid attached to the bead support.

12. The method of claim 11, further comprising denaturing the template nucleic acid and the sequence target nucleic acid to release the magnetic bead from the bead support.

13. The method of claim 12, wherein denaturing includes enzymatic denaturing or denaturing in the presence of an ionic solution.

14. The method of claim 11, wherein the extending is carried out using a recombinase-polymerase amplification (RPA) reaction.

15. The method of claim 14, wherein the RPA reaction is performed by incubating an RPA reaction mixture for 2 to 5 minutes at a temperature between 35° C. and 45° C.

16. The method of claim 11, wherein the extending is carried out using a polymerase chain reaction (PCR).

17. The method of claim 16, wherein the extending includes performing three PCR cycles.

18. The method of 12, further comprising amplifying the sequence target nucleic acid to form a population of sequence target nucleic acids on the bead support in the well.

19. The method of claim 18, wherein amplifying the sequence target nucleic acid includes performing recombinase polymerase amplification (RPA), where performing RPA includes performing RPA for a first period, washing, and performing RPA for a second period, the first period shorter than the second period.

* * * * *